(12) United States Patent
Wang et al.

(10) Patent No.: US 10,266,811 B2
(45) Date of Patent: Apr. 23, 2019

(54) METHODS OF TREATMENT USING RECOMBINANT OXALATE OXIDASE

(71) Applicant: NEXTTOBE AB, Uppsala (SE)

(72) Inventors: Yi Wang, Hubei (CN); Xiaofeng Wang, Hubei (CN); Haifeng Liu, Hubei (CN); Wei Wang, Hubei (CN)

(73) Assignee: NEXTTOBE AB, Uppsala (SE)

( * ) Notice: Subject to any disclaimer, the term of this patent is extended or adjusted under 35 U.S.C. 154(b) by 0 days.

(21) Appl. No.: 15/106,914

(22) PCT Filed: Dec. 22, 2014

(86) PCT No.: PCT/EP2014/078984
§ 371 (c)(1),
(2) Date: Jun. 21, 2016

(87) PCT Pub. No.: WO2015/097148
PCT Pub. Date: Jul. 2, 2015

(65) Prior Publication Data
US 2017/0037383 A1    Feb. 9, 2017

(30) Foreign Application Priority Data
Dec. 23, 2013 (EP) ..................... 13199309

(51) Int. Cl.
*C12N 9/96* (2006.01)
*C12N 9/02* (2006.01)
*A61K 38/44* (2006.01)

(52) U.S. Cl.
CPC ............ *C12N 9/0008* (2013.01); *A61K 38/44* (2013.01); *C12Y 102/03004* (2013.01)

(58) Field of Classification Search
None
See application file for complete search history.

(56) References Cited

U.S. PATENT DOCUMENTS 4,455,371 A    6/1984 Richardson et al.

FOREIGN PATENT DOCUMENTS

| WO | WO 2006/135925 A2 | 12/2006 |
| WO | WO 2007/070052 A2 | 6/2007 |
| WO | WO 2011/066282 A1 | 6/2011 |
| WO | WO 2011/082304 A1 | 7/2011 |

OTHER PUBLICATIONS

Kanauchi et al., "Oxalate and Oxalate Oxidase in Malt," Journal of the Institute of Brewing, vol. 115, No. 3, pp. 232-237, May 2009.
Raghavan et al., Degradation of oxalate in rats implanted with immobilized oxalate oxidase, FEBS Letters, vol. 195, No. 1-2, pp. 101-105, Jan. 1986.
Srivastava et al., "An oxalic acid oxidase in the leaves of Bougainvillea spectabilis," Biochemical Journal, vol. 85, pp. 33-38, Oct. 1962.
Obzansky et al., "Quantification of Urinary Oxalate with Oxalate Oxidase from Beet Stems," Clinical Chemistry, vol. 29, No. 10, pp. 1815-1819, Oct. 1983.
De Los Reyes et al., "Cultivar-specific seedling vigor and expression of a putative oxalate oxidase germin-like protein in sugar beet (*Beta vulgaris* L.)," Theoretical and Applied Genetics, vol. 107, pp. 54-61, Jun. 2003.
Lane, "Oxalate oxidases and differentiating surface structure in wheat: germins," Biochemical Journal, vol. 349, No. 1, pp. 309-321, Jul. 2000.
Bernier et al., "Germins and germin-like proteins: Plant do-all proteins. But what do they do exactly?," Plant Physiology and Biochemistry, vol. 39, No. 7-8, pp. 545-554, Jul. 2001.
Opaleye et al., "Structural and Spectroscopic Studies Shed Light on the Mechanism of Oxalate Oxidase," Journal of Biological Chemistry, vol. 281, No. 10, pp. 6428-6433, Mar. 2006.
Database EMBL [Online], "Musa acuminate germin-like protein mRNA, complete cds.," retrieved from EBI accession No. EMBL:AF417204, Sep. 24, 2001.
Database EMBL [Online], "SubName: Full Germin-like protein," retrieved from EBI accession No. UNIPOROT: Q93WX8, Dec. 1, 2001.
International Search Report dated Mar. 19, 2015 in application No. PCT/EP2014/078984.

*Primary Examiner* — Hope Robinson
(74) *Attorney, Agent, or Firm* — Foley & Lardner LLP

(57) ABSTRACT

Novel oxalate oxidases are provided, which have suitable oxalate degrading activity near physiological pH (7.4). The properties of these OxOx make them potential drug candidates for use in reducing oxalate concentration in patients suffering from excess of oxalate. Especially due to the high activity at physiological pH, the OxOx's are suitable drug candidates for parenteral administration, i.e. to reduce the oxalate concentration in the plasma.

Figure 1:
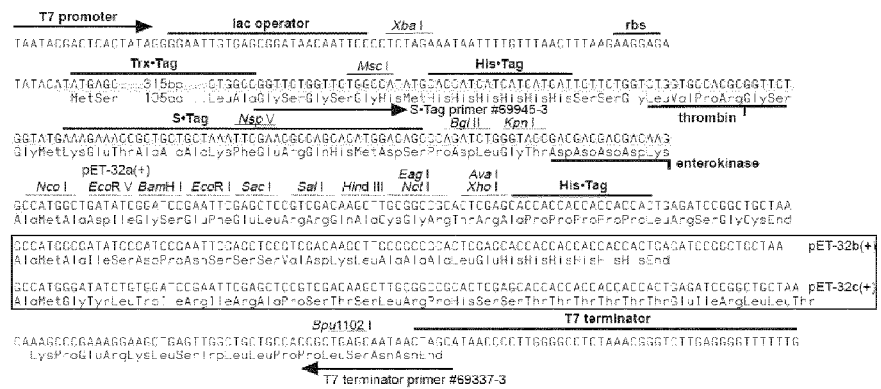

20 Claims, 43 Drawing Sheets
Specification includes a Sequence Listing.

Modifications of the pET-32 vector to generate the pAT plasmid.
The DNA sequence highlighted in yellow was deleted in a pET-32 vector to generate the pAT plasmid.

Schematic diagram of the Pichia expression plasmid Zα-5102

Schematic diagram of the Pichia expression plasmid GAPZα-5102

Schematic diagram of the Pichia expression plasmid Zα-5601

Schematic diagram of the Pichia expression plasmid GAPZα-5601

Schematic diagram of the Pichia expression plasmid Zα-30640

Schematic diagram of the *Pichia* expression plasmid GAPZα-5102

**SDS-PAGE analysis of the expression of beet OxO in *P. pastoris*.** M: protein marker; M: protein marker; lanes 1-10, X-33 (ZαA-5102).

**SDS-PAGE analysis of the expression of beet OxO in *P. pastoris*.** M: protein marker; lanes 1-9, X-33(Zα-5601).

SDS-PAGE analysis of the expression of banana OxO in *P. pastoris*. M: protein marker; lanes 1-10, X-33(ZαA-30640).

SDS-PAGE analysis of the expression of beet OxO in *P. pastoris*. M: protein marker; lanes 1-9, X-33(GAPZα-5601).

PCR amplification of the OxO genes from cDNA library of sugar beet.
M. DNA Maker; Lane1-4, 5601 ; Lane5-8, 5102

PCR amplification of the OxO gene from cDNA library of banana.
M. DNA Maker; Lane1-3, 30640.

Schematic diagram of the plant expression vector

Histochemical assay of oxalate oxidase activity after overnight incubation in OxOx histological buffer Detection of OxO activity of the purified cell wall fraction from pea plants by colorimetric assay, pH 7.4. The left tube containing 2 mM oxalic acid; The right tube containing no oxalic acid.

Detection of OxOx activity of the purified 5102 fractions from pea plants.

Purification of recombinant beet OxOx 5102.
M, Protein Maker; lane1, Sample before purified by Q Sepharose column; Lane2, the washing sample; Lane3, eluted sample 13#; Lane4, eluted sample 14#; Lane5, eluted sample 15#.

Figure 23

SEQUENCE LISTING

<110> Nxt2b

<120> Method for producing oxalate oxidases

<130> P013552PCT1

<160> 24

<170> BiSSAP 1.2

<210> 1
<211> 696
<212> DNA
<213> Beta vulgaris subsp. vulgaris

<220>
<221> source
<222> 1..696
<223> /mol_type="unassigned DNA"
     /organism="Beta vulgaris subsp. vulgaris"

<400> 1
atggtctttg caatgagctt tacttctcat atttacgtgg cttcggcctc tgatcctggt      60
ctcctacagg attttttgtgt gggtgtaaat gaccctgatt cagcagtgtt tgtaaatgga     120
aaattctgca agaacccaaa agacgtgaca atcgacgatt tcttatacaa agggtttaat     180
attccctcag acacaaacaa cactcaaaga gcagaagcca cactagtaga tgtcaatcga     240
tttccagcac ttaacacatt aggtgtagcc atggctcgtg tagactttgc gtcctttggc     300

Figure 23 (Continued)

```
ctaaacacac ctcatttgca ccctcgtggt tctgagatat tcgcggtcct agaggggact   360
ttatatgccg gcattgtcac caccgataat aagcttttcg acacggtgtt gagaaagggt   420
gacatgattg ttttccctca aggcttaatc cacttccagc ttaatcttgg caagacagat   480
gctcttgcta ttgcctcttt tgggagccaa tttcctggac gagttaatgt tgctaatggt   540
gtctttggaa ctacgccaca aattttggat gatgtactta cccaagcgtt tcaggtagat   600
aagatggtga ttgagcaact tcgatctcag ttttcaggtc caaacacatc aatcaacact   660
ggaagatcta ttcttaaact cttaactgat gttgct                             696
```

<210> 2
<211> 232
<212> PRT
<213> Beta vulgaris subsp. vulgaris

<400> 2
Met Val Phe Ala Met Ser Phe Thr Ser His Ile Tyr Val Ala Ser Ala
1               5                   10                  15
Ser Asp Pro Gly Leu Leu Gln Asp Phe Cys Val Gly Val Asn Asp Pro
            20                  25                  30
Asp Ser Ala Val Phe Val Asn Gly Lys Phe Cys Lys Asn Pro Lys Asp
        35                  40                  45
Val Thr Ile Asp Asp Phe Leu Tyr Lys Gly Phe Asn Ile Pro Ser Asp
    50                  55                  60
Thr Asn Asn Thr Gln Arg Ala Glu Ala Thr Leu Val Asp Val Asn Arg
65                  70                  75                  80
Phe Pro Ala Leu Asn Thr Leu Gly Val Ala Met Ala Arg Val Asp Phe
                85                  90                  95
Ala Ser Phe Gly Leu Asn Thr Pro His Leu His Pro Arg Gly Ser Glu

Figure 23 (Continued)

```
                100             105             110
Ile Phe Ala Val Leu Glu Gly Thr Leu Tyr Ala Gly Ile Val Thr Thr
        115             120             125
Asp Asn Lys Leu Phe Asp Thr Val Leu Arg Lys Gly Asp Met Ile Val
    130             135             140
Phe Pro Gln Gly Leu Ile His Phe Gln Leu Asn Leu Gly Lys Thr Asp
145             150             155             160
Ala Leu Ala Ile Ala Ser Phe Gly Ser Gln Phe Pro Gly Arg Val Asn
            165             170             175
Val Ala Asn Gly Val Phe Gly Thr Thr Pro Gln Ile Leu Asp Asp Val
        180             185             190
Leu Thr Gln Ala Phe Gln Val Asp Lys Met Val Ile Glu Gln Leu Arg
        195             200             205
Ser Gln Phe Ser Gly Pro Asn Thr Ser Ile Asn Thr Gly Arg Ser Ile
    210             215             220
Leu Lys Leu Leu Thr Asp Val Ala
225             230
```

<210> 3
<211> 648
<212> DNA
<213> Beta vulgaris subsp. vulgaris

<220>
<221> source
<222> 1..648
<223> /mol_type="unassigned DNA"
    /organism="Beta vulgaris subsp. vulgaris"

<400> 3
tctgatcctg gtctcctaca ggatttttgt gtgggtgtaa atgaccctga ttcagcagtg    60
tttgtaaatg gaaaattctg caagaaccca aaagacgtga caatcgacga tttcttatac   120
aaagggttta atattccctc agacacaaac aacactcaaa gagcagaagc cacactagta   180

Figure 23 (Continued)

```
gatgtcaatc gatttccagc acttaacaca ttaggtgtag ccatggctcg tgtagacttt    240
gcgtcctttg gcctaaacac acctcatttg caccctcgtg gttctgagat attcgcggtg    300
ctagagggga ctttatatgc cggcattgtc accaccgatt acaagctttt cgacacggtg    360
ttgagaaagg gtgacatgat tgttttccct caaggcttaa tccacttcca gcttaatctt    420
ggcaagacag atgctcttgc tattgcctct tttgggagcc aatttcctgg acgagttaat    480
gttgctaatg gtgtctttgg aactacgcca caaattttgg atgatgtact tacccaagcg    540
tttcaggtag atgagatggt gattcagcaa cttcgatctc agttttcagg tcaaaacata    600
tcaatcaaca ctggaagatc tattcttaaa ctcttaactg atgttgct                648
```

<210> 4
<211> 216
<212> PRT
<213> Beta vulgaris subsp. vulgaris

<400> 4
Ser Asp Pro Gly Leu Leu Gln Asp Phe Cys Val Gly Val Asn Asp Pro
1               5                   10                  15
Asp Ser Ala Val Phe Val Asn Gly Lys Phe Cys Lys Asn Pro Lys Asp
            20                  25                  30
Val Thr Ile Asp Asp Phe Ile Tyr Lys Gly Phe Asn Ile Pro Ser Asp
        35                  40                  45
Thr Asn Asn Thr Gln Arg Ala Glu Ala Thr Leu Val Asp Val Asn Arg
    50                  55                  60
Phe Pro Ala Leu Asn Thr Leu Gly Val Ala Met Ala Arg Val Asp Phe
65                  70                  75                  80
Ala Ser Phe Gly Leu Asn Thr Pro His Leu His Pro Arg Gly Ser Glu
            85                  90                  95

Figure 23 (Continued)

Ile Phe Ala Val Leu Glu Gly Thr Leu Tyr Ala Gly Ile Val Thr Thr
        100              105              110

Asp Asn Lys Leu Phe Asp Thr Val Leu Arg Lys Gly Asp Met Ile Val
         115             120            125

Phe Pro Gln Gly Leu Ile His Phe Gln Leu Asn Leu Gly Lys Thr Asp
      130            135            140

Ala Leu Ala Ile Ala Ser Phe Gly Ser Gln Phe Pro Gly Arg Val Asn
145            150            155            160

Val Ala Asn Gly Val Phe Gly Thr Thr Pro Gln Ile Leu Asp Asp Val
        165            170            175

Leu Thr Gln Ala Phe Gln Val Asp Glu Met Val Ile Gln Gln Leu Arg
        180            185            190

Ser Gln Phe Ser Gly Pro Asn Thr Ser Ile Asn Thr Gly Arg Ser Ile
      195            200            205

Leu Lys Leu Leu Thr Asp Val Ala
   210            215

<210> 5

<211> 648

<212> DNA

<213> Beta vulgaris subsp. vulgaris

<220>

<221> source

<222> 1..648

<223> /mol_type="unassigned DNA"
   /organism="Beta vulgaris subsp. vulgaris"

<400> 5
tccgatcctg caccccttca agatttttgt attgctgtaa atgatcccaa ttctgcagtg    60
cttgtgaatg gaaagctttg taagaaccca aaagaagtga caatagatga tttcttgtac   120
aaagggttta atatacctgc agacacaaac aacactcaag gagcaagtgc cacactagtg   180
gacattactc tattccctgc agttaacaca caaggagtct ccatggctcg tgtggacttt   240

Figure 23 (Continued)

```
gcgccatttg gactaaacac ccctcattta catcctcgtg gctcagaggt tttcgcagtg    300
atggaaggga ttatgtatgc tggttttgtg accactgatt ataagctcta tgatacaatt    360
ataaaaaagg gtgatattat tgtgtttcca caaggtctaa ttcatttcca acttaatctt    420
gggaagacag atgctttagc aattgcctca tttgggagcc aaaatccagg gagaattaat    480
atcgctgaca gtgtgtttgg tactactccg cgtgttctag atgatgtgct taccaaagga    540
tttcaaatcg atgagttgtt ggtcaagcaa cttcgttctc agttttctac tgataatata    600
tcaacaagca ctggaaggtc atttttgaaa ttgctatctg aaacttat                 648
```

<210> 6
<211> 216
<212> PRT
<213> Beta vulgaris subsp. vulgaris

<400> 6
Ser Asp Pro Ala Pro Leu Gln Asp Phe Cys Ile Ala Val Asn Asp Pro
1               5                   10                  15
Asn Ser Ala Val Leu Val Asn Gly Lys Leu Cys Lys Asn Pro Lys Glu
            20                  25                  30
Val Thr Ile Asp Asp Phe Leu Tyr Lys Gly Phe Asn Ile Pro Ala Asp
        35                  40                  45
Thr Asn Asn Thr Gln Gly Ala Ser Ala Thr Leu Val Asp Ile Thr Leu
    50                  55                  60
Phe Pro Ala Val Asn Thr Gln Gly Val Ser Met Ala Arg Val Asp Phe
65                  70                  75                  80
Ala Pro Tyr Gly Leu Asn Thr Pro His Leu His Pro Arg Gly Ser Glu
                85                  90                  95
Val Phe Ala Val Met Glu Gly Ile Met Tyr Ala Gly Phe Val Thr Thr

Figure 23 (Continued)

```
                100             105             110
Asp Tyr Lys Leu Tyr Asp Thr Ile Ile Lys Lys Gly Asp Ile Ile Val
        115             120             125
Phe Pro Gln Gly Leu Ile His Phe Gln Leu Asn Leu Gly Lys Thr Asp
    130             135             140
Ala Leu Ala Ile Ala Ser Phe Gly Ser Gln Asn Pro Gly Arg Ile Asn
145             150             155             160
Ile Ala Asp Ser Val Phe Gly Thr Thr Pro Arg Val Leu Asp Asp Val
            165             170             175
Leu Thr Lys Gly Phe Gln Ile Asp Glu Leu Leu Val Lys Gln Leu Arg
            180             185             190
Ser Gln Phe Ser Thr Asp Asn Ile Ser Thr Ser Thr Gly Arg Ser Phe
        195             200             205
Leu Lys Leu Leu Ser Glu Thr Tyr
    210             215
```

<210> 7
<211> 639
<212> DNA
<213> Musa acuminata

<220>
<221> source
<222> 1..639
<223> /mol_type="unassigned DNA"
    /organism="Musa acuminata"

<400> 7
tttgatccga gtcctctcca agactttttgc gttgctgact acgactccaa cgtgtttgtg       60
aacggattcg cctgcaagaa agctaaggat gtcacggcag atgacttcta cttcaccggc      120
ttagacaagc ccgcgagcac cgccaacgag cttggcgcaa acatcactct cgtcaacgtg      180
gaacgactcc caggcctcaa ctcccttggc gtcgccatgt ctcgcatcga ctacgcgccc      240

Figure 23 (Continued)

```
ttcggtctca accctcctca ctcgcatcca cgatcgtcgg agatactgca cgtggcggaa    300
ggaacgctct acgccggctt cgtcacctcc aacacggaaa acggcaacct tctcttcgct    360
aagaagctga agaagggcga cgcgtttgtg ttccccaggg gcctcataca cttccagttc    420
aacatcgggg acaccgatgc ggtggcgttc gctaccttcg gcagccagag cccgggtctc    480
gtcaccaccg ccaacgcact gttcggatcg aagccgccca tcgctgatta cattcttgcc    540
caggccgtgc agcttagcaa gacgaccgtg ggctggcttc agcagcagca gtggttggac    600
atcgctcaag aatatggaca acgcttagtt caagctaat                           639
```

<210> 8
<211> 213
<212> PRT
<213> Musa acuminata

<400> 8

```
Phe Asp Pro Ser Pro Leu Gln Asp Phe Cys Val Ala Asp Tyr Asp Ser
1               5                  10                  15
Asn Val Phe Val Asn Gly Phe Ala Cys Lys Lys Ala Lys Asp Val Thr
            20                  25                  30
Ala Asp Asp Phe Tyr Phe Thr Gly Leu Asp Lys Pro Ala Ser Thr Ala
        35                  40                  45
Asn Glu Leu Gly Ala Asn Ile Thr Leu Val Asn Val Glu Arg Leu Pro
    50                  55                  60
Gly Leu Asn Ser Leu Gly Val Ala Met Ser Arg Ile Asp Tyr Ala Pro
65                  70                  75                  80
Phe Gly Leu Asn Pro Pro His Ser His Pro Arg Ser Ser Glu Ile Leu
                85                  90                  95
His Val Ala Glu Gly Thr Leu Tyr Ala Gly Phe Val Thr Ser Asn Thr
            100                 105                 110
```

Figure 23 (Continued)

```
Glu Asn Gly Asn Leu Leu Phe Ala Lys Lys Leu Lys Lys Gly Asp Ala
        115                 120                 125
Phe Val Phe Pro Arg Gly Leu Ile His Phe Gln Phe Asn Ile Gly Asp
    130                 135                 140
Thr Asp Ala Val Ala Phe Ala Thr Phe Gly Ser Gln Ser Pro Gly Leu
145                 150                 155                 160
Val Thr Thr Ala Asn Ala Leu Phe Gly Ser Lys Pro Pro Ile Ala Asp
            165                 170                 175
Tyr Ile Leu Ala Gln Ala Val Gln Leu Ser Lys Thr Thr Val Gly Trp
        180                 185                 190
Leu Gln Gln Gln Gln Trp Leu Asp Ile Ala Gln Glu Tyr Gly Gln Arg
    195                 200                 205
Leu Val Gln Ala Asn
   210
```

<210> 9
<211> 639
<212> DNA
<213> Beta vulgaris subsp. vulgaris

<220>
<221> source
<222> 1..639
<223> /mol_type="unassigned DNA"
/organism="Beta vulgaris subsp. vulgaris"

<400> 9

| | |
|---|---|
| atggctcccc tactctacct tgtagtattc ttgcttgctc cttttctctc ccatgctgcg | 60 |
| gatcccgatc ctttgctaga ttttgtgta gcggaccta atgcctctcc ctcatttgct | 120 |
| aatttccctt gcaaacaaac ctcaaatgtg acctctgaag atttcttctt tgatgggttt | 180 |
| atgaatgagg gaaacacatc aaactcgttt ggatcaaggg tcacacccgg aaacgtcctc | 240 |
| acatttcctg cccttaatat gctcgggatt tcaatgaatc gggttgatct tgctgtggat | 300 |

Figure 23 (Continued)

```
gggatgaacc cgccccattc ccacccacga gcaagtgaga gcggtgtggt gatgaagggg    360
agagttctag tagggttcgt aaccacgggg aatgtgtact attcaaaggt gttggttcca    420
ggacagatgt ttgtaatccc aaggggggttg gttcattttc aaaagaatgt tggacaaaat   480
aaggcactca tcattacagc tttcaatagt cagaatccag gagtagtgtt attatcctca    540
accctgtttg gtacaaaccc ttcaattcca gatgatgttt taagccaaac tttcctagtg    600
gaccagagca ttgtcgaagg aataaaatcc aactttga                            639
```

<210> 10
<211> 212
<212> PRT
<213> Beta vulgaris subsp. vulgaris

<400> 10
Met Ala Pro Leu Leu Tyr Leu Val Val Phe Leu Leu Ala Pro Phe Leu
1               5                   10                  15
Ser His Ala Ala Asp Pro Asp Pro Leu Leu Asp Phe Cys Val Ala Asp
            20                  25                  30
Leu Asn Ala Ser Pro Ser Phe Ala Asn Phe Pro Cys Lys Gln Thr Ser
        35                  40                  45
Asn Val Thr Ser Glu Asp Phe Phe Phe Asp Gly Phe Met Asn Glu Gly
    50                  55                  60
Asn Thr Ser Asn Ser Phe Gly Ser Arg Val Thr Pro Gly Asn Val Leu
65                  70                  75                  80
Thr Phe Pro Ala Leu Asn Met Leu Gly Ile Ser Met Asn Arg Val Asp
            85                  90                  95
Leu Ala Val Asp Gly Met Asn Pro Pro His Ser His Pro Arg Ala Ser
            100                 105                 110
Glu Ser Gly Val Val Met Lys Gly Arg Val Leu Val Gly Phe Val Thr

Figure 23 (Continued)

```
            115              120              125
Thr Gly Asn Val Tyr Tyr Ser Lys Val Leu Val Pro Gly Gln Met Phe
       130              135              140
Val Ile Pro Arg Gly Leu Val His Phe Gln Lys Asn Val Gly Gln Asn
145              150              155              160
Lys Ala Leu Ile Ile Thr Ala Phe Asn Ser Gln Asn Pro Gly Val Val
                165              170              175
Leu Leu Ser Ser Thr Leu Phe Gly Thr Asn Pro Ser Ile Pro Asp Asp
           180              185              190
Val Leu Ser Gln Thr Phe Leu Val Asp Gln Ser Ile Val Glu Gly Ile
      195              200              205
Lys Ser Asn Phe
  210
```

<210> 11
<211> 660
<212> DNA
<213> Beta vulgaris subsp. vulgaris

<220>
<221> source
<222> 1..660
<223> /mol_type="unassigned DNA"
    /organism="Beta vulgaris subsp. vulgaris"

<400> 11
atggaagtcg tcgcagctgt atcttttctg gccgtgttat tggctctggt ttcccctgcc    60
ctcgccaatg atcctgatat gctccaagat gtttgtgtcg ctgattccac ctctggagtg    120
aaattgaatg gatttgcatg caaggatgca gcaagcatta caccagaaga cttcttcttt    180
gctggaatat ccaaacccgg aatgacaaac aatacaatga atccctagt aaccggagct    240 aacgtcgaaa agataccggg tttaaacaca ctcggagtgt ccatgggtcg tatcgacttc    300
```

Figure 23 (Continued)

ggcccaggtg gtcttaaccc acctcacact cacccacgag ccacagaaat ggtctttgtg   360
ttatatggag aattggacgt tggtttccta actacttcta ataagctcat ttctaagcat   420
attaaaactg gtgaaacttt tgtttttcct agagggttag tccactttca gaaaaataat   480
ggggataaac ctgctgcttt agtcactgct tttaatagtc agttgcctgg cacccaatca   540
atagctgcca cgttgtttac gtcgacccca cctgttccag ataatgtttt aactatgact   600
ttccaagtcg gtactaaaca agtccagaag atcaaggcta ggctcgctcc taagaagtaa   660

<210> 12
<211> 219
<212> PRT
<213> Beta vulgaris subsp. vulgaris

<400> 12
Met Glu Val Val Ala Ala Val Ser Phe Leu Ala Val Leu Leu Ala Leu
1               5                   10                  15
Val Ser Pro Ala Leu Ala Asn Asp Pro Asp Met Leu Gln Asp Val Cys
            20                  25                  30
Val Ala Asp Ser Thr Ser Gly Val Lys Leu Asn Gly Phe Ala Cys Lys
        35                  40                  45
Asp Ala Ala Ser Ile Thr Pro Glu Asp Phe Phe Phe Ala Gly Ile Ser
    50                  55                  60
Lys Pro Gly Met Thr Asn Asn Thr Met Lys Ser Leu Val Thr Gly Ala
65                  70                  75                  80
Asn Val Glu Lys Ile Pro Gly Leu Asn Thr Leu Gly Val Ser Met Gly
            85                  90                  95
Arg Ile Asp Phe Gly Pro Gly Gly Leu Asn Pro Pro His Thr His Pro
            100                 105                 110
Arg Ala Thr Glu Met Val Phe Val Leu Tyr Gly Glu Leu Asp Val Gly
        115                 120                 125

Figure 23 (Continued)

Phe Leu Thr Thr Ser Asn Lys Leu Ile Ser Lys His Ile Lys Thr Gly
    130                135                140
Glu Thr Phe Val Phe Pro Arg Gly Leu Val His Phe Gln Lys Asn Asn
145                150                155                160
Gly Asp Lys Pro Ala Ala Leu Val Thr Ala Phe Asn Ser Gln Leu Pro
         165                170                175
Gly Thr Gln Ser Ile Ala Ala Thr Leu Phe Thr Ser Thr Pro Pro Val
        180                185                190
Pro Asp Asn Val Leu Thr Met Thr Phe Gln Val Gly Thr Lys Gln Val
     195                200                205
Gln Lys Ile Lys Ala Arg Leu Ala Pro Lys Lys
   210                 215

<210> 13
<211> 669
<212> DNA
<213> Beta vulgaris subsp. vulgaris

<220>
<221> source
<222> 1..669
<223> /mol_type="unassigned DNA"
    /organism="Beta vulgaris subsp. vulgaris"

<400> 13
atggcggctg tttgggtagt cttggtggtg ctagcggcgg cttttgctgt tggggtcttt    60
gccagcgatc ctgatatgct tcaagatgtt tgtgttgctg atcgtacatc tggaatatta   120
gtgaatggat tcacatgtaa aaatatgacc atgataaccc ctgaagactt cttcttcacc   180
ggaatttcac aaccaggcca atcacaaat aaaatccttg gttctcgagt caccggagcg   240
aatgtgcagg acatccctgg tctcaacacc ttgggagtct cgatggctcg tgtcgactt   300 actccctacg gtctaaaccc acctcacatt caccctagaa tcgtccaccc tcgtgccact   360

Figure 23 (Continued)

gaaatgatct atgttcttaa gggtgaattg tacgttggtt ttataacgac cgacaataag    420
ctcatttcca aggttgttaa agctggagaa gtatttgttt tccctagagg tttggctcac    480
tttcagaaaa acatgttgaa atatccagct gctgcattag ctgccttcaa cagccaactt    540
ccaggcactc aacaatttgc agctgctctc tttacttcca atcctcctgt gtctaatgat    600
gtgttggctc aggcttttaa cattgacgaa cacaatgtca aaagattag gctggccttt    660 actccatag                                                            669

<210> 14
<211> 217
<212> PRT
<213> Beta vulgaris subsp. vulgaris

<400> 14
Met Ala Ala Val Trp Val Val Leu Val Val Leu Ala Ala Ala Phe Ala
1               5                   10                  15
Val Gly Val Phe Ala Ser Asp Pro Asp Met Leu Gln Asp Val Cys Val
            20                  25                  30
Ala Asp Arg Thr Ser Gly Ile Leu Val Asn Gly Phe Thr Cys Lys Asn
        35                  40                  45
Met Thr Met Ile Thr Pro Glu Asp Phe Phe Phe Thr Gly Ile Ser Gln
    50                  55                  60
Pro Gly Gln Ile Thr Asn Lys Ile Leu Gly Ser Arg Val Thr Gly Ala
65                  70                  75                  80
Asn Val Gln Asp Ile Pro Gly Leu Asn Thr Leu Gly Val Ser Met Ala
                85                  90                  95
Arg Val Asp Phe Thr Pro Tyr Gly Leu Asn Pro Pro His Ile His Pro
            100                 105                 110
Arg Ala Thr Glu Met Ile Tyr Val Leu Lys Gly Glu Leu Tyr Val Gly

Figure 23 (Continued)

```
            115                 120                 125
Phe Ile Thr Thr Asp Asn Lys Leu Ile Ser Lys Val Val Lys Ala Gly
        130                 135                 140
Glu Val Phe Val Phe Pro Arg Gly Leu Ala His Phe Gln Lys Asn Met
    145                 150                 155                 160
Leu Lys Tyr Pro Ala Ala Ala Leu Ala Ala Phe Asn Ser Gln Leu Pro
                165                 170                 175
Gly Thr Gln Gln Phe Ala Ala Ala Leu Phe Thr Ser Asn Pro Pro Val
            180                 185                 190
Ser Asn Asp Val Leu Ala Gln Ala Phe Asn Ile Asp Glu His Asn Val
                195                 200                 205
Lys Lys Ile Arg Ala Gly Leu Thr Pro
    210                 215
```

<210> 15
<211> 660
<212> DNA
<213> Musa acuminata

<220>
<221> source
<222> 1..660
<223> /mol_type="unassigned DNA"
    /organism="Musa acuminata"

<400> 15
atggagtcgc actacacgaa gagaccattc ctcctctttc tctccttcac cgtcctcctc    60
gtgttgatcc gcgctgaccc tgatcctctc caggacttct gcgtcgccga cctcggagct    120
actgtggtcg tcaatgggtt cccgtgcaag cccgcgtccg gagtcacgtc cgacgacttc    180
ttcttcgccg gactgtccag ggagggcaac accagcaata tcttcgggtc caacgtgacc    240
aacgccaaca tgctcagctt cccggggctc aacaccctcg gcgtctccat gaaccgcgtc    300

Figure 23 (Continued)

```
gacgtcgccc ccggcggcac caacccgccc cacagccacc cgagggctac cgagctcatc    360
atcctcctca agggccggct gctggtgggg ttcatcagca ccagtaacca gttcttctcc    420
aaggtcttga accccggcga gatgttcgtg gtgcccaagg ggctcatcca cttccagtac    480
aacgtcggca aggagaaggc gctcgccatc accaccttcg acagccagct ccccggagta    540
gtgatcgcct ccaccaccct gttcgcatcg aatccggcga ttcccgacga tgtgctggcc    600
aaagcttttc aggtggacgc gaaggtcgtc gctctcatca agtccaagtt tgagagataa   660
```

<210> 16
<211> 219
<212> PRT
<213> Musa acuminata

<400> 16
Met Glu Ser His Tyr Thr Lys Arg Pro Phe Leu Leu Phe Leu Ser Phe
1               5                   10                  15
Thr Val Leu Leu Val Leu Ile Arg Ala Asp Pro Asp Pro Leu Gln Asp
            20                  25                  30
Phe Cys Val Ala Asp Leu Gly Ala Thr Val Val Val Asn Gly Phe Pro
        35                  40                  45
Cys Lys Pro Ala Ser Gly Val Thr Ser Asp Asp Phe Phe Phe Ala Gly
    50                  55                  60
Leu Ser Arg Glu Gly Asn Thr Ser Asn Ile Phe Gly Ser Asn Val Thr
65                  70                  75                  80
Asn Ala Asn Met Leu Ser Phe Pro Gly Leu Asn Thr Leu Gly Val Ser
            85                  90                  95
Met Asn Arg Val Asp Val Ala Pro Gly Gly Thr Asn Pro Pro His Ser
            100                 105                 110
His Pro Arg Ala Thr Glu Leu Ile Ile Leu Leu Lys Gly Arg Leu Leu
        115                 120                 125

Figure 23 (Continued)

Val Gly Phe Ile Ser Thr Ser Asn Gln Phe Phe Ser Lys Val Leu Asn
   130           135           140

Pro Gly Glu Met Phe Val Val Pro Lys Gly Leu Ile His Phe Gln Tyr
145           150           155           160

Asn Val Gly Lys Glu Lys Ala Leu Ala Ile Thr Thr Phe Asp Ser Gln
       165           170           175

Leu Pro Gly Val Val Ile Ala Ser Thr Thr Leu Phe Ala Ser Asn Pro
   180           185           190

Ala Ile Pro Asp Asp Val Leu Ala Lys Ala Phe Gln Val Asp Ala Lys
    195          200           205

Val Val Ala Leu Ile Lys Ser Lys Phe Glu Arg
  210         215

<210> 17
<211> 36
<212> DNA
<213> Artificial Sequence

<220>
<221> source
<222> 1..36
<223> /mol_type="unassigned DNA"
   /note="Primer 510F"
   /organism="Artificial Sequence"

<400> 17
ccgctcgaga aaagatctga tcctggtctc ctacag                    36

<210> 18
<211> 37
<212> DNA
<213> Artificial Sequence

<220>
<221> source

Figure 23 (Continued)

<222> 1..37
<223> /mol_type="unassigned DNA"
    /note="Primer 510R"
    /organism="Artificial Sequence"

<400> 18
aaatatgcgg ccgctcaagc aacatcagtt aagagtt                37

<210> 19
<211> 33
<212> DNA
<213> Artificial Sequence

<220>
<221> source
<222> 1..33
<223> /mol_type="unassigned DNA"
    /note="Primer 560F"
    /organism="Artificial Sequence"

<400> 19
ccgctcgaga aaagatccga tcctgcaccc ctt                33

<210> 20
<211> 39
<212> DNA
<213> Artificial Sequence

<220>
<221> source
<222> 1..39
<223> /mol_type="unassigned DNA"
    /note="Primer 5601R"
    /organism="Artificial Sequence"

Figure 23 (Continued)

<400> 20
aaatatgcgg ccgctcaata agtttcagat agcaatttc        39

<210> 21
<211> 35
<212> DNA
<213> Artificial Sequence

<220>
<221> source
<222> 1..35
<223> /mol_type="unassigned DNA"
    /note="Primer 30640F"
    /organism="Artificial Sequence"

<400> 21
ccgctcgaga aaagatttga tccgagtcct ctcca        35

<210> 22
<211> 38
<212> DNA
<213> Artificial Sequence

<220>
<221> source
<222> 1..38
<223> /mol_type="unassigned DNA"
    /note="Primer 30640R"
    /organism="Artificial Sequence"

<400> 22
aaatatgcgg ccgctcaatt agcttgaact aagcgttg        38

Figure 23 (Continued)

<210> 23
<211> 5900
<212> DNA
<213> Artificial Sequence

<220>
<221> source
<222> 1..5900
<223> /mol_type="unassigned DNA"
/note="pET-32a(+) plasmid sequence"
/organism="Artificial Sequence"

<400> 23

| | | |
|---|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta atcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta taagggattt tgccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg agacaataac cctgataaat gcttcaataa tattgaaaaa ggaagagtat | 600 |
| gagtattcaa catttccgtg tcgcccttat ccctttttt gcggcatttt gccttcctgt | 660 |

Figure 23 (Continued)

ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt tttttctgcg cgtaatctgc tgcttgcaaa caaaaaaacc    1680

Figure 23 (Continued)

accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac gggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760

Figure 23 (Continued)

tgagtttctc cagaagcgtt aatgtctggc ttctgataaa gcgggccatg ttaagggcgg    2820 tttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840

Figure 23 (Continued)

cccagcaggc gaaaatcctg tttgatggtg gttaacggcg ggatataaca tgagctgtct    3900
tcggtatcgt cgtatcccac taccgagatg tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920

Figure 23 (Continued)

gcccaacagt cccccggcca cggggcctgc caccatacccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacatat gagcgataaa    5220
attattcacc tgactgacga cagttttgac acggatgtac tcaaagcgga cggggcgatc    5280
ctcgtcgatt tctgggcaga gtggtgcggt ccgtgcaaaa tgatcgcccc gattctggat    5340
gaaatcgctg acgaatatca gggcaaactg accgttgcaa aactgaacat cgatcaaaac    5400
cctggcactg cgccgaaata tggcatccgt ggtatcccga ctctgctgct gttcaaaaac    5460
ggtgaagtgg cggcaaccaa agtgggtgca ctgtctaaag gtcagttgaa agagttcctc    5520
gacgctaacc tggccggttc tggttctggc catatgcacc atcatcatca tcattcttct    5580
ggtctggtgc cacgcggttc tggtatgaaa gaaaccgctg ctgctaaatt cgaacgccag    5640
cacatggaca gcccagatct gggtaccgac gacgacgaca aggccatggc tgatatcgga    5700
tccgaattcg agctccgtcg acaagcttgc ggccgcactc gagcaccacc accaccacca    5760
ctgagatccg gctgctaaca aagcccgaaa ggaagctgag ttggctgctg ccaccgctga    5820
gcaataacta gcataacccc ttggggcctc taaacgggtc ttgagggggtt ttttgctgaa    5880 aggaggaact atatccggat                                                5900

<210> 24
<211> 5423

Figure 23 (Continued)

<212> DNA
<213> Artificial Sequence

<220>
<221> source
<222> 1..5423
<223> /mol_type="unassigned DNA"
     /note="pAT plasmid"
     /organism="Artificial Sequence"

<400> 24

| | | | | |
|---|---|---|---|---|
| tggcgaatgg | gacgcgccct | gtagcggcgc | attaagcgcg gcgggtgtgg tggttacgcg | 60 |
| cagcgtgacc | gctacacttg | ccagcgccct | agcgcccgct cctttcgctt tcttcccttc | 120 |
| ctttctcgcc | acgttcgccg | gctttccccg | tcaagctcta aatcggggggc tccctttagg | 180 |
| gttccgattt | agtgctttac | ggcacctcga | ccccaaaaaa cttgattagg gtgatggttc | 240 |
| acgtagtggg | ccatcgccct | gatagacggt | ttttcgccct ttgacgttgg agtccacgtt | 300 |
| ctttaatagt | ggactcttgt | tccaaactgg | aacaacactc aaccctatct cggtctattc | 360 |
| ttttgattta | taagggattt | tgccgatttc | ggcctattgg ttaaaaaatg agctgattta | 420 |
| acaaaaattt | aacgcgaatt | ttaacaaaat | attaacgttt acaatttcag gtggcacttt | 480 |
| tcggggaaat | gtgcgcggaa | cccctatttg | tttatttttc taaatacatt caaatatgta | 540 |
| tccgctcatg | agacaataac | cctgataaat | gcttcaataa tattgaaaaa ggaagagtat | 600 |
| gagtattcaa | catttccgtg | tcgcccttat | tcccttttt gcggcatttt gccttcctgt | 660 |
| ttttgctcac | ccagaaacgc | tggtgaaagt | aaaagatgct gaagatcagt tgggtgcacg | 720 |

Figure 23 (Continued)

agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800

Figure 23 (Continued)

ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac gggggggttcg tgcacacagc ccagcttgga   1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttttt tacggttcct ggccttttgc tggccttttg ctcacatgtt   2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg     2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820 tttttcctg tttggtcact gatgcctccg tgtaaggggg atttctgttc atgggggtaa    2880

Figure 23 (Continued)

tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagatg tccgcaccaa cgcgcagccc ggactcggta    3960

Figure 23 (Continued)

atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620 tttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040

Figure 23 (Continued)

aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacccat ggctgatatc    5220
ggatccgaat tcgagctccg tcgacaagct tgcggccgca ctcgagcacc accaccacca    5280
ccactgagat ccggctgcta acaaagcccg aaaggaagct gagttggctg ctgccaccgc    5340
tgagcaataa ctagcataac cccttggggc ctctaaacgg gtcttgaggg gttttttgct    5400
gaaaggagga actatatccg gat                                          5423

METHODS OF TREATMENT USING RECOMBINANT OXALATE OXIDASE

FIELD OF THE INVENTION

The present invention relates to the treatment of oxalate-related diseases and provides oxalate oxidases (OxOx) that have suitable activity near physiological pH (7.4). The properties of these OxOx make them potential drug candidates for use in reducing oxalate concentration in patients suffering from excess of oxalate. Especially due to the high activity at physiological pH, the OxOx's are suitable drug candidates for parenteral administration, i.e. to reduce the oxalate concentration in the plasma.

BACKGROUND OF THE INVENTION

Kidney/urinary tract stone disease (urolithiasis) is a major health problem throughout the world. Most of the stones associated with urolithiasis are composed of calcium oxalate alone or calcium oxalate plus calcium phosphate.

Many disease states are associated with an excess quantity of oxalate in the body including: primary hyperoxaluria, secondary hyperoxaluria, autism, vulvodynia, oxalosis associated with end-stage renal disease, cardiac conductance disorders, Crohn's disease, inflammatory bowel disease, colitis, urolithiasis, oxalosis associated with end-stage renal disease, sarcoidosis, asthma, COPD, fibromyalgia, Zellweger syndrome, bariatric surgery and other enteric disease states.

Oxalate may be absorbed through the whole gastrointestinal tract including the stomach, and the small and large intestines. Therefore removal of dietary oxalate in these organs is effective in preventing oxalate absorption. Absorption of dietary oxalate contributes to 10-70% of urinary oxalate secretion. It is believed that excess of concentrations of calcium oxalate is responsible for stone formation. Thus, by reducing the oxalate concentration the risk of stone formation will be decreased.

There are very few, if any, treatment strategies known to significantly decrease the risk of stone formation. The main approaches have been to limit dietary oxalate absorption by orally administering oxalate degrading enzymes or bacteria, which come into contact with the content of the stomach and the intestines. The challenge in providing such treatment is the harsh acidic stomach environment, which may degrade the enzyme so that it becomes ineffective at low pH and in a high pepsin activity environment. The intestines are also challenging due to the presence of trypsin and chymotrypsin and due to a pH approaching neutral pH. Most of the known oxalate degrading enzymes have activity optimum at pH at an acidic pH. The challenge when oxalate degrading bacteria are used is to pass the gastric environment without losing the activity of the bacteria and to have the bacteria colonized in the intestines. An attempt has been to orally administer an enteric coated composition.

All germ-like oxalate oxidases reported in the literature are acid active and oxalate oxidase reported with activity at pH greater than 7 has not been confirmed as a single purified protein with gene sequence. WO 2011/066282 describes oxalate-degrading enzymes derived from fungi. Examples 5 of WO 2011/066282 has not isolated the enzyme and no information about the protein sequence is given. The present inventors have tried to purify some of this enzyme, but failed.

Makoto K. et al. in Journal of the Institute of Brewing, vol 115, 2009, 232-237 describes enzymes derived from barley and malt, but conclude that the enzyme seems to be a flavoprotein (see page 235, $1^{st}$ column). The present inventors have repeated the experiment described in Makoto et al. using exactly the same barley seed, but failed to find any oxidase activity at pH 7.4.

However, there is still a need for treatment strategies, which effectively reduces the oxalate concentration in the body.

DESCRIPTION OF THE INVENTION

The present invention provides a novel treatment strategy for decreasing the concentration of oxalate in the body. The strategy is based on the finding of oxalate oxidases that have optimum or sufficient activity at pH 7.4 and thus, are capable of reducing oxalate concentration in the blood after parenteral administration. By using the parenteral administration route problems relating to degradation of the enzymes in the gastrointestinal tract combined with the necessity of having a pH, where the enzyme is active are avoided. However, a prerequisite for the treatment strategy is that the enzyme(s) is (are) active at physiological pH (pH 7.4). Until now only one oxalate oxidase has been described, which has some activity at pH 7.4 and that is an oxalate oxidase activity associated with plant solid tissue from *Bougainvillea spectabilis* leaves (Biochem. J., 1962, 85, 33).

The present invention also relates to oxalate oxidases (or variants thereof) with sufficient activity about pH 7.5 as well as the polynucleotides encoding the variants. The invention also relates to a recombinant host cell comprising the polynucleotides as well as a method for producing the oxalate oxidases variants. Especially, the invention relates to recombinant oxalate oxidases which have a sufficient activity at pH 7.5, i.e. they are capable of degrading oxalate at pH 7.4 such that the relative activity is at least 20%. The relative activity is calculated as (observed activity (pH 7.5)/max. activity)* 100%. One unit of activity is defined as the enzyme amount required to produce 1 μmole of formate from oxalate under the conditions described in Example 6 herein.

As seen from the examples herein recombinant oxalate oxidases have been produced, which have a relative activity at pH 7.5 of at least 60%. In particular, oxalate oxidases with a relative activity of at least 80% or at least 90% have been produced. To this end it is important to note that this finding is unique as no oxalate oxidase has been disclosed with such an activity at pH 7.5 (range pH 7.0-8.0). Most oxalate oxidases described have max. activity at acidic pH. The oxalate oxidases having a suitable relative activity at pH 7.5 or in the range of pH 7.0-8.0 are all based on the finding of oxalate oxidases from specific plant material, where the oxalate oxidases surprisingly are found to have activity at neutral/basic pH. As seen from the table in the Examples, many different plants from a variety of plant families have been tested and only a few of them gave a positive result with respect to activity at pH 7-8.

An important consequence of this finding is the possibility of developing a therapeutic recombinant oxalate oxidase suitable for use in the treatment of diseases relating to excess of oxalate as described herein. Especially the finding opens up for a novel approach, namely i) administration by the parenteral route (i.e. degradation of oxalate in the plasma/blood) or ii) administration by the oral route using enteric coated material and delivery the recombinant enzymes to the intestines, where pH is about 6-8, i.e. at a pH where the oxalate oxidases have a suitable activity.

The invention also relates to the use of the novel oxalate oxidase variants for the treatment or prophylaxis of oxalate-related diseases and to compositions comprising the oxalate oxidase variants.

Patients with severe oxalate situations. Urinary and plasma oxalate originates from two sources: liver synthesis and dietary absorption and is removed mainly by kidney. Under certain disease conditions, including primary hyperoxaluria (PH) (1-4), secondary hyperoxaluria (SH) (5-7), Zellweger spectrum disorders (ZSD) (8), and chronic renal failure (CRF) or end-stage renal failure (ESRF) (9-11), urinary oxalate and plasma oxalate concentrations can increase to very high concentrations, which cause severe oxalate related diseases.

PH, including type I, II and III, are rare genetic disorders of glyoxylate metabolism in which specific hepatic enzyme deficiencies result in oxalate overproduction in the liver. Type I pertains to lack of hepatic alanine: glyoxylate aminotransferase (AGT) and type II to lack of glyoxylate/hydroxypyruvate reductase (GR/HPR) (2). PH type III results from defects in the liver-specific mitochondrial enzyme 4-hydroxy-2-oxo-glutarate aldolase (HOGA). There is another type of PH, referred to as non-I or non-II, which shows a similar phenotype as PH, but which has the above mentioned enzymes represented in the liver (1). PH is the most severe form of hyperoxaluria and patients suffering from PH can produce plasma oxalate concentrations greater than 100 µmol/L if chronic or end-stage renal failure has been developed (3, 9). CaOx supersaturation in the blood of PH patients will lead to systemic oxalosis: CaOx crystals depositing in multiple organs including kidneys, thyroid, myocardium, bone, skin, vessels and eyes. Deposition of CaOx crystals and high concentrations of oxalate in the kidneys will ultimately lead to ESRF and death if untreated (12).

ZSD patients have high incidence rates (83%) of hyperoxaluria (8). ZSD is characterized by a general loss of peroxisomal functions caused by deficient peroxisomal assembly. Although the mechanism of oxalate synthesis in ZSD patients is unclear, the levels of urinary oxalate in some ZSD patients are comparable to PH patients.

Secondary hyperoxaluria (SH) is caused by over-absorption of dietary oxalate or oxalate precursors either due to gastrointestinal (GI) diseases, such as inflammatory bowel diseases (IBD), cystic fibrosis (CF), short bowel syndrome and bariatric surgery, or ingestion of a diets rich in oxalate or oxalate precursors (6, 13, 14). SH is very common and generally less severe than PH, but high urinary and plasma oxalate concentrations can occur in these cases due to consumption of rich oxalate diets, large ingested doses of vitamin C (an oxalate precursor), or in patients with chronic or end-stage renal failure (6, 13, 14).

CRF and ESRF patients under chronic hemodialysis are likely to develop hyperoxaluria (9-11). The kidneys of these patients in combination with hemodialysis are unable to eliminate oxalate sufficiently, due to complications of CRF or ESRF. In addition, vitamin C is often injected intravenously as an antioxidant during hemodialysis, which is later metabolized to oxalate in the human body (15). Plasma oxalate concentrations in these patients can be found between 30-90 µmol/L. In 2006, there were 345,000 patients under hemodialysis in the United States (16) and this number is on the rise. Hence, the number of patients with the risk of oxalosis is significant.

Toxic effects of high concentrations of oxalate and CaOx. Supersaturation of CaOx in blood can lead to oxalosis. CaOx crystals deposited in multiple organs in PH patients have been widely observed (2, 12) and CaOx crystals deposited in organs in SH patients (15, 17-20) and patients who undergo chronic hemodialysis have also been reported in many cases (11,21-23). Deposition of CaOx crystals in these organs can result in organ dysfunction. Primary and secondary oxalosis are often one of the critical factors affecting the outcome of transplanted organs (11, 24-26). Many cases of transplant dysfunction are caused by primary or secondary hyperoxaluria (18, 27).

Patients who undergo chronic hemodialysis experience accelerated atherosclerosis and premature death (28). Plasma oxalate is proposed as an atherogenic toxin due to its contribution to elevated intracellular calcium levels, exclusively in endothelial cells, and hence prevention of re-endothelialization.

More significant toxic effects of oxalate and CaOx are its roles in developing CRF and ESRF (13, 14, 29-31). CaOx crystals deposit in the kidneys more frequent than in any other organ. It is proposed that CaOx crystals and/or high concentrations of oxalate evoke an inflammatory response and induce tubulointerstitial damage, which leads to fibrosis, loss of nephrons, and eventually to CRF and ESRF. Deposition of CaOx in the kidneys may accelerate kidney stone formation and growth. Due to the ability of CaOx stones to obstruct and cause physical damage to the kidneys, kidney stones are also a known risk for the development of renal failure (32).

Current treatments for severe oxalate situations. Since there is currently no cure for PH, ESRF will develop and kidney transplantation or combined liver/kidney transplantation is the eventual choice (33).

For severe SH patients, limiting the dietary intake of oxalate and its precursors is beneficial. However, if ESRF has developed, chronic dialysis and renal transplantation will be the ensuing choices (27).

For patients suffering with CRF or ESRF who undergo chronic dialysis, blood oxalate accumulation has been widely observed due to the limited ability of oxalate to be removed by current dialysis techniques. Furthermore, the situation is often worsened by the administration of large doses of vitamin C, a commonly used antioxidant for hemodialysis. Deposition of CaOx crystals in organs has been found in many cases (11, 21-23) and hyperoxaluria or formation of kidney stones is very common among these patients (10).

Oxalate degradation enzymes. There are two major oxalate degradation enzymes: oxalate decarboxylase and oxalate oxidase (www.brenda-enzymes.org/). However, no oxalate decarboxylase with activity at physiological pH (pH 7.4) has been found (www.brenda-enzymes.org/). *Bougainvillea spectabilis* leaves (Biochem. J., 1962, 85, 33) with some oxalate oxidase activity at pH 7.4 has been reported. However, no oxalate oxidase activity in solution was detected.

The present invention is based on screening of more than 1000 plant species for oxalate oxidase activity. The plant materials were collected in significantly different growth conditions and classification categories The plant material was analyzed for oxalate oxidase activity at pH 7.4 as described in Example 1 herein.

In those cases where the plant material contained oxalate oxidase with an activity of pH 7.4, it was tried to obtain small amounts of the enzymes. These oxalate oxidases are usually associated with cell wall and are quite challenging to dissolve. The purification process includes homogenization of plant tissue into particles smaller than 100 microns, and suspension of the particles in a containing surfactant and high concentration of salts or sugar to extract for 2-5 days. The crude extract is then loaded into Q-sepharose column after dialysis to remove surfactant and salts. The partly purified enzyme is then loaded into SDS-PAGE or native SDS-PAGE. In the native SDS-PAGE, the enzyme is still active and can be stained with activity assay solution. The band in SDS-PAGE can be cut out and used for amino acid sequence analysis of peptide segments of the protein by mass-spectrometry or used for N-terminal amino acid analysis. Only oxalate oxidases from banana and sweet beet have been purified.

Especially, OxOx from *Musa acuminate* (banana) peel, *Beta vulgaris* (beet) stem, *Bougainvillea spectabilis* leaves, *Mirabilis jalapa* young leaf, *Telosma cordatum* (Brum. f.) Merr leaf, *Jatropha gossypiifolia Linn.* var. *elegans Mueller* leaf and *Sauropus androgynus*(L.) Merr leaf shows significant activity at pH 7.5.

Thus, the present invention relates to oxalate oxidases derived from plant material and which has a sufficient activity (as defined herein) at pH 7.5. More specifically, the invention relates to a recombinant oxalate oxidase having a sufficient activity at pH 7.5 (as defined herein) and having amino acid sequences with an identity of at least 60% to the oxalate oxidases described herein, i.e. SEQ ID NO: 2, SEQ ID NO: 4, SEQ ID NO: 6, or SEQ ID NO:8. In particular the identity is at least 70% at least 75% at least 80% or at least 85%. Specifically, the identity is at least 90%, at least 95%, at least 98%, at least 99% or at least 100%.

The use of recombinant oxalate oxidases with amino acid sequences identical to those oxalate oxidase isolated or isolable from *Musa acuminate* (banana) peel, *Beta vulgaris* (beet) stem, *Bougainvillea spectabilis* leaves, *Mirabilis jalapa* young leaf, *Telosma cordatum* (Brum. f.) Merr leaf, *Jatropha gossypiifolia Linn.* var. *elegans Mueller* leaf and *Sauropus androgynus* (L.)Merr leaf for the treatment or prophylaxis of oxalate-related disease is subject of the present invention.

OxOx from banana peels (*Clinical Chemistry,* 1985; 31(4): 649) and beet stems (*Clinical Chemistry,* 1983; 29(10):1815-1819) have been reported in literature, but no activity around pH 7.4. It is suggested that the OxOx reported in literature may be different from those described here. As demonstrated in examples, three OxOx genes (5100, 5102, and 5601) have been isolated from sweet beet and they all have different amino acid sequences and DNA sequences, and show different properties as well. The 5100 and 5102 show very high activity (greater than 80% of the maximum activity) at pH 7.5, but the 5601 shows only 22% of the maximum activity at pH 7.5. Thus, it seems likely that none these OxO is the same as those reported in literature. Although only one OxOx gene has been cloned from banana in this work, there are dozens of related proteins with more than 50% similarity called germin or germin-like proteins in one single plant (Critical Reviews in Plant Sciences, 2008; 27 (5): 342-375). The presence of an oxalate oxidase from *Bougainvillea spectabilis* leaves (Biochem. J., 1962, 85, 33) has been reported in literature. OxOx from the other four plants are first discovered in this work.

Thus, the present invention relates to oxalate oxidase or fragments or variants thereof isolated from banana, sweet beet, *Mirabilis jalapa* young leaf, *Telosma cordatum* (Brum. f.) Merr leaf, *Jatropha gossypiifolia Linn.* var. *elegans Mueller* leaf and *Sauropus androgynus* (L.) Merr leaf.

The protein sequences of 5100, 5102, 5601 and 30640 are given in Example 2. 5100 and 5102 have 6 amino acids differently. 5102 shares 69% of identities of amino acids with 5601. All four proteins share only 37% identities. As shown in example 6, the activity profiles of the OxOx 5100 and 5102 in the pH range of 4.5 to 8.0 are very similar, showing high activity at pH 7.0-8.0. However, the activity profile of the OxOx 5601 in the pH range of 4.5 to 8.0 is different from the ones for 5100 and 5102, but similar to the one of 30640, showing a little activity at neutral pH.

Polynucleotides

The present invention also relates to isolated polynucleotides encoding the oxalate oxidases according to the invention, i.e. oxalate oxidases having a suitable (as defined herein) activity at pH 7-8

Thus, in another aspect the invention relates to a nucleotide having a nucleic acid sequence with an identity of at least 60% with SEQ ID NO: 1, SEQ ID NO: 3, SEQ ID NO: 5, SEQ ID NO: 7. In particular the identity is at least 70% at least 75% at least 80% or at least 85%. Specifically, the identity is at least 90%, at least 95%, at least 98%, at least 99% or at least 100%.

As shown in example 2, Genes 5100 and 5102 have 8 nucleotides differently. 5102 shares 69% of identities with 5601. All 4 genes share only 43% identities.

Nucleic Acid Constructs

The present invention relates to nucleic acid constructs comprising a polynucleotide encoding an oxalate oxidase of the present invention operably linked to one or more control sequences that direct the expression of the coding sequence in a suitable host under conditions compatible with the control sequence.

The polynucleotide may be manipulated in a variety of ways to provide for expression of an oxalate oxidase. Manipulation of the polynucleotide prior to its insertion into a vector may be desirable or necessary depending on the expression vector. The techniques for modifying polynucleotides utilizing recombinant DNA are well known to a person skilled in the art.

The control sequence may be a promoter, a polynucleotide recognized by a host cell for expression of a polynucleotide encoding an oxalate oxidase of the present invention. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promotes for directing transcription of the nucleic acid constructs of the present invention in a bacterial cell are promoters obtained from bacteria, virus or others, such as Lac, Trp, Tac, T7, $P_L$, or $P_R$.

Examples of suitable promotes for directing transcription of the nucleic acid constructs of the present invention in a fungal host cell are promoters obtained from yeast such as AOX1, GAP.

Examples of suitable promotes for directing transcription of the nucleic acid constructs of the present invention in a yeast host cell are promoters obtained from yeast such as AOX1, GAP.

The control sequence may also be a transcription terminator, which is recognized by a host cell to terminate transcription. The terminator is operably linked to the 3'-terminus of the polynucleotide encoding an oxalate oxidase. Any terminator that is functional in the host cell may be used such as TAA, TGA, TAG.

The control sequence may also be a leader a non-translated region of an mRNA that is important for the translation by the host cell. The leader is operably linked to the 5'-terminus of the polynucleotide encoding an oxalate oxidase of the invention. Any leader that is functional in the host cell may be used.

Suitable examples of leaders may be alpha-mating factor secretion signal, PHO1, PHA-E, alpha-amylase signal sequence (An-amyS), Glucoamylase signal sequence (Aa-GluS), Inulinase signal sequence (Km-InuS), Invertase signal sequence (Sc-InvS). Other examples are HFB1, HFB2, Scw, Dse, Exg, XPR2pre, or Lip2prepro.

Expression Vectors

The present invention also relates to recombinant expression vectors comprising a polynucleotide encoding an oxalate oxidase of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the oxalate oxidase at such sites. Alternatively, the polynucleotide may be expressed by inserting the polynucleotide in a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g. a plasmid or virus) that can be conveniently subjected to recombinant DNA procedures and can bring about expression of the polynucleotide. The choice of vector will typically depend on the compatibility of the vector with the host cell into which the vector is to be introduced. The vector may be a linear or closed circular plasmid.

The vector may contain one or more selectable markers that permit easy selection of transformed, transfected, transduced, or the like cells. A selectable marker is a gene the product of which provides for both biocide or viral resistance, resistance to heavy metals, and the like.

Suitable markers may be ampicillin, kanamycin, or neomycin.

For integration into the host cell genome, the vector may rely on the polynucleotide's sequence encoding the oxalate oxidase or any other element of the vector for integration into the genome by homologous or non-homologous recombination. Alternatively, the vector may contain additional polynucleotides for directing integration by homologous recombination into the genome of the host cell at a precise location(s) in the chromosome(s).

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication suitable for use in the present context are pUC, and p15A.

More than one copy of polynucleotide of the present invention may be inserted into a host cell to increase the production of oxalate oxidase. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well-known to a person skilled in the art.

Host Cells

The present invention also relates to recombinant host cells, comprising a polynucleotide encoding an oxalate oxidase of the present invention operably linked to one or more control sequences. A construct or vector comprising a polynucleotide is introduced into a host cell so that the construct or vector is maintained as a chromosomal integrant or as a self-replicating extra-chromosomal vector. The term "host cell" encompasses any progeny of a parent cell that is not identical to the parent cell due to mutations that occur during replication. The choice of host cell will to a large extent depend upon the gene encoding the oxalate oxidase and its source.

The host cell may be any cell useful in the recombinant production of an oxalate oxidase, e.g. a prokaryote or a eukaryote.

The prokaryotic host cell may be a bacterium such as *E. coli*, or *Bacillus subtilis*

The eukaryotic host cell may be a mammalian, insect, plant or fungal cell. The fungal cell may be a yeast cell. Suitable examples are *Pichia pastoris* X-33, GS115, *Yarrowia lipolytica, Lactuca sativa* L., *Pisum sativum*, and *Nicotiana benthamiana*.

Methods for Producing Oxalate Oxidases

The present invention also relates to methods of producing recombinant oxalate oxidases of the present invention, the method comprising i) cultivating a recombinant host cell of the present invention under conditions conductive for production of the oxalate oxidase, and ii) optionally recovering the oxalate oxidase.

The host cells are cultivated in a nutrient medium suitable for production of the oxalate oxidase using method well known in the art. For example the cells may be cultivated in multi-well plates, shake flask cultivation or small-scale or large-scale fermentation (including continuous, batch, fed-batch or solid state fermentation) in laboratory or industrial fermenters in a suitable medium and under conditions allowing the oxalate oxidase to be expressed and/or isolated. The cultivation takes place in a suitable nutrient medium comprising carbon and nitrogen sources and inorganic salts, using procedures known in the art.

Suitable media are: Small scale cultivation media: LB+2mM MnCl2

Large scale fermentation media:

Base medium (per L): $KH_2PO_4$ 13.5 g, Citrate acid.H2O 0.85 g, yeast powder 10 g, $MgSO_4 \cdot 7H_2O$ 1 g, trace metals solution 2.5 ml, Antifoam 204: 400 microliter, 100 mg/ml Amp 1 ml. Set pH to 6.85 after autoclaving. (Trace metals solution and Anti-foam 204 are added after autoclaving.)

Trace metals solution (per L):

$H_2SO_4$ 0.5 ml, $CuSO_4 \cdot 5H_2O$ 25 mg, $MnSO_4$ 2.28 g, $Na_2MoO_4 \cdot 2H_2O$ 25 mg, $ZnSO_4 \cdot 7H_2O$ 0.5 g, $CoCl_2 \cdot 6H_2O$ 45 mg, H3BO3 0.5 g, $CaCl_2 \cdot 2H_2O$ 3.25 g, $FeSO_4 \cdot 7H_2O$ 5 g.

Feed medium (per L):

glycerol 300 g, yeast powder 60 g.

The oxalate oxidase may be detected using methods known in the art that are specific for oxalate oxidases. These detection methods include, but are not limited to colorimetric assay, HPLC method.

The oxalate oxidase may be purified by a variety of procedures known in the art including, but not limited to, chromatography, dialysis, gel separation techniques etc.

Uses

As mentioned herein before a recombinant enzyme or a suitable derivative thereof according to the invention can be used in the treatment of diseases associated with the presence of excess of oxalate (compared to normal values). Examples of such disease are given above.

Oxalate Oxidase Compositions

It is envisaged that the recombinant oxalate oxidases as such or, if necessary, in a form, which reduces the possibility of unwanted immunological reactions in a patient, or which enhances e.g. the half-life of the enzyme in a body fluid such as blood or plasma. A general method is to subject the enzyme to pegylation.

The present invention also relates to pharmaceutical compositions for use in treating or preventing diseases associated with excess oxalate, wherein the composition contains a recombinant oxalate oxidase or a derivative thereof (e.g. a pegylated oxalate oxidase) having suitable activity at pH 7-8 (as described above).

The compositions may be designed to oral, parenteral or mucosal administration. Thus the administration may be oral, sublingual, application to the oral mucosa, or it may be intraveneous, subcutaneous, intramuscular, intraperitoneal, intrahecal etc. or it may be applied to the skin or a mucosa surface including ocular, buccal, nasal, vaginal and rectal mucosa.

The composition may be in solid, semi-solid or liquid form.

Suitable solid compositions include powders, granules, pellets, capsules, tablets (included coated tablets), sachets, implants etc.

Suitable semi-solid compositions include gels, pastes, crèmes, ointments, vagitories, suppositories etc.

Suitable liquid or fluid compositions include solutions, dispersion, emulsions, suspension, lotions, sprays, aerosols The compositions may conveniently be presented in unit dosage form and may be prepared by any of the methods well known in the art of pharmacy. Such methods include the step of bringing into association the enzyme with the carrier which constitutes one or more accessory ingredients. In general the compositions are prepared by uniformly and intimately bringing into association the active ingredient with liquid carriers or finely divided solid carriers or both, and then, if necessary, shaping the product.

As mentioned above the recombinant oxalate oxidase may be administered orally in the form of an enteric coated pharmaceutical formulation or a pharmaceutical composition which by other means are protected from degradation of the enzyme in the stomach. The pharmaceutical formulation comprises the recombinant enzyme in a pharmaceutically acceptable dosage form. Depending upon the disorder and patient to be treated, as well as the route of administration, the compositions may be administered at varying doses.

For example, the recombinant enzymes of the invention can be administered orally, buccally or sublingually in the form of tablets, capsules, ovules, elixirs, solutions or suspensions, which may contain flavouring or colouring agents, for immediate-, delayed- or controlled-release applications. For peroral administration means must be taken to avoid release or degradation of the enzyme in the stomach.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatine and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, crosslinked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated e.g. with an enteric coating and may be formulated so as to provide slow or controlled release of the active ingredient therein using, for example, hydroxypropylmethylcellulose in varying proportions to provide desired release profile.

Compositions for use in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion.

It should be understood that in addition to the ingredients particularly mentioned above the formulations of this invention may include other agents conventional in the art having regard to the type of formulation in question, for example those suitable for oral administration may include flavouring agents.

Advantageously, agents such as preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

The composition may also be designed for parenteral administration. Such compositions may contain excipients, which are pharmaceutically acceptable for a composition to be injected. These may be in particular isotonic, sterile saline solutions (phosphate, sodium chloride) or dry, especially freeze-dried compositions, which upon addition, depending on the case, of sterilized water or physiological saline, are reconstituted to a ready-to-use composition.

The pharmaceutical compositions suitable for injection include sterile aqueous solutions or dispersions. The compositions may include solvents like water or ethanol, sesame oil, peanut oil or the like, glycerol or propylene glycol. pH-adjusting agent may be added to adjust pH of the composition and preservatives may also be added.

A person skilled in the art will be able to prepare a composition that is suitable for use in accordance with the present invention based on the disclosure herein and/or with guidance from Remington's Pharmaceutical Sciences, 18$^{th}$ Ed. Mack Publishing Company, 1990 or newer editions.

The dosage to be administered of an oxalate oxidase will vary according to the particular disease involved, the subject, and the nature and severity of the disease and the physical condition of the subject, and the selected route of administration.

The appropriate dosage can be readily determined by a person skilled in the art.

The compositions may contain from 0.1% by weight, preferably from 5-90%, more preferably from 10-80% by weight, of an oxalate oxidase of invention, depending on the particular composition and the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice Definitions cDNA: The term "cDNA" means a DNA molecule that can be prepared by reverse transcription from a mature, spliced mRNA molecule obtained from a cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of the enzyme or variant of the enzyme. The boundaries of the coding sequence are generally determined by an open reading frame, which begins with a start codon such as ATG, GTG or TTG and ends with a stop codon such as TAA, TAG or TGA. The coding sequence may be genomic DNA, cDNA, synthetic DNA, or a combination thereof.

Control sequences: The term "control sequences" means nucleic acid sequences necessary for expression of a polynucleotide encoding an oxalate oxidase or variant of the present invention. Each control sequences must be native (i.e. from the same gene) or foreign (i.e. from a different gene) to the polynucleotide encoding the oxalate oxidase or variant thereof or native or foreign to each other. Such control sequences include a promoter, and transcriptional and translational stop signals. The control sequences may be provided with linkers for the purpose of introducing specific restriction sites facilitating ligation of the control sequence with the coding region of the polynucleotide encoding the oxalate oxidase or variant thereof.

Expression: The term "expression" includes any step involved in the production of an oxalate oxidase or variant thereof including, but not limited to, transcription, posttranscriptional modification, translation, post-translational modification, and secretion.

Expression vector: The term "expression vector" means a linear or circular DNA molecule that comprises a polynucleotide encoding an oxalate oxidase or variant thereof and is operably linked to control sequences that provide for its expression.

Fragment: The term "fragment" means a polypeptide having one or more (e.g. several) amino acids absent from the amino and/or carboxyl terminus of the polypeptide thereof, wherein the fragment has oxalate oxidase activity. The fragment may have at least 85% of the amino acid residues e.g. at least 90% or at least 95% of the amino acid residues of the mature polypeptide.

Host cell: The term "host cell" means any cell type that is susceptible to transformation, transfection, transduction, or the like with a nucleic acid construct or expression vector comprising a polynucleotide as described herein.

Isolated: The term "isolated" means a substance in the form or environment that does not occur in nature. Non-limiting examples of isolated substances include i) any non-naturally occurring substance, ii) any substance including, but not limited to, any enzyme, variant, nucleic acid, protein, peptide or cofactor, that is at least partially removed from one or more or all of the naturally occurring constituents with which it is associated in nature, iii) any substance modified by the hand of man relative to that substance found in nature, or iv) any substance modified by increasing the amount of the substance relative to other components with which it is naturally associated.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide, such that the control sequence directs expression of the coding sequence.

Optimum pH: The term "optimum pH" means the pH value where the enzymatic activity is at its maximum level or at least 80% e.g. 85%, 90%, 95% or 98% of its maximum level.

Oxalate-related disease: The term "oxalate-related disease" means and disease or condition caused by an excess of oxalate in the body compared to normal level. Such disease or conditions include, but are not limited to, primary hyperoxaluria (PH), secondary hyperoxaluria (SH), Zellweger spectrum disorders (ZSD), and chronic renal failure or end-stage renal failure (ESRF), autism, vulvodynia, oxalosis associated with end-stage renal disease, cardiac conductance disorders, Crohn's disease, inflammatory bowel disease, colitis, urolithiasis, oxalosis associated with end-stage renal disease, sarcoidosis, asthma, COPD, fibromyalgia, Zellweger syndrome, bariatric surgery and other enteric disease states.

Sequence identity: The term "sequence identity" means the relatedness between two amino acid sequences or between two nucleotide sequences. Blast algorithm was used. It is provided by pubmed.gov, i.e., national center for biotechnology information.

Specific activity: The term "specific activity refers to the enzyme activities per mg of protein.

Unit: One unit of activity is defined as the enzyme amount required to produce 1 µmole of formate from oxalate under the conditions described in Example 6 herein.

Variant: The term "variant" means a polypeptide having oxalate oxidase activity comprising an alteration, i.e. a substitution, insertion, and/or deletion, at one or more (e.g. several) positions. A substitution means replacement of the amino acid occupying a position with a different amino acid; a deletion means removal of an amino acid occupying a position; and an insertion means adding an amino acid adjacent to and immediately following the amino acid occupying the position. The variants of the present invention have at least 20%, e.g. at least 40%, at least 50%, at least 60%, at least 70%, at least 80%, at least 90%, at least 95% or 100% of the oxalate oxidase activity of the parent oxalate oxidase.

LEGENDS TO FIGURES

FIG. 1. Modifications of the pET-32 vector to generate the pAT plasmid. The DNA sequence highlighted in yellow was deleted in a pET-32 vector (SEQ ID NO. 23) to generate the pAT plasmid (SEQ ID NO. 24).

Figure 2:
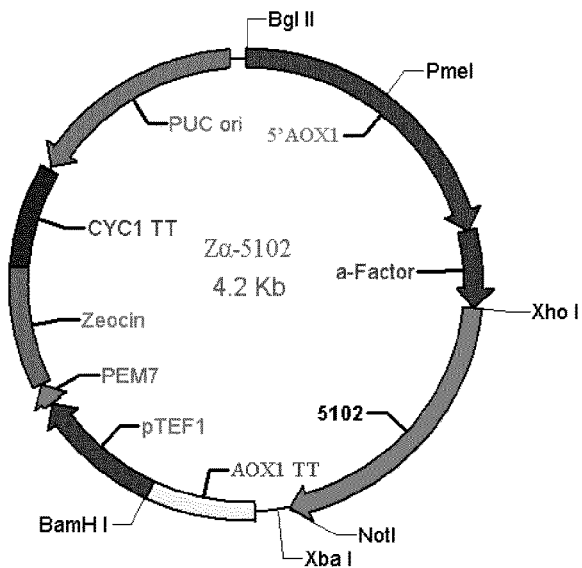

FIG. 2 Schematic diagram of the *Pichia* expression plasmid Zα-5102.

Figure 3:
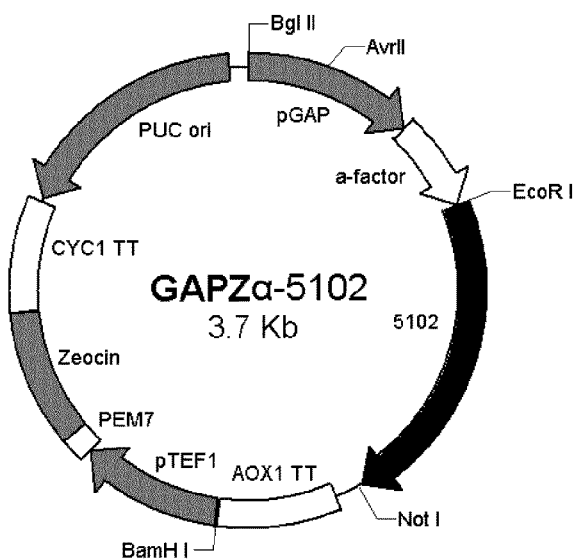

FIG. 3 Schematic diagram of the *Pichia* expression plasmid GAPZα-5102.

Figure 4:
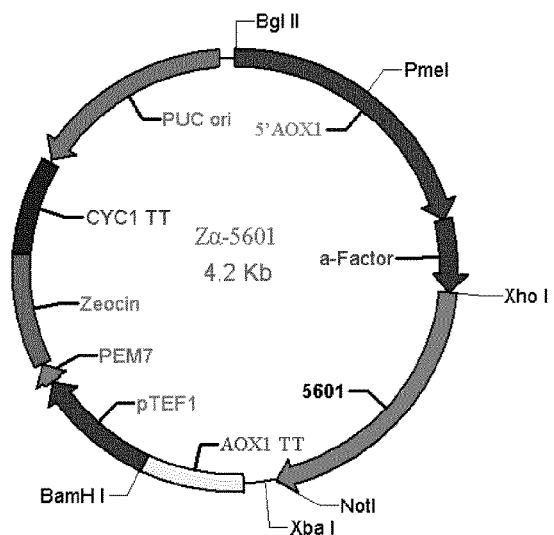

FIG. 4 Schematic diagram of the *Pichia* expression plasmid Zα-5601.

Figure 5:
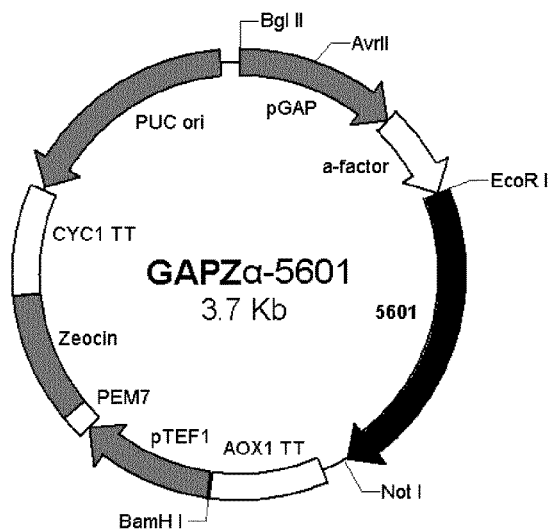

FIG. 5 Schematic diagram of the *Pichia* expression plasmid GAPZα-5601.

Figure 6:
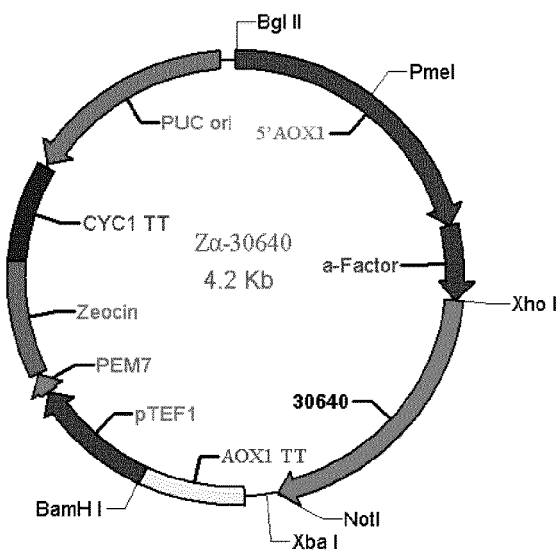

FIG. 6 Schematic diagram of the *Pichia* expression plasmid Zα-30640.

Figure 7:
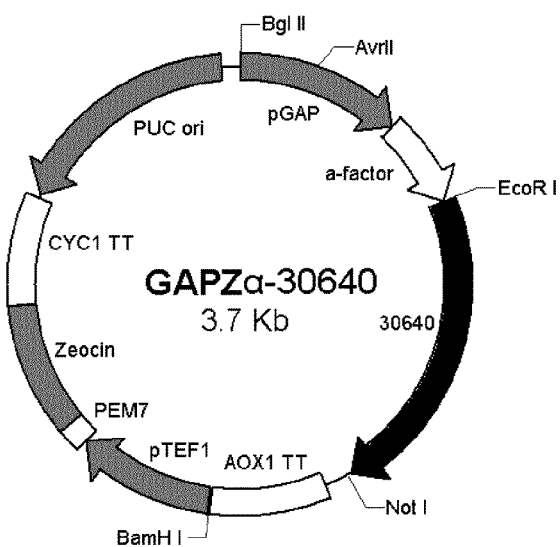

FIG. 7 Schematic diagram of the *Pichia* expression plasmid GAPZα-5102.

Figure 8:
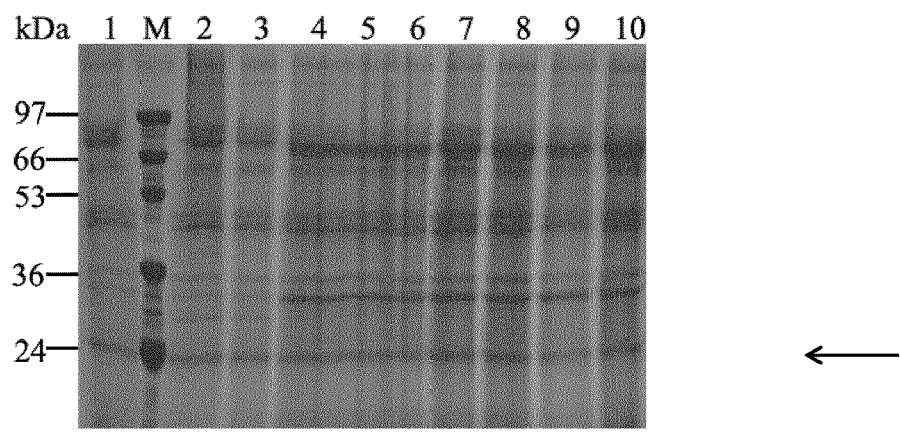

FIG. 8 SDS-PAGE analysis of the expression of beet OxO in *P. pastoris*. M: protein marker; M: protein marker; lanes 1-10, X-33 (ZαA-5102).

Figure 9:
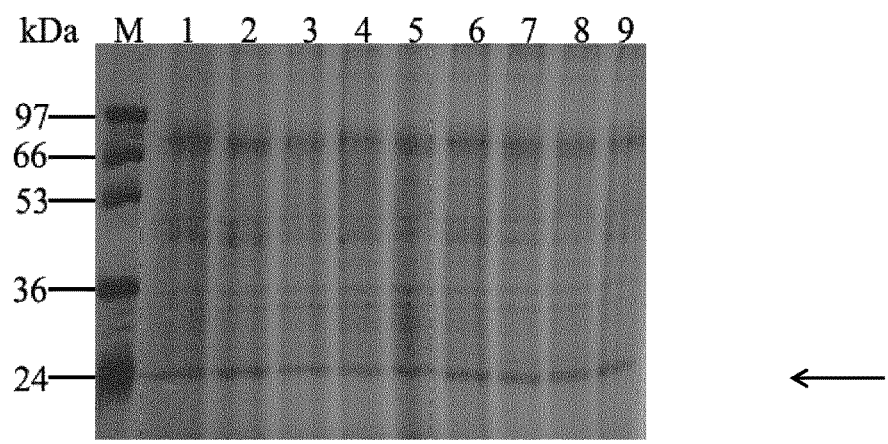

FIG. 9 SDS-PAGE analysis of the expression of beet OxO in *P. pastoris*. M: protein marker; lanes 1-9, X-33(Zα-5601).

Figure 10:
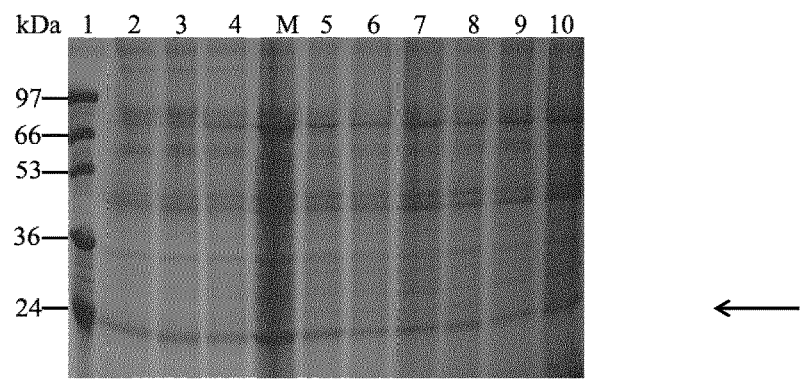

FIG. 10 SDS-PAGE analysis of the expression of banana OxO in *P. pastoris*. M: protein marker; lanes 1-10, X-33 (ZαA-30640).

Figure 11:
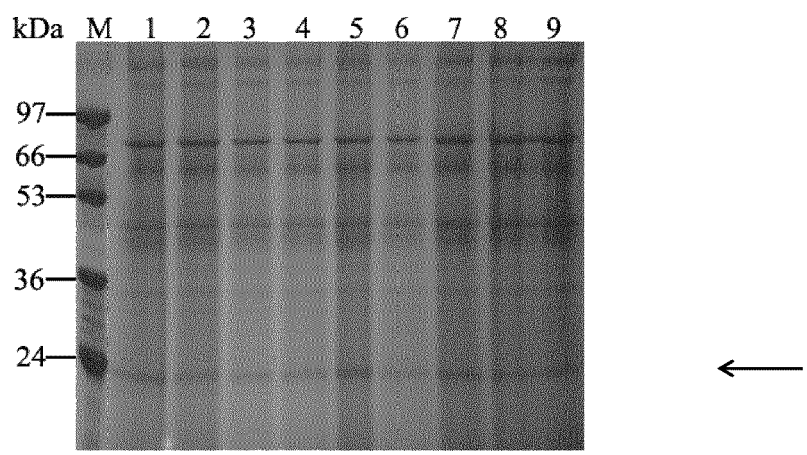

FIG. 11 SDS-PAGE analysis of the expression of beet OxO in *P. pastoris*. M: protein marker; lanes 1-9, X-33 (GAPZα-5601).

Figure 12:
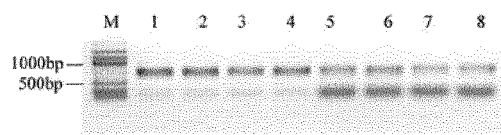

FIG. 12 PCR amplification of the OxO genes from cDNA library of sugar beet. M. DNA Maker; Lane 1-4, 5601; Lane 5-8, 5102

Figure 13:
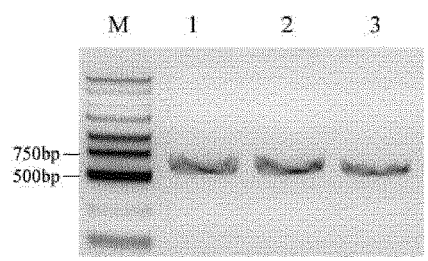

FIG. 13 PCR amplification of the OxO gene from cDNA library of banana. M. DNA Maker; Lane 1-3, 30640

Figure 14:
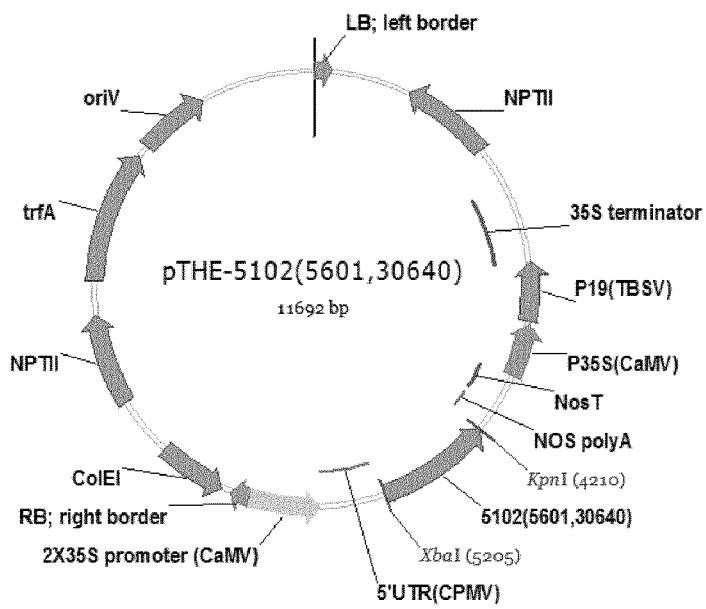

FIG. 14 Schematic diagram of the plant expression vector

Figure 15:
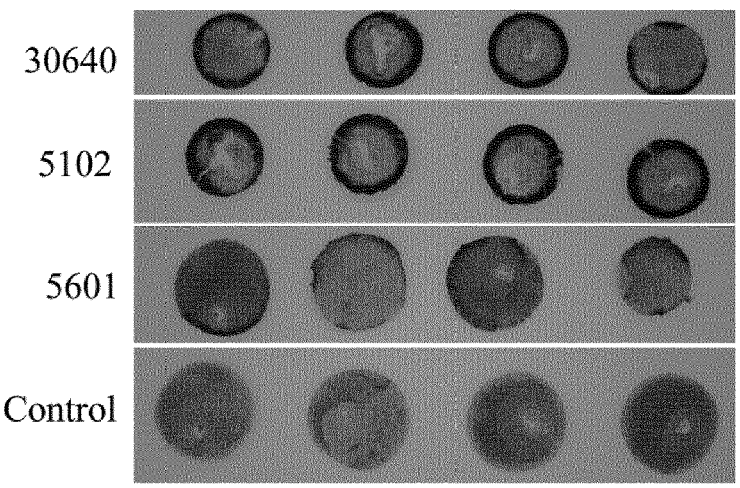
Figure 16:
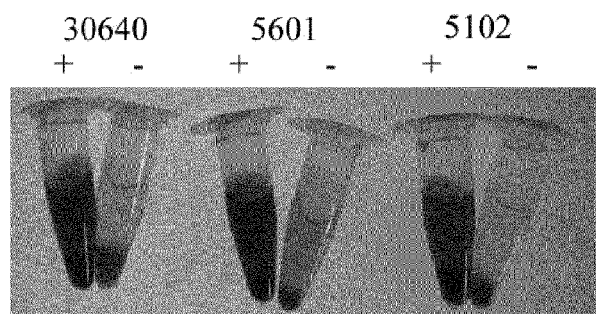

FIG. 15 Histochemical assay of oxalate oxidase activity after overnight incubation in OxOx histological buffer FIG. 16 Detection of OxO activity of the purified cell wall fraction from pea plants by colorimetric assay, pH 7.4. The left tube containing 2 mM oxalic acid; The right tube containing no oxalic acid.

Figure 17:
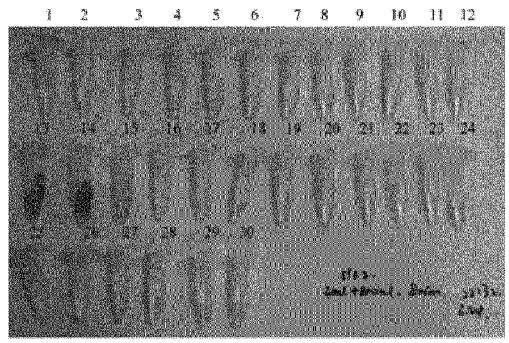

FIG. 17 Detection of OxOx activity of the purified 5102 fractions from pea plants.

Figure 18:
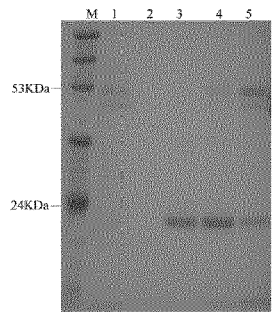

FIG. 18 Purification of recombinant beet OxOx 5102. M, Protein Maker; lane 1, Sample before purified by Q Sepharose column; Lane 2, the washing sample; Lane 3, eluted sample 13#; Lane 4, eluted sample 14#; Lane 5, eluted sample 15#.

Figure 19:
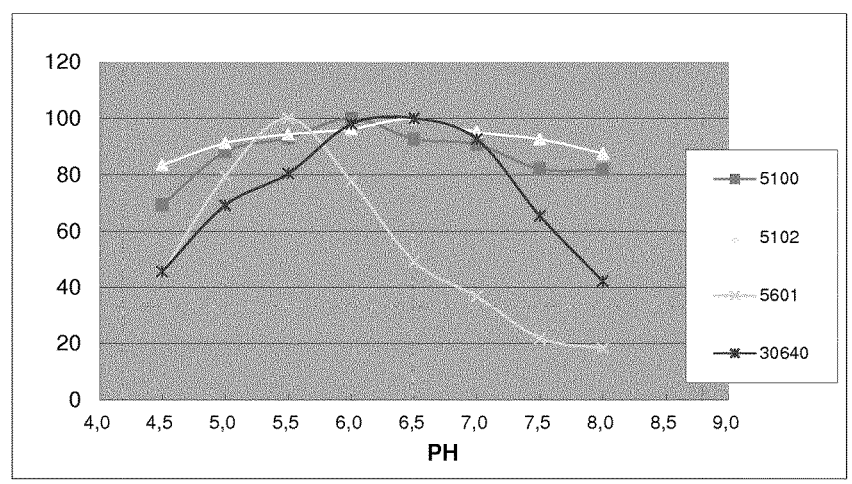

FIG. 19 Relative activity of recombinant oxalate oxidases.

Figure 20:
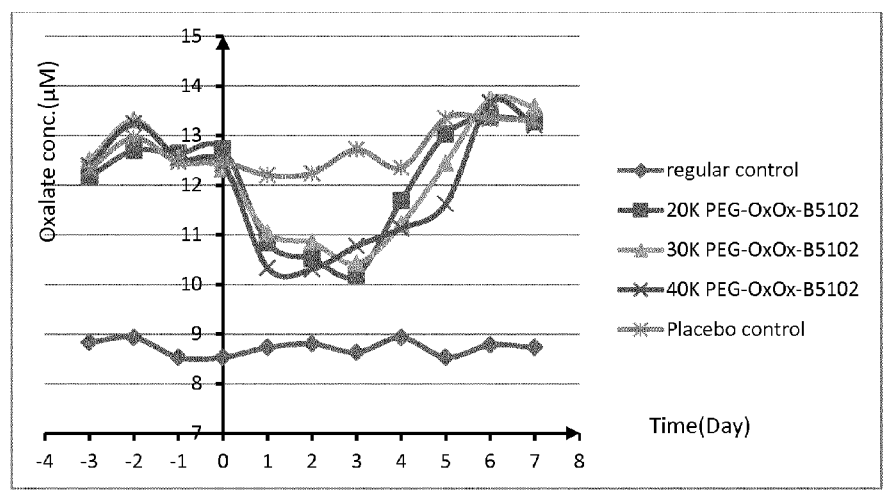

FIG. 20 Serum oxalate concentration curve from Example 12.

Figure 21:
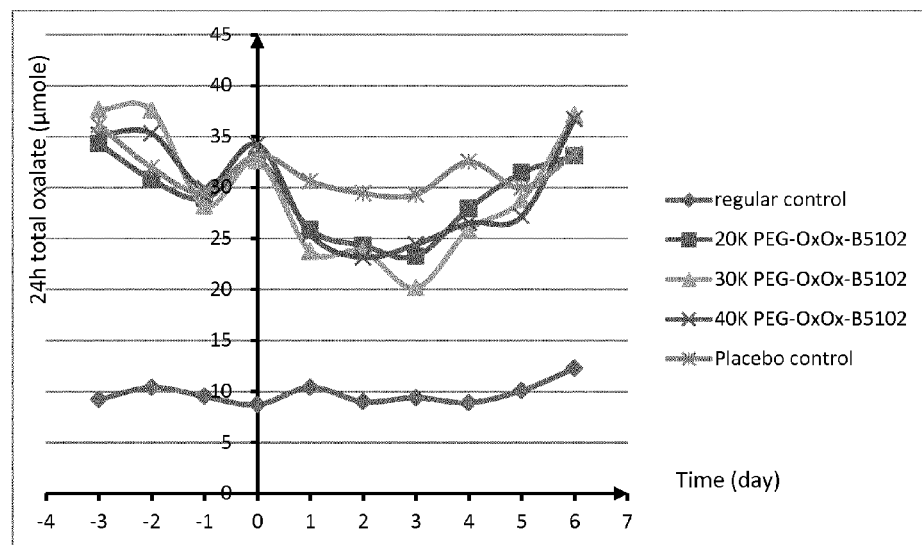

FIG. 21 24 h total urine oxalate curve from Example 12.

Figure 22:
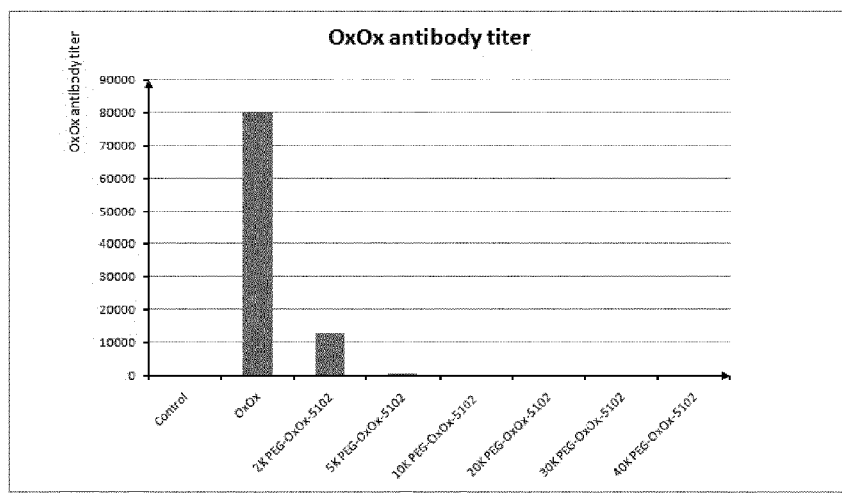

FIG. 22 OxOx-B5102 antibody titer detection of different PEG-OxOx-B5102s from Example 12.

FIG. 23 Sequence Listing

REFERENCES

1. Monico, C. G., Persson, M., Ford, G. C., Rumsby, G., and Milliner, D. S. (2002) Potential mechanisms of marked hyperoxaluria not due to primary hyperoxaluria I or II, *Kidney Int* 62, 392-400.
2. Hoppe, B., Beck, B. B., and Milliner, D. S. (2009) The primary hyperoxalurias, *Kidney Int* 75, 1264-1271.
3. Hoppe, B., Kemper, M. J., Bokenkamp, A., Portale, A. A., Cohn, R. A., and Langman, C. B. (1999) Plasma calcium oxalate supersaturation in children with primary hyperoxaluria and end-stage renal failure, *Kidney Int* 56, 268-274.
4. Hoppe, B., Kemper, M. J., Bokenkamp, A., and Langman, C. B. (1998) Plasma calcium-oxalate saturation in children with renal insufficiency and in children with primary hyperoxaluria, *Kidney Int* 54, 921-925.
5. Mydlik, M., and Derzsiova, K. (2008) Oxalic Acid as a uremic toxin, *J Ren Nutr* 18, 33-39.
6. Bernhardt, W. M., Schefold, J. C., Weichert, W., Rudolph, B., Frei, U., Groneberg, D. A., and Schindler, R. (2006) Amelioration of anemia after kidney transplantation in severe secondary oxalosis, *Clin Nephrol* 65, 216-221.
7. Marangella, M., Vitale, C., Petrarulo, M., and Linari, F. (1995) The clinical significance of assessment of serum calcium oxalate saturation in the hyperoxaluria syndromes, *Nephrol Dial Transplant* 10 Suppl 8, 11-13.
8. van Woerden, C. S., Groothoff, J. W., Wijburg, F. A., Duran, M., Wanders, R. J., Barth, P. G., and Poll-The, B. T. (2006) High incidence of hyperoxaluria in generalized peroxisomal disorders, *Mol Genet Metab* 88, 346-350.
9. Ogawa, Y., Machida, N., Ogawa, T., Oda, M., Hokama, S., Chinen, Y., Uchida, A., Morozumi, M., Sugaya, K., Motoyoshi, Y., and Hattori, M. (2006) Calcium oxalate saturation in dialysis patients with and without primary hyperoxaluria, *Urol Res* 34, 12-16.
10. Canavese, C., Petrarulo, M., Massarenti, P., Berutti, S., Fenoglio, R., Pauletto, D., Lanfranco, G., Bergamo, D., Sandri, L., and Marangella, M. (2005) Long-term, low-dose, intravenous vitamin C leads to plasma calcium oxalate supersaturation in hemodialysis patients, *Am J Kidney Dis* 45, 540-549.
11. Maldonado, I., Prasad, V., and Reginato, A. J. (2002) Oxalate crystal deposition disease, *Curr Rheumatol Rep* 4, 257-264.
12. Cochat, P., Liutkus, A., Fargue, S., Basmaison, O., Ranchin, B., and Rolland, M. O. (2006) Primary hyperoxaluria type 1: still challenging!, *Pediatr Nephrol* 21, 1075-1081.
13. Tintillier, M., Pochet, J. M., Blackburn, D., Delgrange, E., and Donckier, J. E. (2001) Hyperoxaluria: an underestimated cause of rapidly progressive renal failure, *Acta Clin Belg* 56, 360-363.
14. Nasr, S. H., D'Agati, V. D., Said, S. M., Stokes, M. B., Largoza, M. V., Radhakrishnan, J., and Markowitz, G. S. (2008) Oxalate nephropathy complicating Roux-en-Y Gastric Bypass: an underrecognized cause of irreversible renal failure, *Clin J Am Soc Nephrol* 3, 1676-1683.
15. Nasr, S. H., Kashtanova, Y., Levchuk, V., and Markowitz, G. S. (2006) Secondary oxalosis due to excess vitamin C intake, *Kidney Int* 70, 1672.
16. (2008) USRDS 2008 Annual Data Report., in United States Renal Data System Web site. www.usrds.org/adr.htm.
17. Cornelis, T., Bammens, B., Lerut, E., Cosyn, L., Goovaerts, G., Westhovens, R., and Vanrenterghem, Y. (2008) AA amyloidosis due to chronic oxalate arthritis and vasculitis in a patient with secondary oxalosis after jejunoileal bypass surgery, *Nephrol Dial Transplant* 23, 3362-3364.
18. Rankin, A. C., Walsh, S. B., Summers, S. A., Owen, M. P., and Mansell, M. A. (2008) Acute oxalate nephropathy causing late renal transplant dysfunction due to enteric hyperoxaluria, *Am J Transplant* 8, 1755-1758.
19. Sule, N., Yakupoglu, U., Shen, S. S., Krishnan, B., Yang, G., Lerner, S., Sheikh-Hamad, D., and Truong, L. D. (2005) Calcium oxalate deposition in renal cell carcinoma associated with acquired cystic kidney disease: a comprehensive study, *Am J Surg Pathol* 29, 443-451.
20. Lefaucheur, C., Nochy, D., Amrein, C., Chevalier, P., Guillemain, R., Cherif, M., Jacquot, C., Glotz, D., and Hill, G. S. (2008) Renal histopathological lesions after lung transplantation in patients with cystic fibrosis, *Am J Transplant* 8, 1901-1910.
21. Nakazawa, R., Hamaguchi, K., Hosaka, E., Shishido, H., and Yokoyama, T. (1995) Cutaneous oxalate deposition in a hemodialysis patient, *Am J Kidney Dis* 25, 492-497.
22. Ono, K., and Kikawa, K. (1989) Factors contributing to oxalate deposits in the myocardia of hemodialysis patients, *ASAIO Trans* 35, 595-597.
23. Ohtake, N., Uchiyama, H., Furue, M., and Tamaki, K. (1994) Secondary cutaneous oxalosis: cutaneous deposition of calcium oxalate dihydrate after long-term hemodialysis, *J Am Acad Dermatol* 31, 368-372.
24. Perera, M. T., McKiernan, P. J., Sharif, K., Milford, D. V., Lloyd, C., Mayer, D. A., Kelly, D. A., and Mirza, D. F. (2009) Renal function recovery in children undergoing combined liver kidney transplants, *Transplantation* 87, 1584-1589.
25. Alsuwaida, A., Hayat, A., and Alwakeel, J. S. (2007) Oxalosis presenting as early renal allograft failure, *Saudi J Kidney Dis Transpl* 18, 253-256.
26. Truong, L. D., Yakupoglu, U., Feig, D., Hicks, J., Cartwight, J., Sheikh-Hamad, D., and Suki, W. N. (2004) Calcium oxalate deposition in renal allografts: morphologic spectrum and clinical implications, *Am J Transplant* 4, 1338-1344.
27. Cuvelier, C., Goffin, E., Cosyns, J. P., Wauthier, M., and de Strihou, C. Y. (2002) Enteric hyperoxaluria: a hidden cause of early renal graft failure in two successive transplants: spontaneous late graft recovery, *Am J Kidney Dis* 40, E3.
28. Recht, P. A., Tepedino, G. J., Siecke, N. W., Buckley, M. T., Mandeville, J. T., Maxfield, F. R., and Levin, R. I. (2004) Oxalic acid alters intracellular calcium in endothelial cells, *Atherosclerosis* 173, 321-328.
29. Khan, S. R. (2004) Crystal-induced inflammation of the kidneys: results from human studies, animal models, and tissue-culture studies, *Clin Exp Nephrol* 8, 75-88.
30. Umekawa, T., Iguchi, M., Uemura, H., and Khan, S. R. (2006) Oxalate ions and calcium oxalate crystal-induced up-regulation of osteopontin and monocyte chemoattractant protein-1 in renal fibroblasts, *BJU Int* 98, 656-660.
31. Dell'Aquila, R., Feriani, M., Mascalzoni, E., Bragantini, L., Ronco, C., and La Greca, G. (1992) Oxalate removal by differing dialysis techniques, *ASAIO J* 38, 797-800.
32. Gambaro, G., Favaro, S., and D'Angelo, A. (2001) Risk for renal failure in nephrolithiasis, *Am J Kidney Dis* 37, 233-243.
33. Brinkert, F., Ganschow, R., Helmke, K., Harps, E., Fischer, L., Nashan, B., Hoppe, B., Kulke, S., Muller-Wiefel, D. E., and Kemper, M. J. (2009) Transplantation procedures in children with primary hyperoxaluria type 1: outcome and longitudinal growth, *Transplantation* 87, 1415-1421.

EXAMPLES

Strains and Plants
*E. coli* BL21(DE3), *E. coli* Origami B(DE3), *P. pastoris*, Wild-type *N. benthamiana* plants, *P. sativum* plants.

Example 1

Screening of Plants and Testing for Oxalate Oxidase Activity
Collection of plants species: more than 1000 plants species were collected for testing. Here is a list of the plants which have been tested.

| | |
|---|---|
| *Vitis vinifera* | *Lanrus nobilis* Linn |
| *Fragaria ananassa* Duchesne | *Parakmeria Latungensis* |
| *Eriobotrya japonica* | *Parakmeria Yunnanensis* |
| *Coriandrum sativum* L. | *Eucommia ulmoides* Oliver |
| *Chrysanthemum coronarium* | *Loropetalum chinensis* (R. Br.) Oliv |
| *Brassica rapa chinensis* | *Celtis sinensis* Pers |
| *Brassica rapa pekinensis* | *Tulipa gesneriana* |
| *Brassica campestris pekinensis* | *Sinojackia xylocarpa* Hu |
| *Brassica pekinensis* | *Osmanthus armatus* Diels |
| *Lactuca sativa* | *Malus hupehensis*(Pamp.)Rehd |
| *Vicia faba* Linn | *Sloanea hemsleyana* |
| *Pisum sativum* Linn | *ligustrum japonicum* |
| *Solanum tuberosum* L | Thunb. var *rvtundifolium* B1 |
| *Solanum tuberosum* L | *Pittosporum tobira* |
| *Colocasia esculenta* | *Acer palmatum* |
| *Lactuca sativa* L. var. *capitata* L. | *E. pungens* Thunb |
| Bamboo Shoot | *Prunus ceraifera* |
| *Brassica parachinensis* | *Taiwania cryptomerioides* Hayata |
| *Toona sinensis*. A. Juss. | *Chaenomeles sinensis* Koehne |
| *Pisum sativum* Linn | *Taxus wallichiana* Zucc |
| *Allium sativum* L. | *Ormosia henryi* Prain |
| *Apium graveolens* L. | *Pyracantha fortuneana* |
| *Hordeum vulgare* L. | *Mallotus repandus* (Willd.) Muell. Arg |
| *Hordeum vulgare* L. | *Distylium racemosum* Sieb. et Zucc |
| *Hordeum vulgare* L. | *Viburnum setigerum* Hance |
| *Cruciferae Brassica* | *Jasminum mesnyi* |
| *Allium epa* L. | *Chimonanthus praecox*(L.)Link |
| Alliaceae *Allium A. tuberosum* | *Hovenia acerba* Lindl. |
| *Dioscorea opposita* | *Mahonia fortunei* (Lindl.)Fedde |
| *Vigna radiata* | *Cercis chinensis* Bge |
| *Momordica charantia* | *Chionanthus retusus* |
| *Cucumis sativus* Linn | *Fraxinus hupehensis* |
| *Benincasa hispida* | *Alpinia zerumbet* |
| *Ananas comosus* | *Asparagus myriocladus* |
| *Ananas comosus* | *Cerasus conradinae* (Koehne) |
| *Prunus ceraifera* cv. *Pissardii* | Yü et Li |
| Alliaceae *Allium A. tuberosum* | *Juniperus chinensis* cv. *kaizuka* |
| *Pisum sativum* Linn | *Brunfelsia acuminata*(Pohl.)Benth |
| *Benincasa hispida* | *Bambusa ventricosa* McClure |
| *Benincasa hispida* | *Hedera nepalensis* |
| *Vigna radiata* | *Dendrobeaathamia capitata*(Wall.) |
| *Cruciferae Brassica* | Hutoh. var. *emeiensis*(Fang et Hsi- |
| *Momordica charantia* | eh)Fang et. W. K. Hu |
| *Ananas comosus* | *Cyperus papyrus* L. |
| Alliaceae *Allium A. tuberosum* | *Pilea nummulariifollia*(Sw.)Wedd. |
| Alliaceae *Allium A. tuberosum* | *Syngonium podophyllum* |
| *Benincasa hispida* | :*Iresine herbstii* Hook. f |
| *Vigna radiata* | Simlax China L |
| *Giycine max*(L)Merrill | *Gleditsia japonica* |
| *Eleocharis dulcis* | *Euonymus grandiflorus* Wall. |
| Alliaceae *Allium A. tuberosum* | Planch. cv. *Fenghongpeier* |
| *Sorghum bicolor* | *Ilex cornuta* Lindl. et Paxt. |
| *Brassic campestris* | *Berchemia sinica* Scheid |
| *Galium aparine* | *Symplocos sununtia* Buch.- |
| *Geranium carolinianum*L.. | Ham. ex. D. Don |
| *Euphorbia helioscopia* | *Dianthus chinensis* L. |
| *Portulaca oleracea* L. | *Olea europaea* L |
| *Oxalis corniculata* | *Begonia masoniana* |
| *Vicia sepium* linn. | *Marsilea quadrifolia* |
| *Eugenia javanica* | *Hibiscus rosa-sinensis* L. |
| Lam 【 leaves 】 | *Dracaena cochinchinen* |
| *Eugenia javanica* | Common Rush |
| Lam 【 fruit 】 | *Manilkara zapota* van Royen |
| *Reineckea carnea* | *Ligustrum lucidum* Ait |
| *Bougainvillea spectabilis* wind | *Begonia thurstonin* |

-continued

| | |
|---|---|
| Bougainvillea spectabilis wind | Nephrolepis biserrata (Sw.) Schott |
| Sinojackta huanamelensis | Quisqualis indica |
| Neolitsea sericea | Asystasia gangetica |
| Heptacodium Miconiodes rehd | Podocarpus macrophyllus |
| banana | Artabotrys hexapetalus (L.f.) Bhandari |
| Populus bonatii Levl | Telosma cordatum (Brum. f.) Merr |
| Vitis vinifera | Forsythia viridissima |
| Prunus armeniaca L. | Osmanthus matsumuranus Hayata |
| Mirabilis jalapa Linn | Phoebe zhennan S. Lee et F. N. Wei |
| Mirabilis jalapa Linn | Davidia involucrata Baill |
| Gordonia axillaris | Neolepisorus ovatus |
| Lindera aggregata (Sims) | Setcreasea pallida |
| Kosterm | Clerodendron japonicum (Thunb.) |
| Lllicium henryi | Sweet |
| PhoebechekiangensisC. B. Shang | Hydrangea macrophylla (Thunb.)Ser |
| Fokienia hodginsii (Dunn) Henry | Psidium littorale Raddi |
| et Thomas | Savia miltiorrhiza Bunge |
| Viburnum macrocephalum | Fagraea ceilanica |
| f. keteleeri | Paeonia suffruticosa"" |
| Zanthoxylum simullans Hance | Sycopsis sinensis Oliver |
| Cinnamomum camphora | Aesculus wilsonii Rehd |
| Acer albopurpurascens Hayata | Edyeworthia chrysantha Lindl |
| Daphniphyllum macropodum Miq | Pilea peperomioides Diels |
| Camellia sasanqua | Helleborus thibetanus Franch. |
| Sinocalycanthus chinensis | Euonymus fortunei Hand.-Mazz. |
| Bulbus Fritillaria | Dicliptera chinensis |
| Costus tonkinensis Gagnep | Stevia rebaudiana |
| Disporum bodinieri (Levi. et | Rhizoma Alpiniae Officinarum |
| Vaniot.) | Asarum forbesii Maxim |
| Podocarpus fleuryi | Sarcandra glabra |
| Tetracentron sinense | Peristrophe baphica |
| Reinwardtia trigyna | Peperomia tetraphylla |
| Valeriana hardwickii | Erythrina crista-galli L |
| Fagopyrum dibotrys (D. Don) | Rumex japonicus Houtt |
| Hara | Melodinus hemsleyanus Diels. |
| Thalia dealbata | Tibouchina aspera |
| Muscari botryoides Mill. | Rumex hastatus |
| Fagus longipetiolata Seem | Hibiscus Sabdariffa Linn |
| Jussiaea reppens L. | Catharanthus roseus |
| Podocarpus fleuryi | Tragopogon porrifolius Linn |
| Ardisia crenata Sim | Mussaenda pubescens Ait. f. |
| Torreya fargesii Franch | Sedum sarmentosum Bunge |
| Aesculus wangii Hu ex Fang | Pilea cavaleriei Levl |
| Nerium oleander | Sauropus rostrata Miq |
| Strobilanthes cusia | Acorus gramineus |
| Drynaria fortunei | Euphorbia neriifolia L. |
| Belamcanda chinensis | Euphorbia tirucalli Linn |
| Kalimeris indica (Linn.) Sch.) | Dianthus serotinus |
| Rhoeo discolor | Codariocalyx motorius |
| Fiveleaf Gynostemma Herb | Acalypha hispida |
| Sterculia nobililis | Acalypha hispida |
| Choerospondias axillaris | Garcinia oblongifolia |
| Citrus medica L. var. sarcodactylis | Cynanchum stauntonii |
| Gynostemma compressum | Aloe vera var. chinensis |
| Chrysanthemum indicum | Polygonum capitatum |
| SpilsheS acmella (Linn) Murr | Iris japonica |
| Ilex kudmcha C. J. Tseng | Acanthopanax gracilistylus |
| Cinnamomum cassia | Dicranostigma leptopodum |
| Rumex crispus L. var. japonicus | Iris wilsonii |
| Clerodendranthus spicatus | Solanum mammosum Linn. |
| (Thunb.) | Rheum officinale |
| Glechoma longituba | Rabdosia nervosa (Hemsl.) |
| HymenocallisSpciosa | Plumbago zeylanica L |
| Agrimonia pilosa Ledeb | Desmodium styracifolium |
| Dimocarpus longgana Lour. | Salvia substolonifera Stib. |
| Lxora chinensis | Aspidistra elatior Bl. |
| Rhapis excelsa (Thunb.) | Achyranthes bidentata Bl |
| Eranthemum pulchellum Andrews | Achyranthes bidentata Bl |
| Hypericum perforatum L | Pandanus tectorius |
| Hippeastrum rutilum(Ker-Gawl.)Herb. | Lygodium scandens (L.) Sw. Asparagus cochinchinensis |
| Pogonatherum crinitum (Thunb.) | Lonicera dasystyla |
| Kunth | Zanthoxylum nitidum |
| Echinacea purpurea Moench | Billbergia pyramidalis |
| Pseudocalymma | Ficus sarmentosa |
| alliaceum(Lam.)Sandwith | Pyrrosia drakeana |
| Sanguisorba officinalis L. | Ardisia pusilla A. DC. |
| desmodium triquetrum | Boehmeria nivea |
| Rabdosia japonica (Burm. f.) Hara | Artemisia japonica Thunb |
| Tadehagi pseudotriquetrum (DC.) | Forsythia suspensa |
| Houttuynia cordata Thunb. | Ardisia gigantifolia stapf |
| Gynura procumbens (Lour.) Merr. | Tacca chantrieri Andre |
| Vinca major Linn | Morinda officinalis How. |
| Zephyranthes carinata Herb | Ardisia villosa |
| Platycodon grandiflorus | Hemerocallis citrina Baroni |
| Aquilaria sinensis | Goodyera procera |
| Salvia cavaleriei | Fallopia multiflora |
| Datura innoxia Mill. | Campsis radicans (L.) Seem. |
| Codariocalyx gyroides | Piper longum Linn. |
| Aerva sanguinolenta | Passionfora edulis |
| Aster novi-belgii | Prunella vulgaris |
| Colocasia antiquorum Schott | Jasminum nudiflorum |
| Heteropanax fragrans | Kadsura longipedunculata |
| Thunbergia laurifolia Lindl. | Mentha haplocalyx |
| Iris germanica | Evodia lepta (Spreng.) Merr |
| Alocasia macrorrhiza | Acacia confusa Merr |
| Gelsemium elegans | Stephania kwangsiensis |
| Cocculus laurifolius DC. | Tetrastigma hemsleyanum |
| Podocarous macrophyllus | Herba Cayratica Jeponicae |
| Syzygium jambos (L.) Alston | Asarum maximum Hemsl. |
| Buddleja asiatica Lour. | Argyreia acuta Lour. |
| Buddleja davidii | Solallum nigrum L. ver |
| Caesalpinia decapetala | Curculigo capitulata |
| Jatropha gossypiifolia | Fructus Amomi |
| Peucedanum praeruptorum Dunn | Polygonum chinense L. |
| Carpesium abrotanoides Linn. | Rosa chinensis |
| Euphorbia heberophylla L | selaginella moellendorfii hieron |
| Coleus amboinicus Lour | Herba Aristolochiae |
| Lycoris aurea | Rubus cochinchinensis Tratt |
| Sauropus androgynus(L.)Merr | Rosa multiflora Thunb. |
| Houttuynia emeiensis | Rhododendron pulchrum Sweet |
| Sophora flavescens | Dichotomanthus tristaniaecarpa Kurz |
| Salvia coccinea Linn | Cycloblanopsis glaucoides Schotky |
| a plant in Tadehagi | Rhododendron anthopogonoides |
| Rhinacanthus nasutus (L.) Kurz | Maxim |
| Ardisia japonica (Thunb) Blume | Malus halliana (Voss.) Koehne |
| Trachelospermum jasminoides | Pistacia weinmannifolia |
| Wisteria sinensis | Ginkgo biloba |
| Duchesnea indica | Melaleuca bracteata |
| Ajuga decumbens Thunb | Rhododendron fuyuanense Z. H. Yang |
| Potentilla kleiniana | Ligustrumx Vicaryi |
| Pteris semipinnata L. | Euonymus Japonicus |
| Senecio cannabifolius Less | Cerasus cerasoides |
| Ophitopogin japonicum | Rhododendron 'nanhai' |
| Polygonum hydropiper L. | Rhododendron 'suimohua' |
| Pueraria lobata | Rhododendron delavayi Franch |
| Mentha spicata Linn. | Exochorda racemosa (Lindl.) Rehd |
| Lonicera fulvotomentosa | Rosmarinus officinalis |
| Acacia confusa Merr | Cotoneaster franchetii |
| Erythropalum scandens Bl. | Prunus serrulata |
| Caryota mitis Lour. | Pinus armandii Franch |
| Cirsium segetum | Pittosporum brevicalyx (Oliv.) Gagnep |
| Curcuma kwangsiensis | Osyris wightiana Wall. ex Wight |
| Artemisia argyi | Rhododendron 'mayingtao' |
| Limnophila sessiliflora | Rhododendron hancockii Hemsl. |
| Alpinia katsumadai Hayata | Rhododendron ciliicalyx Franch. |
| Blumea balsamifera DC | Amygdalus persica |
| Ficus pumila L | Abelia parvifolia Hemsl. |
| Bryophyllum pinnatum | Lonicera nitida 'Baggesens |
| Agastache rugosa | Rhodedenron schlippenbachii |
| Polygonum chinense L | Amygdalus persica f. atropurpurea |
| Jasminum amplexicaule | Pyracarltha fortuneana |
| Gnetum montanum Markgr | Trigonobalanus verticillata |
| Rhododendron pachypodum | Rhododendron 'kunming' |
| Parakmeria yunnanensis | Acer cappadocicum |
| Sinocalycanthus chinensis | Rhododendron mucronatum |
| Cerasus campanulata | Rhododendron 'fenpao' |
| Quercus variabilis Blume | Dianthus plumarius |
| Rhododendron 'Wanxia' | Musella lasiocarpa |
| Spiraea japonica L.f. | Rhododendron irroratum Franch |
| Eucommia ulmoides Oliver | Pistacia chinensis |
| Hovenia acerba | Hovenia acerba Lindl. |
| Rhododendron fortunei | Michelia lacei W. W. Smith |
| Rhododendron leptothrium | Distylium pingpienense (Hu) Walk. |
| magnolia grandiflora linn | Sedum Nicaeense All. |
| Rhododendron pachypodum | Aglaia odorata |
| Barleria cristata | Ilex crenata cv. Convexa Makino |
| Vitex negundo Linn | Rhododendron 'wanxia' |

-continued

Viburnum opulus L
Spiraea japonica L.f.
Cotoneaster salicifolius
Rhododendron alberserianum
Eriobotrya bengalensis
Cerasus clarofolia
Rhododendron vialii
Amygdalus persica Linn
Ailanthus altissima
Rhododendron taronense
Rhododendrin davidii
Sapiumsebiferum (L.) Roxb
Michelia maudiae Dunn
Rhododendron spinuliferum
Machilus yunnanensis
Liquidambar formosana Hance
Davidia involucrata Baill
Prunus salicina Lindl.
Sinomanglietia glauca
Liquidambar formosana Hance
Acer negundo L.
Magnolia soulangeana Soul.
Vinca minor Linn.
Rhododendron ciliatum Hook. f.
magnolia grandiflora linn
Trigonobalanus doichangensis
Hedera nepalensis
Quercus variabilis
Rhododendron simsii
Ilex cornuta
Fatsia japonica
Lindera communis
Pistacia weinmannifolia
Alstonia yunnanensis Diels
Machilus thunbergii
Bischofia polycarpa
Cercidiphyllum japonicum
Viburnum odoratissimum
Lamium galeobdolon
Chaenomele japonica
Spiraea blumei
Agapanthus africanus
Musella lasiocarpa
Cryptomeria fortunei
Weigela florida
Paeonia lactiflora
Parthenocissus tricuspidata
Acer palmatum 'Dissectum'
Bougainvillea spectabilis
Aesculus wangii
Mahonia fortunei
Osmanthus fragrans
Exbucklandia populnea
Cinnamomum bodinieri
Machilus longipedicellata
Ficus virens Ait.
Duranta repens Linn.
Manglietia grandis
Olea europaea L.
Parakmeria yunnanensis
Tamarix chinensis
pyrus pyrifolia
Prunus serrulata
Iris confusa
Iris wilsonii
Bambusa multiplex
Senecio scandens
Neolitsea sericea
Fokienia hodginsii
Viburnum odoratissimum
Cerasus pseudocerasus
Ilex cornuta
Fatsia japonica
Lindera communis
Pistacia weinmannifolia
Alstonia yunnanensis Diels
Machilus thunbergii
Bischofia polycarpa
Cercidiphyllum japonicum
Spiraea cantoniensis
Lorpetalum chindensevar.rubrum
Photinia serrulata
Rhododendron rigidum Franch
Rhododendron annae Franch.
Rhododendron sinogrande
Cotoneaster horizontalis Dcne
Rhododendron aberconwayi Cowan
Podocarpus macrophyllus var. maki
Rhododendron decorum Fr
Itea yunnanensis Franch.
Lonicera nitida'Maigrun'
Michelia figo
Liriodendron chinensis (Hemsl.) Sarg
Olea ferruginea Royle
Eriobotrya japonica
Luculia intermedia Hutch
Rhododendron 'jinzhizhu'
Sect. Dacrycarpus Endl
Ophiopogon japonicus cv. 'Nanus'
Ligustrum japonicum'Howardii'
Rhododendron pulchrum
Pyracantha angustifolia
Chamaecyparis lawsoniana
Cedrus deodara
Thujopsis dolabrata
Ehretia dicksonii Hance
Acer cappadocicum
Camellia sasanqua
Araucaria araucana
Ficus curtipes Corner
Manglietia duclouxii
Stranvaesia davidiana
Rhamnus gilgiana Heppl.
Agrimonia pilosa Ledeb.
Caragna fruten (L) koch
Euonymus fortunei
Pieris formosa
Fraxinus retusifoliolata
Sapindus delavayi
Elaeocarpus sylvestris
Carayaillinoensis
Micheliamacclurel
Eurya loquaiana Dunn
Ficus virens
Buxus microphylla
Lithocarpus henryi
Ficus religiosa Linn
Ligustrum lucidum
Disporopsis pernyi
Manglietiainsignis
Olea cuspidata
Hypoestes sanguinolenta
Cornus officinalis
Daphniphyllum longeracemosum
Reineckia carnea
Acorus gramineus
Cerasus cerasoides
Dipteronia dyeriana Henry
Lindera megaphylla
Liquidambar formosana Hance
Podocarpus fleuryi
Morus alba L
Zanthoxylum acanthopodium
Ficus altissima Bl.
Iresine herbstii
Cedrus deodara
Thujopsis dolabrata
Ehretia dicksonii Hance
Acer cappadocicum
Camellia sasanqua
Araucaria araucana
Ficus curtipes Corner
Manglietia duclouxii
Stranvaesia davidiana
Rhamnus gilgiana Heppl.
Agrimonia pilosa Ledeb.
Caragna fruten (L) koch -continued Viburnum odoratissimum
Lamium galeobdolon
Chaenomele japonica
Spiraea blumei
Agapanthus africanus
Musella lasiocarpa
Cryptomeria fortunei
Weigela florida
Paeonia lactiflora
Parthenocissus tricuspidata
Acer palmatum 'Dissectum'
Hypoestes sanguinolenta
Aesculus wangii
Mahonia fortunei
Osmanthus fragrans
Exbucklandia populnea
Cinnamomum bodinieri
Machilus longipedicellata
Ficus virens Ait.
Duranta repens Linn.
Manglietia grandis
Grape
Loquat
Pineapple sarcocarp
Cucumber
Chives flower
Tender leaf of Chinese toon
Bamboo shoots
Potato
Chinese lettuce
Pea shoots
Pakchoi cabbage flower
Crowndaisy chrysanthemum
Euonymus fortunei
Pieris formosa
Fraxinus retusifoliolata
Sapindus delavayi
Elaeocarpus sylvestris
Carayaillinoensis
Micheliamacclurel
Eurya loquaiana Dunn
Ficus virens
Buxus microphylla
Lithocarpus henryi
Ficus religiosa Linn
Ligustrum lucidum
Disporopsis pernyi
Manglietiainsignis
Olea cuspidata
Rhododendren simsii
Strawberry
Pineapple leaves
White gourd
Young garlic shoot
Purple cabbage
Purple Chinese cabbage flower
Cabbage lettuce
Potato sprout
Horse bean
Taro
Pakchoi cabbage
Coriander herb OxOx Activity Assay (HPLC method): The different parts of plant materials such as leaf, root, stem, fruit and flower were analyzed separately. Plant materials were homogenized with water. The soluble and insoluble fractions were collected by centrifugation. The insoluble part was re-suspended with DI water for OxOx activity analysis. 40 µl of solution or suspension was incubated with 360 µl of 12 mM oxalate in 50 mM phosphate buffer, pH 7.4, at 37° C. for 48 hours. The reaction was quenched by the addition of 100 µL 1.5 N $H_2SO_4$ (sufficient to lower the pH below 1.0, a pH at which that the enzyme is inactive). The reaction mixture was immediately centrifuged and the clear supernatant was analyzed by an HPLC method to detect oxalate. One unit of activity is defined as the amount of enzyme required to degrade 1 µmole of oxalate in one minute under the above conditions.

OxOx activity assay (colorimetric method): 20 µL solution sample is mixed into 580 µL solution containing 10 mM oxalic acid, 4 mM hydroxybenzenesulphonic acid sodium, 2 units horseradish peroxidase and 1 mM 4-anti-aminoantipyrine in 50 mM potassium phosphate buffer, pH 6.0 or 7.4, and reacted at 37° C. for 10-30 minutes. The color is monitored at 492 nm. One unit of activity is defined as the amount of enzyme required to degrade 1 µmole of oxalate in one minute under the above conditions.

This assay is specific for oxalate oxidase as an oxidase generates hydrogen peroxide which can be detected by development of color in the presence of peroxidase, while decarboxylase does not produce hydrogen peroxide.

Results

OxOx from banana peel, beet stem, Bougainvillea spectabilis leaves, Mirabilis jalapa young leaf, Telosma cordatum (Brum. f.) Merr leaf, Jatropha gossypiifolia Linn. var. elegans Mueller leaf and Sauropus androgynus (L.) Merr leaf shows significant activity at pH 7.4. All others either contain oxalate oxidase activity, but at acid pH, or no oxalate oxidase activity.

OxOx from banana peels (*Clinical Chemistry*, 1985; 31(4):649), beet Stems (*Clinical Chemistry*, 1983; 29(10): 1815-1819) has been reported in literature, but no activity around pH 7.4. It is suggested that the OxOx reported in literature may be different from these described here. As demonstrated in examples, three OxOx genes (5100, 5102, and 5601) have been isolated from sweet beet and they all have different amino acid sequence and DNA sequence, and show different properties as well. Thus, it is likely to assume that none of these OxOx is the same as the one reported in literature. Although only one OxOx gene has been cloned from banana in this work, there are dozens of similar proteins with more than 50% similarity called germin or germin-like proteins in one single plant (Critical Reviews in Plant Sciences, 2008; 27(5): 342-375). OxOx from *Bougainvillea spectabilis* leaves (Biochem. J.,1962, 85, 33) has been reported in literature and we have also identified an OxOx in our experiments. OxOx from the other four plants are first discovered in this work.

Example 2

Genes Encoding OxOx from Banana and Sweet Beet

Cloning of Oxalate Oxidase Genes from Beet Sugar and Banana

Several approaches to clone the OxOx genes from these plants have been tried. The first one is to search for public database to find if any OxOx gene has been published in the plant. Genes claimed to encode OxOx in sweet beet (GenBank: AAG36665.1) and a germin-like protein gene from banana (GenBank: AAL05886.1) are found. These genes have been synthesized and expressed by *E. coli* and yeast, and found that these genes encode SOD, not OxOx. It is not surprised, because germin SOD and OxOx (a germin as well) often share more than 50% similarity. The second approach is to design degeneration primers according to the conserved sequences of these reported OxOx to clone the targeted gene from all above 7 plants with OxOx activity at neutral pH. However, no gene encoding protein with OxOx activity was cloned. The third approach is to search the genome of banana and sweet beet that was just available in draft text. All germin and germin like protein genes were analyzed and collected from the genome data of banana and sweet beet. It has been reported that one amino acid, the Asparagine at position 75 in barley OxOx, is the key for OxOx activity (see reference J BIOL CHEM VOL. 281, NO. 10, pp. 6428-6433, 2006). There is only one such gene from banana (the gene 1013, SEQ ID NO: 15) and sweet beet (the gene 108, SEQ ID NO: 9) found, respectively. Thus, the germin genes containing this key amino acid at that corresponding position were clone and expressed by *E. coli*, yeast and plant, but no OxOx activity was detected either. After these experiments, the question is raised if these OxOx with some activity at neutral pH are germin or germin-like proteins. Thus, the forth approach is to obtain a small amount of OxOx by purification and use the protein to help finding the genes. Various efforts have been made to purify milligram levels of OxOx from these plant materials: banana peel, beet stem, *Bougainvillea spectabilis* leaves, *Mirabilis Jalapa* young leaf, *Telosma cordatum* (Brum. f.) *Merr* leaves, *Jatropha gossypiifolia* Linn. var. *elegans* Mueller leaves and *Sauropus androgynous* (L.) *Merr* leaves, which show significant activity at pH 7.4. However, only OxOx from banana peel and beet stem has been purified. The OxOx from the two plants shows similar size and subunit compositions as other germin, which indicates they are still possible germin or germin-like proteins. The purified OxOx was used to analyze amino acid sequence of peptides generated from the enzymes by mass spectrometry. Then, using the amino acid sequences to search for public database, but it did not produce any meaningful results. However, using these amino acid sequences to design degenerated primers to clone genes from sweet beet and banana. The gene 303 (SEQ ID NO: 13) and 122 (SEQ ID NO: 11) were cloned from sweet beet, but none from banana. The two genes have cloned and expressed by *E. coli*, yeast and plant, but no OxOx activity was detected from anyone. Then the purified OxOx from banana and sweet beet was used for determination of the N-terminal sequences of the proteins. The N-terminal sequences were used to search for draft genomes of sweet beet and banana to find possible genes, no meaningful gene was found. Then all matched or partly matched segments and the following DNA sequence up to several thousands base pairs were analyzed by deleting any possible introns or sequence mistakes. One gene from each plant (5601 from sweet beet and 30640 from banana) was finally found. Primers were designed to clone the genes from mRNA. One gene has been cloned from banana, but three similar genes have been cloned from sweet beet. The cloned genes were inserted in pMD19T simple vector (Takara) and sequenced to confirm their accuracy.

Results

DNA and protein sequences of beet OxOx 5100, 5102, 5601 and banana OxOx 30640.

```
SEQ ID NO: 1-5100 DNA:
ATGGTCTTTGCAATGAGCTTTACTTCTCATATTTAC-

GTGGCTTCGGCCTCTGATCCTGGTCTCCTACAGGATTTTTGTGTGGGTG-

TAAATGACCCTGATTCAGCAGTGTTTGTAAATGGAAAATTCTGCAAGAACCCAAAA-

GACGTGACAATCGACGATTTCTTATACAAAGGGTTTAATATTCCCTCAGA-

CACAAACAACACTCAAAGAGCAGAAGCCACACTAGTAGATGTCAATCGAT-

TTCCAGCACTTAACACATTAGGTGTAGCCATGGCTCGTGTAGACTTT-

GCGTCCTTTGGCCTAAACACACCTCATTTGCACCCTCGTGGTTCTGAGA-

TATTCGCGGTCCTAGAGGGGACTTTATATGCCGGCATTGTCACCACCGATAATAA-

GCTTTTCGACACGGTGTTGA-

GAAAGGGTGACATGATTGTTTTCCCTCAAGGCTTAATCCACTTCCAGCTTAATCTT-
```

-continued

GGCAAGACAGATGCTCTTGCTATTGCCTCTTTTGGGAGCCAATTTCCTGGACGAG-

TTAATGTTGCTAATGGTGTCTTTGGAACTACGCCACAAATTTT-

GGATGATGTACTTACCCAAGCGTTTCAGGTAGATAAGATGGTGATTGAG-

CAACTTCGATCTCAGTTTTCAGGTCCAAACACATCAATCAACACTGGAA-

GATCTATTCTTAAACTCTTAACTGATGTTGCT

SEQ ID NO: 2-5100 protein:
MVFAMSFTSHIYVASASDPGLLQDFCVGVNDPD-

SAVFVNGKFCKNPKDVTIDDFLYKGFNIPSDTNNTQRAEATLVDVNRFPAL-

NTLGVAMARVDFASFGLNTPHLHPRGSEIFAVLEGTLYAGIVTT-

DNKLFDTVLRKGDMIVFPQGLIHFQLNLGKT-

DALAIASFGSQFPGRVNVANGVFGTTPQILDDVLTQAFQVDKMVIEQLRSQFSGPN-

TSINTGRSILKLLTDVA

SEQ ID NO: 3-5102 DNA Sequence (w/o N-terminal signal peptide sequence, 648 bp):
TCTGATCCTGGTCTCCTACAGGATTTTTGTGTGGGTGTAAATGACCCTGATTCAG-

CAGTGTTTGTAAATGGAAAATTCTGCAAGAACCCAAAAGACGTGACAATCGAC-

GATTTCTTATACAAAGGGTTTAATATTCCCTCAGACACAAACAACACTCAAAGAG-

CAGAAGCCACACTAGTAGATGTCAATCGATTTCCAGCACTTAACACATTAGGTG-

TAGCCATGGCTCGTGTAGACTTTGCGTCCTTTGGCCTAAACACACCTCATTT-

GCACCCTCGTGGTTCTGAGATATTCGCGGTGCTAGAGGGGACTTTATATGCCGG-

CATTGTCACCACCGATTACAAGCTTTTCGACACGGTGTTGA-

GAAAGGGTGACATGATTGTTTTCCCTCAAGGCTTAATCCACTTCCAGCTTAATCTT-

GGCAAGACAGATGCTCTTGCTATTGCCTCTTTTGGGAGCCAATTTCCTGGACGAG-

TTAATGTTGCTAATGGTGTCTTTGGAACTACGCCACAAATTTT-

GGATGATGTACTTACCCAAGCGTTTCAGGTAGATGAGATGGTGATTCAG-

CAACTTCGATCTCAGTTTTCAGGTCAAAACATATCAATCAACACTGGAA-

GATCTATTCTTAAACTCTTAACTGATGTTGCT

SEQ ID NO: 4-5102 Protein Sequence (w/o N-terminal signal peptide sequence, 216 aa):
SDPGLLQDFCVGVNDPDSAVFVNGKFCKNPKDVTIDDFIYKGF-

NIPSDTNNTQRAEATLVDVNRFPALNTLGVAMARVDFASFGLNTPHLHPRGSEI-

FAVLEGTLYAGIVTTDNKLFDTVLRKGDMIVFPQGLIHFQLNLGKT-

DALAIASFGSQFPGRVNVANGVFGTTPQILDDVLTQAFQVDEMVIQQLRSQFSGPN-

TSINTGRSILKLLTDVA

SEQ ID NO: 5-5601 DNA Sequence (w/o N-terminal signal peptide sequence, 648 bp):
TCCGATCCTGCACCCCTTCAAGATTTTTGTATTGCTGTAAATGATCCCAATTCTG-

CAGTGCTTGTGAATGGAAAGCTTTGTAAGAACCCAAAAGAAGTGACAA-

TAGATGATTTCTTGTACAAAGGGTTTAATATACCTGCAGACACAAACAACAC-

TCAAGGAGCAAGTGCCACACTAGTGGACATTACTCTATTCCCTGCAG-

TTAACACACAAGGAGTCTCCATGGCTCGTGTGGACTTTGCGCCATTT-

GGACTAAACACCCCTCATTTACATCCTCGTGGCTCAGAGGTTTTCGCAG-

TGATGGAAGGGATTATGTATGCTGGTTTTGTGACCACTGATTATAAGCTCTATGATA-

CAATTATAAAAAAGGGTGA-

TATTATTGTGTTTCCACAAGGTCTAATTCATTTCCAACTTAATCTTGGGAAGA-

-continued

CAGATGCTTTAGCAATTGCCTCATTTGGGAGCCAAAATCCAGGGAGAATTAA-

TATCGCTGACAGTGTGTTTGGTACTACTCCGCGTGTTCTAGATGATGTGCTTAC-

CAAAGGATTTCAAATCGATGAGTTGTTGGTCAAGCAACTTCGTTCTCAGTTTTC-

TACTGATAATATATCAACAAGCACTGGAAGGTCATTTTTGAAATTGC-

TATCTGAAACTTAT

SEQ ID NO: 6-5601 Protein Sequence (w/o N-terminal signal peptide sequence, 216 aa):
SDPAPLQDFCIAVNDPNSAVLVNGKLCKNPKEVTIDDFLYKGFNIPADTNNTQGA-

SATLVDITLFPAVNTQGVSMARVDFAPYGLNTPHLHPRGSEVFAVMEGIMYAGFVTT-

DYKLYDTIIKKGDIIVFPQGLIHFQLNLGKTDALAIASFGSQNPGRINI-

ADSVFGTTPRVLDDVLTKGFQ1DELLVKQLRSQFSTDNISTSTGRSFLKLLSETY

SEQ ID NO: 7-30640 DNA Sequence (w/o N-terminal signal peptide sequence, 642 bp):
TTTGATCCGAGTCCTCTCCAAGACTTTTGCGTTGCTGACTACGACTCCAAC-

GTGTTTGTGAACGGATTCGCCTGCAAGAAAGCTAAGGATGTCACGG-

CAGATGACTTCTACTTCACCGGCTTAGACAAGCCCGCGAGCACCGCCAAC-

GAGCTTGGCGCAAACATCACTCTCGTCAACGTGGAAC-

GACTCCCAGGCCTCAACTCCCTTGGCGTCGCCATGTCTCGCATCGACTAC-

GCGCCCTTCGGTCTCAACCCTCCTCACTCGCATCCACGATCGTCGGAGATACTG-

CACGTGGCGGAAGGAACGCTCTACGCCGGCTTCGTCACCTCCAACAC-

GGAAAACGGCAACCTTCTCTTCGCTAAGAAGCTGAAGAAGGGCGACGCGTTT-

GTGTTCCCCAGGGGCCTCATACACTTCCAGTTCAACATCGGGGACAC-

CGATGCGGTGGCGTTCGCTACCTTCGGCAGCCAGAGCCCGGGTCTCGTCAC-

CACCGCCAACGCACTGTTCGGATCGAAGCCGCCCATCGCTGATTACATTCTT-

GCCCAGGCCGTGCAGCTTAGCAAGACGACCGTGGGCTGGCTTCAGCAGCAG-

CAGTGGTTGGACATCGCTCAAGAATATGGACAACGCTTAGTTCAAGCTAAT

SEQ ID 8-30640 Protein Sequence (w/o N-terminal signal peptide sequence, 213 aa):
FDPSPLQDFCVADYDSNVFVNGFACKKAKDVTADDFYFTGLDKPASTANELGA-

NITLVNVERLPGLNSLGVAMSRIDYAPFGLNPPHSHPRSSEILHVAEGTLYAGFV-

TSNTENGNLLFAKKLKKGDAFVFPRGLIHFQFNIGDTDAVAFATFGSQSPGLVT-

TANALFGSKPPIADYILAQAVQLSKTTVGWLQQQQWLDIAQEYGQRLVQAN

DNA and protein sequences of beet germin-like proteins 108, 122, 303 and banana germin-like protein 1013.

SEQ ID NO: 9 108 DNA sequence
ATGGCTCCCCTACTCTACCTTGTAGTATTCTTGCTT-

GCTCCTTTTCTCTCCCATGCTGCGGATCCCGATCCTTTGCTAGATTTTTGTG-

TAGCGGACCTTAATGCCTCTCCCTCATTTGCTAATTTCCCTTGCAAACAAAC-

CTCAAATGTGACCTCTGAAGATTTCTTCTTT-

GATGGGTTTATGAATGAGGGAAACACATCAAACTCGTTT-

GGATCAAGGGTCACACCCGGAAACGTCCTCACATTTCCTGCCCTTAA-

TATGCTCGGGATTTCAATGAATCGGGTTGATCTTGCTGTGGATGG-

GATGAACCCGCCCCATTCCCACCCACGAGCAAGTGA-

GAGCGGTGTGGTGATGAAGGGGAGAGTTCTAGTAGGGTTCGTAACCACGGG-

GAATGTGTACTATTCAAAGGTGTTGGTTCCAGGACAGATGTTT-

-continued

GTAATCCCAAGGGGGTTGGTTCATTTTCAAAAGAATGTTGGACAAAATAAGGCAC-

TCATCATTACAGCTTTCAATAGTCAGAATCCAGGAGTAG-

TGTTATTATCCTCAACCCTGTTTGGTACAAACCCTTCAATTCCAGATGATGTTTTAA-

GCCAAACTTTCCTAGTGGACCAGAGCATTGTCGAAGGAATAAAATCCAACTTTTGA

SEQ ID NO: 10 108 protein sequence
MAPLLYLVVFLLAPFLSHAADPDPLLDFCVADLNASPSFANFPCKQTSNV-

TSEDFFFDGFMNEGNTSNSFGSRVTPGNVLTFPALNMLGISMNRVDLAVDGMNP-

PHSHPRASESGVVMKGRVLVGFVTTGNVYYSKVLVPGQMFVIPR-

GLVHFQKNVGQNKALIITAFNS-

QNPGVVLLSSTLFGTNPSIPDDVLSQTFLVDQSIVEGIKSNF*

SEQ ID NO: 11 122 DNA sequence:
Atggaagtcgtcgcagctgtatctttctggccgtgttattggctctggtttccctgccctcgccaatgatcctgatatcttttctggccgtgttattggctctggtttccctgccctcgccaatgatcctgatatgctccaagatgtttgtgtcgctgattccacctctggagtgaaattgaatggatttgcatgcaaggatgcagcaagcattacaccagaagacttcttctttgctggaatatccaaacccggaatgacaaacaatacaatgaaatccctagtaaccggagctaacgtcgaaaagataccgggtttaaacacactcggagtgtccatgggtcgtatcgacttcggcccaggtggtcttaacccacctcacactcacccacgagccacagaaatggtctttgtgttatatggagaattggacgttggtttcctaactacttctaataagctcatttctaagcatattaaaactggtgaaacttttgttttcctagagggttagtccactttcagaaaaataatggggataaacctgctgctttagtcactgcttttaatagtcagttgcctggcacccaatcaatagctgccacgttgtttacgtcgaccccacctgttccagataatgttttaactatgactttccaagtcggtactaaacaagtccagaagatcaaggctaggctcgctcctaagaagtaa SEQ ID NO: 12 122 protein sequence:
mevvaaysflavllalvspalandpdmlqdvcvadstsgvklngfackdaasitpedfffagiskpgmtnntmkslvtganvekipglntlgvsmgridfgpgglnpphthpratemvfvlygeldvglttsnkliskhiktgetfvfprglvhfqknngdkpaalvtafnsqlpgtqsiaatlftstppvpdnvltmtf SEQ ID NO: 13 303 DNA sequence:
Atggcggctgtttgggtagtcttggtggtgctagcggcggcttttgctgttggggtcttttgccagcgatcctgatatgcttcaagatgtttgtgttgctgatcgtacatctggaatattagtgaatggattcacatgtaaaaatatgaccatgataacccctgaagacttcttcttcaccggaatttcacaaccaggccaaatcacaaataaaatccttggttctcgagtcaccggagcgaatgtgcaggacatccctggtctcaacacctttgggagtctcgatggctcgtgtcgactttactccctacggtctaaacccacctcacattcacctagaatcgtccaccctcgtgccactgaaatgatctatgttcttaagggtgaattgtacgttggttttataacgaccgacaataagctcatttccaaggttgttaaagctggagaagtatttgttttccctagagggtttggctcactttcagaaaaacatgttgaaatatccagctgctgcattagctgccttcaacagccaacttccaggcactcaacaatttgcagctgctctcttacttccaatcctcctgtgtctaatgatgtgttggctcaggcttttaacattgacgaacacaatgtcaaaaagattagggctg -continued SEQ ID NO: 14 303 protein sequence:
MAAVWVVLVVLAAAFAVGVFASDPDMLQDVCVADRTSGILVNGFTCKNMTMITPED-

FFFTGISQPGQITNKILGSRVTGANVQDIPGLNTLGVSMARVDFTPYGLNP-

PHIHPRATEMIYVLKGELYVGFITTDNKLISKVVKAGEVFVFPRGLAH-

FQKNMLKYPAAALAAFNSQLPGTQQFAAALFTSNPPVSNDVLAQAFNIDEHNVK-

KIRAGLTP

SEQ ID NO: 15 1013 DNA sequenc
ATGGAGTCGCACTACACGAAGAGACCATTCCTCCTCTTTCTCTCCTTCAC-

CGTCCTCCTCGTGTTGATCCGCGCTGACCCTGATCCTCTCCAG-

GACTTCTGCGTCGCCGACCTCGGAGCTACTGTGGTCGTCAATGGGTTCCCGTG-

CAAGCCCGCGTCCGGAGTCACGTCCGACGACTTCTTCTTCGCCG-

GACTGTCCAGGGAGGGCAACACCAGCAATATCTTCGGGTCCAACGTGACCAAC-

GCCAACATGCTCAGCTTCCCGGGGCTCAACACCCTCGGCGTCTCCATGAAC-

CGCGTCGACGTCGCCCCCGGCGGCAC-

CAACCCGCCCCACAGCCACCCGAGGGCTAC-

CGAGCTCATCATCCTCCTCAAGGGCCGGCTGCTGGTGGGGTTCATCAGCACCAG-

TAACCAGTTCTTCTCCAAGGTCTTGAACCCCGGCGA-

GATGTTCGTGGTGCCCAAGGGGCTCATCCACTTCCAGTACAACGTCGGCAAGGA-

GAAGGCGCTCGCCATCACCACCTTCGACAGCCAGCTCCCCGGAGTAG-

TGATCGCCTCCACCACCCTGTTCGCATCGAATCCGGCGATTCCCGAC-

GATGTGCTGGCCAAAGCTTTTCAGGTGGAC-

GCGAAGGTCGTCGCTCTCATCAAGTCCAAGTTTGAGAGATAA

SEQ ID NO: 16 1013 protein sequence
MESHYTKRPFLLFLSFTVLLVLIRADPDPLQDFCVADLGATVVVNGFPCKPASGV-

TSDDFFFAGLSREGNTSNIFGSNVTNANMLSFPGLNTLGVSMNRVDVAPGGTNP-

PHSHPRATELIILLKGRLLVGFISTSNQFF-

SKVLNPGEMFVVPKGLIHFQYNVGKEKALAITTFDSQLPGVVIASTTL-

FASNPAIPDDVLAKAFQVDAKVVALIKSKFER*

Example 3

Recombinant Expression of Oxalate Oxidase by *E. coli*
Part 1. Plasmid Construction and Protein Expression
Expression Plasmid Construction:

The pAT plasmid was produced by deleting the DNA sequence between the 212$^{th}$ bp and the 729$^{th}$ bp of the pET-32 vector. The 5102, 5100, 5601 and 30640 genes were then ligated into the modified pET-32 vector (pAT) using the NcoI and XhoI restriction sites. The resulting plasmids were then transformed into *E. coli* Origami B competent cells, which are designed to be favorable for disulfide bond formation of expressed proteins, since there is one disulfide bond within each OxOx monomer and it is essential for the protein native structure as well as enzyme activity. See FIG. 1.

Protein Production in Small Scale:

Cells were grown at 37° C. in 200 mL LB medium (10 g tryptone, 5 g yeast extract, and 10 g NaCl in 950 mL deionized water.) supplemented with 100 µg/mL ampicillin. When OD$_{600}$ reached 0.6~0.8, expression was induced for 4 h at 37° C. after addition of IPTG and MnCl$_2$ to a final concentration at 0.6 mM and 1 mM, respectively. Cells were collected by centrifugation at 9,500 rpm for 10 min and suspended in 50 mM arginine buffer and then sonicated on ice. The insoluble matter was washed twice with 50 mM arginine, and collected by centrifugation for 15 min at 9,500 rpm. The insoluble material contains about 80% of OxOx inclusion body.

Protein Production in Large Scale:

For large-scale production of OxOx proteins, *E. coli* Origami B cells were grown in a 7 L fermenter (3.5-L working volume) in LB medium supplemented with 100 µg/mL ampicillin and 5 mM MnCl2. The initial glycerol and yeast extract concentrations were 12 g/L. Fermentation was carried out at 30-37° C. with vigorous aeration and agitation and the pH of the medium was maintained at 6.85 by addition of 10% ammonia. After 8 h of batch growth, the cells were grown in a fed-batch mode with a continuous supply of glycerol and yeast extract. The culture at OD$_{600}$ of 20 was induced with 0.8 mM IPTG, cultivated for another 20 h, and then harvested.

Part 2. Protein Refolding

*E. coli* cells were broken by homogenizer or sonication. OxOx inclusion body was obtained by washing the broken cells and collected by slow speed centrifugation, which is well known by scientists in the field. The purified inclusion body was dissolved in 8M urea, pH 8.0. The soluble fraction was obtained following incubation at room temperature for 20 min followed by centrifugation.

Proteins were refolded by rapid dilution:

Inclusion bodies were dissolved in 8 M urea, pH 8.0. Rapid dilution was achieved by adding the 8 M urea OxOx solution drop-wise into refolding buffer with rapid stirring. The refolding buffers we have used:
1. 20 mM Tris, 300 mM NaCl, 1 mM $MnCl_2$, 1 mM GSH/0.2 mM GSSG, pH 8.0
2. 20 mM Tris, 300 mM NaCl, 1 mM $MnCl_2$, 1 mM GSH/0.2 mM GSSG, 400 mM arginine, pH 8.0
3. 20 mM Tris, 300 mM NaCl, 1 mM $MnCl_2$, 1 mM GSH/0.2 mM GSSG, 100 mM α-cyclodextrin, pH 8.0
4. 20 mM Tris, 300 mM NaCl, 1 mM $MnCl_2$, 1 mM GSH/0.2 mM GSSG, 2% b-cyclodextrin, pH 8.0
5. 20 mM Tris, 300 mM NaCl, 1 mM $MnCl_2$, 1 mM GSH/0.2 mM GSSG, 40% sucrose, pH 8.0
6. 20 mM Tris, 300 mM NaCl, 1 mM $MnCl_2$, 1 mM GSH/0.2 mM GSSG, 40% glucose, pH 8.0
7. 20 mM Tris, 1 mM $MnCl_2$, 1 mM GSH/0.2 mM GSSG, pH 8.0
8. 20 mM Tris, 1 mM $MnCl_2$, 1 mM GSH/0.2 mM GSSG, 400 mM arginine, pH 8.0
9. 20 mM Tris, 1 mM $MnCl_2$, 1 mM GSH/0.2 mM GSSG, 50 mM betaine, pH 8.0
10. 20 mM Tris, 1 mM $MnCl_2$, 50 mM betaine, pH 8.0
11. 20 mM Tris, 0.5-5 mM $MnCl_2$, 1 mM GSH/0.2 mM GSSG, 50 mM betaine, pH 8.0
12. 20 mM Tris, 1 mM $MnCl_2$, 1 mM GSH/0.2 mM GSSG, 50 mM betaine, pH 4.0-10.0
13. 20 mM Tris, 1 mM $MnCl_2$, 50 mM betaine, 0.05 mM 1-hexanol, 50 mM acetamide, 300 mM KCl, pH 8.0

Results:
1. OxOx from banana is expressed as inclusion body with a yield in the range of 0.2-0.6 gram per liter of culture in a flask, 2-6 gram per liter of culture in a fermentor. The production yield can be improved after optimization of conditions. The inclusion bodies usually show a little OxOx activity, but after refolding, a specific activity in the range of 0.1 to 10 units per mg of protein is readily obtained after purification with Phenylsepharose column.
2. OxOx 5100 from sweet beet is expressed as inclusion bodies with a yield in the range of 0.1-0.5 gram per liter of culture in a flask, 1-5 gram per liter of culture in a fermentor. The production yield can be improved after optimization of conditions. The inclusion bodies usually show a little OxOx activity, but after refolding, a specific activity in the range of 0.1 to 15 units per mg of protein is readily obtained after purification with Phenyl-sepharose column.
3. OxOx 5102 from sweet beet is expressed as inclusion bodies with a yield in the range of 0.1-0.5 gram per liter of culture in a flask, 1-5 gram per liter of culture in a fermentor. The production yield can be improved after optimization of conditions. The inclusion bodies usually show a little OxOx activity, but after refolding, a specific activity in the range of 0.1 to 10 units per mg of protein is readily obtained after purification with Phenyl-sepharose column.
4. OxOx 5601 from sweet beet is expressed as inclusion bodies with a yield in the range of 0.1-1 gram per liter of culture in a flask, 1-10 gram per liter of culture in a fermentor. The production yield can be improved after optimization of conditions. The inclusion bodies usually show a little OxOx activity, but after refolding, a specific activity in the range of 0.1 to 10 units per mg of protein is readily obtained after purification with Phenyl-sepharose column.
5. The refolding conditions have not been optimized, but it has been observed that refolding buffer pH at 8.0, stabilizers or solubility enhancers including betaine, NaCl or KCl, acetamide, and 1-hexanol, and the concentration of $MnCl_2$ around 1 mM. are important for effective refolding.

Example 4

Recombinant Expression of Oxalate Oxidase by *P. pastoris*

Expression Vector Construction

The genes of beet 5102 and 5601 and banana 30640 were amplified from a pMD18-T simple vector containing these genes using a pair of primers designed to introduce an Xho I followed by a Kex2 protease cleavage site at the 5' and an Not I restriction site at the 3' (Table 1). The PCR products were digested with Xho I and Not I and cloned into the pPICZαB and pGAPZαA vectors digested with the same restriction enzymes, resulting in the recombinant plasmids of Zα-5102, GAPZα-5102, Zα-5601, GAPZα-5601, Zα-30640 and GAPZα-30640 (FIGS. 2-7). The recombinant plasmids of Zα-5102, Zα-5601 and Zα-30640 were linearized with Pme I (Mss I) and GAPZα-5102, GAPZα-5601 and GAPZα-30640 were linearized with Bln I (Avr II). Then, all the linearized vectors were electro-transformed into *P. pastoris* X-33 according to the methods of high efficiency transformation of *P. pastoris* pretreated with lithium acetate and dithiothreitol, which recommended by Wu S and Letchworth GJ (2004

TABLE 1

Primers used to construct expression vectors

| SEQ ID NO: | Oligo-nucleotides | Sequence (5' to 3') |
|---|---|---|
| 17 | 5102F | CCGCTCGAGAAAAGATCTGATCCTGGTCTCCTACAG |
| 18 | 5102R | AAATATGCGGCCGCTCAAGCAACATCAGTTAAGAGTT |
| 19 | 5601F | CCGCTCGAGAAAAGATCCGATCCTGCACCCCTT |
| 20 | 5601R | AAATATGCGGCCGCTCAATAAGTTTCAGATAGCAATTTC |
| 21 | 30640F | CCGCTCGAGAAAAGATTTGATCCGAGTCCTCTCCA |
| 22 | 30640R | AAATATGCGGCCGCTCAATTAGCTTGAACTAAGCGTTG |

Protein Expression

Positive clones were initially selected by YPDS medium plates (10 g/l yeast extract, 20 g/l peptone, 20 g/l dextrose, 1 M sorbitol, and 20 g/l agar) containing 100 μg/ml Zeocin. Then, multiple-copy transformants were further screened by YPDS resistance plates containing Zeocin at a final concentration of 1 mg/ml. The selected colonies were checked first with PCR and then sequencing to verify a right gene inserted into yeast chromosome. The high Zeocin resistance clones were selected to check their expression by shaking flask fermentation.

The growth and induction media in shaking flask were BMGY (yeast extract 1% (w/v), peptone 2% (w/v), 100 mM potassium phosphate buffer at pH 6.0, yeast nitrogen base with no amino acids 1.34% (w/v), glycerol 1% (w/v), biotin 0.04% (w/v)) and BMMY (its composition is similar to BMGY, but with 1.0% (v/v) methanol instead of glycerol). A single colony of a selected strain was first inoculated into a 20 ml bottle with 4 mL YPD medium and grew at 28° C. for 18-20 h. Then, 4% (v/v) of the culture was inoculated into a 500 ml flask containing 50 ml (or 250 ml flask containing 25 ml) BMGY. The cells were grown at 28° C., shaking at 220 rpm, for 18-20 h to reach an $OD_{600}$ of 3.0-6.0, then harvested by centrifugation and re-suspended in 50 mL BMMY medium containing 5 mM $MnCl_2$ for methanol induction. The induction temperature was set at 28° C., and 100% methanol was added daily to reach methanol concentrations at 1.0% (v/v). After 96-120 h methanol induction, the supernatant of the culture was collected by centrifugation at 9500 rpm for 5 min at 4° C., and used for OxO activity assay and SDS-PAGE. Proteins were stained with Coomassies Brilliant Blue R-250. All the supernatant samples were concentrated by TCA precipitation. All the samples used for SDS-PAGE analysis are 30 µl of concentrated supernatant. For the constructive expression of GAP promoter, the growth was BYPD medium (10 g/l yeast extract, 20 g/l peptone, 20 g/l glucose, biotin 400 µg/l, $MnCl_2$ 5 mM and 100 mM potassium phosphate buffer, pH 6.0) and the cells were grown at 28° C., shaking at 220 rpm. Add 2% glucose into BYPD medium after 48 h of culture. After 72 h of culture, the supernatant of the culture was collected and analyzed as above conditions Fed-batch fermentation: Inoculum (any recombinant yeast culture described above) was produced at 30° C. in a 2 l flask containing 400 ml YPD medium shaken at 220 rpm for 18 h. Then, 10% (v/v) of the inoculum was inoculated into the 7 l fermentor containing 2.8 l FM22 medium ($KH_2PO_4$, 42.9 g/l; $(NH_4)_2SO_4$, 5 g/l; $CaSO_4.2H_2O$, 1.0 g/l; $K_2SO_4$, 14.3 g/l; $MgSO_4.7H_2O$, 11.7 g/l; glycerol, 40 g/l and 2.5 ml/l PTM4 trace salt solution). PTM4 trace salt solution. The PMT4 solution was composed of (g/l): $CuSO_4.5H_2O$, 2.0; NaI, 0.08; $MnSO_4.H_2O$, 3.0; $Na_2MoO_4.2H_2O$, 0.2; $H_3BO_3$, 0.02; $CaSO_4.2H_2O$, 0.5; $CoCl_2$, 0.5; $ZnCl_2$, 7; $FeSO_4.7H_2O$, 22; biotin, 0.2 and 1 ml/l concentrated $H_2SO_4$ [18]. The glycerol fed-batch solution contained ($l^{-1}$): 500 g glycerol (100%)and 4 ml PTM4 stock solution. The methanol fed-batch solution consisted of 4 ml PTM4 stock solution and 1 l of pure methanol. Once glycerol was depleted from culture broth, an 8 h glycerol exponential fed-batch phase was started at a growth rate of 0.16 $h^{-1}$. The methanol limited fed-batch strategy was carried out at the end of glycerol transition phase. Methanol feeding rate was regulated to maintain the DO above the set point in the culture broth according to the recommendations of Pichia Fermentation Process Guidelines (Invitrogen). The temperature was set at 30° C. at the glycerol batch and fed-batch phases, and then decreased to 25° C. at the beginning of the methanol induction phase. The pH value was kept at 5.5 by addition of 28% (w/w) ammonium hydroxide. The DO level was maintained at 20-50% of air saturation by a cascaded control of the agitation rate at 500-800 rpm with an airflow rate of 150-400 l/h. Foaming was controlled through addition of antifoaming agent (Dowfax DF103, USA). The fed-batch feeding medium was pumped into the fermentor according to a predetermined protocol.

Purification of Recombinant Protein

The purification procedure was basically done as follow: the cell-free fermentation broth containing the secreted enzyme was concentrated and dialyzed overnight against 50 mM potassium phosphate and citric acid buffer pH 3.5 and then loaded into a cation exchange column, or dialyzed overnight against 50 mM potassium phosphate and citric acid buffer pH 7.5 and then loaded into an anion exchange column. If not sufficient, a phenyl-sepharose column is applied. The flow-through fractions were pooled and concentrated by ultra-filtration for SDS-PAGE and activity assay.

Results

The three oxalate oxidase genes of 5102, 5601 and 30640 have been successfully expressed in *P. pastoris* with a yield in a range of 0.01-1 mg per liter of culture, as shown by SDS-PAGE with a band at molecular weight of 24 kD (FIGS. 8-11). Oxalate oxidase purified from the broth, all of them showed oxalate degradation activity at pH 7.4.

Example 5

Production of Oxalate Oxidases in Plants by Transient Expression

Construction of Expression Vectors

The genes for transient expression (5601 and 5102 from sugar beet, 30640 from banana) were amplified by gene-specific primers flanked by restriction sites XbaI and KpnI. After XbaI and KpnI digestion, the amplified fragments (FIGS. 12-13) were cloned into pHTE to produce pHTE-5601, pHTE-5102 and pHTE-30640 (FIG. 14), respectively. All positive recombinant plasmids were selected by colony PCR or by enzyme digestion and separately introduced into the *A. tumefaciens* strain GV3101 by the freeze/thaw method 5.1 Transient Expression in Tobacco Leaves Plant Materials Wild-type *N. benthamiana* plants were grown in a greenhouse with a 16/8 hr light/dark cycle at 25° C. for 5 to 8 weeks.

5.1.1 Bacterial Culture and Suspension Preparation

1. Pre-cultures are prepared 2 days before infiltration by inoculating 3 mL of LB medium (10 g tryptone, 5 g yeast extract, and 10 g NaCl in 950 mL deionized water.) containing 25 mg/L rifampicin and 50 mg/L kanamycin with isolated colonies of *Agrobacterium* strains harbouring expression plasmids, overnight at 28° C. under constant agitation at 220 rpm to grow preferentially to an OD (600 nm)>1.2.

2. Inoculate fresh LB medium containing 25 mg/L rifampicin, 50 mg/L kanamycin and 20 µM acetosyringone with pre-culture at 1:100 ratio. For each plant to be infiltrated, 20 mL of each strain should be prepared. The cultures were incubated at 28° C. under constant agitation at 220 rpm to an OD (600 nm) of 0.8-1.2 (~18 h).

3. Centrifuge cultures (5000 rpm; 5 min) and discard supernatant.

4. Resuspend the bacterial pellets in 5 volume of bacteria resuspension solution (10 mM 2-N-morpholinoethanesulfonic acid (MES)) pH 5.5, 10 mM $MgSO_4$, and 100 mM acetosyringone), and incubate for 4 h at room temperature before use.

5.1.2 Syringe Infiltration and Plant Incubation

1. Fill a 1 mL- or 3 mL-syringe (without needle) with bacterial suspension, and hold the leaf to be infiltrated between the index and the syringe, the syringe being on the abaxial side of the leaf. Gently push the piston to force the bacterial suspension enter into the leaf and maintain an even pressure during the infiltration. Wetting of the leaf surrounding the infiltration point is observed as the suspension enters the tissue in the apoplastic space. For each point of infiltration, a surface of ~7 cm² should be filled. Several points of infiltration may be necessary to completely inoculate each leaf.

2. Infiltrate a maximum number of leaves on each plant and remove all uninfiltrated leaves as well as apical and axillary buds to avoid growth of non-infiltrated leaves during the incubation period.
3. Incubate infiltrated plants in the greenhouse for 7 days, watering the plants as needed and continuing nitrogen fertilization.

5.1.3 Leaf Disk OxOx Activity Assay

Agroinfiltrated tobacco leaves were harvested 7 days post infiltration (dpi) for OxOx activity assays. Histochemical assay of OxOx activity was carried out. The histochemical buffer contains 40mM succinate, 2.5 mM oxalic acid, 5 U/ml horseradish peroxidase, 0.6 mg/ml 4-chloro-1-naphthol, 60% (V/V) ethanol, pH 5.0. Leaf discs were added to the buffer and viewed following incubation at room temperature overnight. The control is the leaf discs made from the same way as the tested leaf discs except that no OxOx gene agroinfiltrated into tobacco leaves.

The results are given below together with the results from the experiments relating to transient expression in pea 5.2 Transient Expression in Pea 5.2.1 Plant Materials The seeds of pea plant (*P. sativum*) were obtained from the local market. The seeds were sowed and plants were grown in a plant growth chamber at 25° C. under a 16 h cool fluorescent light/8 h dark cycle.

5.2.2 Bacterial Culture, Suspension Preparation and Vacuum-infiltration

Agrobacterium GV3101 cultures, bearing binary vectors, were grown in modified YEB media (6g/L yeast extract, 5 g/L peptone, 5 g/L sucrose, 2 mM $MgSO_4$) with antibiotics (100 mg/mL of kanamycin, 50 mg/mL of rifampicin,) for 2 days at 28° C. For final scaled up growth, initial 2-day cultures were diluted 1:100 in the same YEB medium supplemented with antibiotics, 10 mM IViES, pH 5.6, 20 µM of acetosyringone and allowed to grow 18-24 h to an $OD_{595}$ nm of about 2.4. Bacterial cells were supplemented with 55 g/L of sucrose and 200 µM acetosyringone and the suspension was incubated for 1 h at 22° C. TWEEN® 20 were added to final concentrations of 0.005% and the suspension was used for vacuum-infiltration. An amount of 1.2 L of pretreated suspension of Agrobacterium was placed into a 2 L glass beaker inside a vacuum. The whole pea plants were immersed into the suspension and held for 1 min under vacuum (0.07-0.1 MPa) and the vacuum was rapidly released. The pea plant roots were rinsed in water and left for 5-7 days at 20-22° C. with 16 h light every day. After 5-6 days of incubation, the pea plants were cut out from the base and homogenized for protein extraction.

5.2.3 Enzyme Assay

For analysis of protein expression levels, protein was extracted with extraction buffer (50 mM citric acid-phosphate, pH 7.0). The extraction buffer and harvested pea plants were in a 1:1 (v/w) ratio. The tissues were cut from the base and homogenized in a blender at high speed for 1 min. Homogenate was centrifuged for 15 min at 7000 g. The supernatant was centrifuged for 15 min at 14,000 g and the resulting supernatants were analyzed by 12% SDS-PAGE gel. The pellet was washed twice by re-suspension in 10 vol. of the homogenization medium containing 1% (w:v) TRITON™ X-100 and four times with 30 vol. of the same medium without TRITON™ X-100. After each wash the pellet was collected by centrifugation at 1000 g for 10 min.

The final pellet was considered to be the purified cell wall fraction, and was used for testing the OxOx activity by colorimetric assay. For purification of OxOx, the supernatant of centrifuged homogenate was precipitated with 80% saturated ammonium sulfate. The pellet was re-dissolved in 50 ml buffer A (50 mM citric acid-phosphate, pH 6.0, 2M NaCl), and the resulting suspension was centrifuged for 20 min at 14,000 g. The resulting supernatant was loaded onto Phenyl Sepharose HP column previously equilibrated with buffer A. The protein was eluted with a linear gradient of NaCl (2-0 M) in the same buffer and fractions were collected at a rate of 0.5 ml/min. The collection fractions were detected the OxOx activity by colorimetric assay. Then the fractions having OxOx activity were mixed together and reloaded on a Q Sepharose column. OxOx was eluted with a liner gradient of NaCl (0-2 M) in buffer A. All the collection fractions were tested OxO activity by colorimetric method.

Results

1. The genes of OxOx 5102, 5601 and 30640 have been amplified (FIGS. 12-13)
2. The plant expression vector for OxOx 5102, 5601 and 30640 (FIG. 14)
3. The genes for OxOx 5102, 5601 and 30640 are expressed with OxOx activity in tobacco leaves (FIG. 15)
4. The genes for OxOx 5102, 5601 and 30640 are expressed with OxOx activity in pea leaves (FIG. 16)
5. OxOx 5102 expressed by pea leaves has been purified and shows activity (FIGS. 17 and 18)
6. The expression levels of OxOx 5102, 5601 and 30640 by pea leaves in the range of 0.01-5 mg per gram of fresh leaves, but majority of the expressed OxOx is associated with the solid material (FIG. 16)

Example 6

The Activity of Oxalate Oxidases Expressed by *E. coli* at Different pH

Activity Assay: the enzyme solution 10 µl is added to 190 µl of 800 mg/L 4-Aminoantipyrine, 4.8 mM sodium 3,5-dichloro-2-hydroxybenzenesulfonate, 10 unit per ml horseradish peroxidase, 5 mM oxalate, 50 mM phosphate.

The mixture is placed at 37° C. for 10-60 min in a plate reader to read $OD_{600}$. One unit of activity is defined as the enzyme amount required to produce 1 µmole of formate from oxalate under the above conditions.

Activity pH profile: samples were tested as described earlier using a series of buffers within a pH range of 4.5-8.0 (50 mM citrate for pH 4.5-6.0 and 50 mM potassium phosphate for pH 6.0-8.0).

This test is used to test the oxalate oxidases for oxalate degrading activity as referred to in the claims.

Results

The maximum activity is 18.2 units per mg for 5100, 19.5 units per mg for 5102, 18.7 units per mg for 5601, and 14 units per mg for 30640. For easy comparison, the activity for each enzyme at different pH is given in the table 1 and FIG. 19 as relative activity, which is calculated by the activity divided by the maximum activity.

TABLE 1

| The relative activity of OxOx at pH 4.5-8 | | | | |
|---|---|---|---|---|
| pH | 5100 | 5102 | 5601 | 30640 |
| 4.5 | 69.23 | 83.42 | 45.10 | 45.52 |
| 5 | 88.08 | 91.23 | 79.34 | 69.11 |

TABLE 1-continued

The relative activity of OxOx at pH 4.5-8

| pH | 5100 | 5102 | 5601 | 30640 |
|---|---|---|---|---|
| 5.5 | 92.95 | 94.30 | 100.00 | 80.37 |
| 6.0 | 99.99 | 96.17 | 77.60 | 97.92 |
| 6.5 | 92.60 | 100.00 | 49.20 | 99.99 |
| 7.0 | 90.69 | 95.10 | 36.73 | 92.56 |
| 7.5 | 82.00 | 92.60 | 21.78 | 65.33 |
| 8.0 | 81.75 | 87.50 | 18.17 | 42.17 |

Example 7

Inclusion Body Washing—OxOx-B5102

The harvested cell pellets were resuspended in a ratio of 30 g cell paste per 1L wash buffer (50 mM Tris-HCl, 2M urea, 50 mM NaCl, 5 mM EDTA, 5 mM DTT, pH 8.0). Benzonase nuclease (100 units per liter with 0.5 mM $MgCl_2$) was added to cell suspension to digest *E. coli* nucleic acid (including DNA and RNA), incubated at 37° C. for 15 min. The pre-treated cells were passed through a pre-cooled homogenizer (NTI, USA) 4 times at 1100 bar pressure, then centrifuged at 8000 g for 10 min in 500 ml bottles at 4° C. The pellets were resuspended and washed with wash buffer 3 times and deionized water twice. The purity of inclusion body was analyzed by SDS-PAGE. The purity of the inclusion body usually reached above 80%.

Example 8

Q-Sepharose Purification of Inclusion Body

The washed inclusion body from Example 7 with purity>80% was dissolved in urea buffer (20 mM Tris-HCl, 8M urea, pH 8.0), and centrifuged at 13000 g for 10 min. The supernatant was loaded on pre-balanced Q-sepharose column with the urea buffer and further washed 5 column volumes (CV) with the same buffer. The impurity was eluted by elution buffer B (8M urea, 30 g/L NaCl, Tris-HCl, pH 8.0) with 6 CV. The OxOx-B5102 protein was eluted by elution buffer C (8M urea, 160 g/L NaCl, Tris-HCl, pH 8.0). The purity of OxOx-B5102 inclusion body after Q-sephrose column purification usually reached above 95%. The purified OxOx-B5102 inclusion body solution was concentrated to 5 mg/mL for protein refolding by 10K ultra-filtration tubes.

Example 9

Refolding of Inclusion Body
Refolding was performed as described herein before.

Example 10

Phenyl Sepharose Purification of OxOx-B5102

NaCl was added to the refolded OxOx-B5102 mixture to a final concentration of 500 mM, and then passed through 0.45 μm membrane. The clarified OxOx-B5102 solution was loaded into Phenyl sepharose column pre-balanced with 5 CV of balance buffer (10 mM Tris-HCl, 500 mM NaCl, pH 8.0). The column was further washed with 1.5 CV of wash buffer (10 mM Tris-HCl, 250 mM NaCl, pH 8.0), and then OxOx-B5102 was eluted by elution buffer (10 mM Tris-HCl, 20% Isopropanol, pH 7.0). The target protein was precipitated by adding NaCl to the solution up to 50 mM and collected by centrifugation at 12000 g for 10 min, 4° C. The pellets were re-dissolved in borate buffer (10 mM $Na_2B_4O_7$~$H_3BO_3$, pH 9.0) for PEGylation. The purity of collected OxOx-B5102 sample was analyzed by SDS-PAGE, the activity of OxOx-B5102 was analyzed by activity assay.

Example 11

PEGylation and Purification of PEG-OxOx

The concentration of OxOx-B5102 in borate buffer was adjusted to 2 mg/mL for pegylation. A ratio of 10 times of PEG molecules over the number of lysine residues on OxOx surface was used for pegylation reaction. Different sizes of Methoxy PEG Succinimidyl Carboxymethyl Ester (mPEG-SC) at 2 kD, 5 kD, 10 kD, 20 kD, 4 armed-20 kD, 30 kD, 40 kD and 4 armed-40 kD were tested one by one. The mPEG-SC was gradually added into OxOx-B5102 solution and gently mixed by using magnetic stirrer. The reaction was maintained for 6 h at 28° C., and then was stopped by adding glycine.

The pegylated OxOx-B5102 sample was loaded on size exclusion chromatography (GE HiLoad Superdex 16/600GL, USA) pre-balanced with phosphate buffer (10 mM $K_2HPO_4$~$KH_2PO_4$, pH 7.4) and eluted by the same buffer at an elution rate of 1 mL/min. The target protein was collected.

Example 12

Reduction of Plasma Oxalate and Urine Oxalate in Rat Model 30 male Sprague Dawley (SD) rats, weighing approximately about 130-150 g and less than 5 week were purchased from local animal experimental center. Rats were housed in a plastic individual ventilated cage (IVC) system (temperature 18~26° C., moisture 40~70%) and fed with distilled water and regular rat food every day. After 1 week of acclimatization, Rats were randomly divided into control group and 4 experimental groups (six rats per group) and transferred to metabolic cages with single occupation. Rats in control group were fed regular food and water; the experimental groups were fed with regular food and 1% ethylene glycol as drinking water. Blood sample (about 0.3 ml) was collected from tail-vein and heparin was added into blood as anticoagulant. Serum was obtained immediately from fresh blood sample by centrifugation at 5000 g for 5 min at 4° C. Urine sample was collected from urine collection tube of metabolic cage every 12 h (8:30 and 20:30) and acidified by using 2M HCl immediately to pH 1.5~2.0. Serum and urine oxalate of all rats was detected and monitored until oxalate level was stable, then PEG-OxOx-B5102 was injected through vein.

Serum oxalate was analyzed by using 10-acetyl-3,7-dihydroxyphenoxazine (Amplex red) fluorescence method. The procedure: fresh serum samples were acidified to pH 2.0 and serum proteins were removed by filtration with 10K ultra-filtration tube. The filtrate (10 μl) was added to 96 well multi-plate for 6 wells. The reaction buffer containing oxalate oxidase (100 mM citrate buffer, pH 5.4, 10 μM Amplex red, 1U/mL HRP, 0.1U/mL OxOx-B5102) were added into 3 wells and the background reaction buffer without OxOx (100 mM citrate buffer, pH 5.4, 10 μM Amplex red, 1U/mL HRP) was added into the other 3 wells. All reactions were incubated at 25° C. for 30 min, then fluorescence of each well was detected by using fluorescence multi-plate reader (excitation wavelength: 538 nm; emission wavelength: 590 nm). The fluorescence of a sample is the average value of the three wells after minus the average of the three background control wells. Oxalate concentration was calculated by fluorescence value, which was calibrated by oxalate standard curve.

Urine oxalate concentration was detected by using colorimetric assay (adopted commercially available Trinity oxalate kit). The operation procedure was done according to the manual of the kit.

Following the acclimation period, OxOx-B5102 pegylated with 3 different molecular weights of PEG (20 kD, 30 kD, and 40 kD PEG) was administered to rats in 3 experiment groups, respectively, 0.2 mg OxOx each time per rat, for consecutive 3 days. Saline was administered to rats in the fourth experiment group, recorded as placebo control group at same dose. Rats in regular control were fed as usual without any treatment. Serum oxalate and urine oxalate was monitored every day. The results showed that PEG-OxOx-B5102 could reduce 40~50% serum oxalate and 20~40% urine oxalate compared with placebo control (FIG. 21 and FIG. 22).

Example 13

Immunogenicity Evaluation of PEG-OxOx-B5102s

OxOx-B5102 and OxOx-B5102 pegylated with different molecular weights of PEG (2 kD, 5 kD, 10 kD, 20 kD, 30 kD and 40 kD) were injected intraveneously into SD rats for immunogenicity evaluation, respectively, through tail veins every week for 4 weeks. The dose was 0.2 mg OxOx each time. Serum samples were collected and detected antibody titer by using ELISA method.

The ELISA method procedure: (1) rat serum samples were collected at different timepoints (0 d, 7 d, 14 d, 21 d, 28 d, 45 d, 60 d) post injecting of PEG-OxOx-B5102 and stored at −20° C. until use. (2) Dilute OxOx-B5102 to a final concentration of 10 μg/ml in coating buffer (50 mM carbonate/bicarbonate buffer, pH 9.6) and transfer 100 μl to each well of a high affinity, protein-binding ELISA plate. Cover the plate with a tinfoil and incubated at 4° C. overnight. (3) Bring the plate to room temperature, flick off the capture antibody solution, wash 3 times with PBS-T buffer (1.5 mM $KH_2PO_4$; 8.1 mM $Na_2HPO_4.12H_2O$; 136 mM NaCl; 2.7 mM KCl; 0.05% TWEEN® 20), and block non-specific binding sites by adding 300 μl of blocking solution (1.5 mM $KH_2PO_4$; 8.1 mM $Na_2HPO_4.12H_2O$; 136 mM NaCl; 2.7 mM KCl; 5% non-fat dry milk) to each well. (4) Seal plate and incubate at 37° C. for 1~2 hour. (5) Wash 3 times with PBS-T buffer and firmly blot plate against clean paper towels. (6) Dilute serum samples using PBS-T buffer to 50 time, 100 time, 200 time, 400 time, 800 time (perform dilutions in polypropylene tubes) and add 100 μl per well to the ELISA plate. (7) Seal the plate and incubate at 37° C. temperature for 1 hours or at 4° C. overnight. Wash ≥3 times with PBS-T buffer. Washes can be effectively accomplished by filling wells with multichannel pipettor. For increased stringency, after each wash, let the plate stand briefly, flick off the buffer, and blot plates on paper towels before refilling. (8) Dilute the HRP labeled goat anti-rat antibody to its pre-determined optimal concentration in PBS-T buffer (usually between 1/5000-1/20000). Add 100 μl per well. (9) Seal the plate and incubate at room temperature for 1 hour. Wash ≥5 times with PBS-T buffer. (10) For each plate, mix 6 ml of TMB Reagent A (0.5 mM EDTA-Na; 5 mM citric acid; 10% glycerol; 0.04% tetramethyl benzidine) with 6 ml TMB Reagent B (165 mM sodium acetate; 8.3mM citric acid; 0.06% 30% -$H_2O_2$) immediately prior to use. Transfer 100 μL into each well and incubate at room temperature for 30 min. To stop the reaction, add 100 μl of stopping solution (2M $H_2SO_4$). (11) Read the optical density (OD) for each well with a micro-plate reader set to 450 nm.

The OxOx antibody titer reached peak at 28 day post-injection (data not shown). The results on 28 days (FIG. 23) showed that OxOx-B5102 antibody titer dropped significantly when OxOx was pegylated, and dropped further when pegylated with large size of PEG. There was little antibody was detected to against OxOx-B5102 when OxOx was pegylated with 10K, 20K, 30K, and 40K PEG.

SEQUENCE LISTING

```
<160> NUMBER OF SEQ ID NOS: 24

<210> SEQ ID NO 1
<211> LENGTH: 696
<212> TYPE: DNA
<213> ORGANISM: Beta vulgaris subsp. vulgaris
<220> FEATURE:
<221> NAME/KEY: source
<222> LOCATION: 1..696
<223> OTHER INFORMATION: /mol_type="unassigned DNA"
      /organism="Beta vulgaris subsp. vulgaris"

<400> SEQUENCE: 1
atggtctttg caatgagctt tacttctcat atttacgtgg cttcggcctc tgatcctggt      60
ctcctacagg atttttgtgt gggtgtaaat gaccctgatt cagcagtgtt tgtaaatgga     120
aaattctgca agaacccaaa agacgtgaca atcgacgatt tcttatacaa agggtttaat     180
attccctcag acacaaacaa cactcaaaga gcagaagcca cactagtaga tgtcaatcga     240
tttccagcac ttaacacatt aggtgtagcc atggctcgtg tagactttgc gtcctttggc     300
ctaaacacac ctcatttgca ccctcgtggt tctgagatat tcgcggtcct agagggggact     360 ttatatgccg gcattgtcac caccgataat aagcttttcg acacggtgtt gagaaagggt     420
gacatgattg ttttccctca aggcttaatc cacttccagc ttaatcttgg caagacagat     480
```

-continued

```
gctcttgcta ttgcctcttt tgggagccaa tttcctggac gagttaatgt tgctaatggt      540
gtctttggaa ctacgccaca aattttggat gatgtactta cccaagcgtt tcaggtagat      600
aagatggtga ttgagcaact tcgatctcag ttttcaggtc aaacacatc aatcaacact       660 ggaagatcta ttcttaaact cttaactgat gttgct                                696
```

<210> SEQ ID NO 2
<211> LENGTH: 232
<212> TYPE: PRT
<213> ORGANISM: Beta vulgaris subsp. vulgaris

<400> SEQUENCE: 2

```
Met Val Phe Ala Met Ser Phe Thr Ser His Ile Tyr Val Ala Ser Ala
1               5                   10                  15

Ser Asp Pro Gly Leu Leu Gln Asp Phe Cys Val Gly Val Asn Asp Pro
            20                  25                  30

Asp Ser Ala Val Phe Val Asn Gly Lys Phe Cys Lys Asn Pro Lys Asp
        35                  40                  45

Val Thr Ile Asp Asp Phe Leu Tyr Lys Gly Phe Asn Ile Pro Ser Asp
    50                  55                  60

Thr Asn Asn Thr Gln Arg Ala Glu Ala Thr Leu Val Asp Val Asn Arg
65                  70                  75                  80

Phe Pro Ala Leu Asn Thr Leu Gly Val Ala Met Ala Arg Val Asp Phe
                85                  90                  95

Ala Ser Phe Gly Leu Asn Thr Pro His Leu His Pro Arg Gly Ser Glu
            100                 105                 110

Ile Phe Ala Val Leu Glu Gly Thr Leu Tyr Ala Gly Ile Val Thr Thr
        115                 120                 125

Asp Asn Lys Leu Phe Asp Thr Val Leu Arg Lys Gly Asp Met Ile Val
    130                 135                 140

Phe Pro Gln Gly Leu Ile His Phe Gln Leu Asn Leu Gly Lys Thr Asp
145                 150                 155                 160

Ala Leu Ala Ile Ala Ser Phe Gly Ser Gln Phe Pro Gly Arg Val Asn
                165                 170                 175

Val Ala Asn Gly Val Phe Gly Thr Thr Pro Gln Ile Leu Asp Asp Val
            180                 185                 190

Leu Thr Gln Ala Phe Gln Val Asp Lys Met Val Ile Glu Gln Leu Arg
        195                 200                 205

Ser Gln Phe Ser Gly Pro Asn Thr Ser Ile Asn Thr Gly Arg Ser Ile
    210                 215                 220

Leu Lys Leu Leu Thr Asp Val Ala
225                 230
```

<210> SEQ ID NO 3
<211> LENGTH: 648
<212> TYPE: DNA
<213> ORGANISM: Beta vulgaris subsp. vulgaris
<220> FEATURE:
<221> NAME/KEY: source
<222> LOCATION: 1..648
<223> OTHER INFORMATION: /mol_type="unassigned DNA"
      /organism="Beta vulgaris subsp. vulgaris"

<400> SEQUENCE: 3

```
tctgatcctg gtctcctaca ggattttttgt gtgggtgtaa atgaccctga ttcagcagtg      60
tttgtaaatg gaaaattctg caagaaccca aaagacgtga caatcgacga ttcttatac      120 aaagggttta atattccctc agcacaaaac aacactcaaa gagcagaagc cacactagta     180
```

```
gatgtcaatc gatttccagc acttaacaca ttaggtgtag ccatggctcg tgtagacttt    240
gcgtcctttg gcctaaacac acctcatttg caccctcgtg gttctgagat attcgcggtg    300
ctagagggga ctttatatgc cggcattgtc accaccgatt acaagctttt cgacacggtg    360
ttgagaaagg gtgacatgat tgttttccct caaggcttaa tccacttcca gcttaatctt    420
ggcaagacag atgctcttgc tattgcctct tttgggagcc aatttcctgg acgagttaat    480
gttgctaatg gtgtctttgg aactacgcca caaattttgg atgatgtact tacccaagcg    540
tttcaggtag atgagatggt gattcagcaa cttcgatctc agttttcagg tcaaaacata    600
tcaatcaaca ctggaagatc tattcttaaa ctcttaactg atgttgct              648
```

<210> SEQ ID NO 4
<211> LENGTH: 216
<212> TYPE: PRT
<213> ORGANISM: Beta vulgaris subsp. vulgaris

<400> SEQUENCE: 4

Ser Asp Pro Gly Leu Leu Gln Asp Phe Cys Val Gly Val Asn Asp Pro
1               5                   10                  15

Asp Ser Ala Val Phe Val Asn Gly Lys Phe Cys Lys Asn Pro Lys Asp
                20                  25                  30

Val Thr Ile Asp Asp Phe Ile Tyr Lys Gly Phe Asn Ile Pro Ser Asp
            35                  40                  45

Thr Asn Asn Thr Gln Arg Ala Glu Ala Thr Leu Val Asp Val Asn Arg
        50                  55                  60

Phe Pro Ala Leu Asn Thr Leu Gly Val Ala Met Ala Arg Val Asp Phe
65                  70                  75                  80

Ala Ser Phe Gly Leu Asn Thr Pro His Leu His Pro Arg Gly Ser Glu
                85                  90                  95

Ile Phe Ala Val Leu Glu Gly Thr Leu Tyr Ala Gly Ile Val Thr Thr
            100                 105                 110

Asp Asn Lys Leu Phe Asp Thr Val Leu Arg Lys Gly Asp Met Ile Val
        115                 120                 125

Phe Pro Gln Gly Leu Ile His Phe Gln Leu Asn Leu Gly Lys Thr Asp
    130                 135                 140

Ala Leu Ala Ile Ala Ser Phe Gly Ser Gln Phe Pro Gly Arg Val Asn
145                 150                 155                 160

Val Ala Asn Gly Val Phe Gly Thr Thr Pro Gln Ile Leu Asp Asp Val
                165                 170                 175

Leu Thr Gln Ala Phe Gln Val Asp Glu Met Val Ile Gln Gln Leu Arg
            180                 185                 190

Ser Gln Phe Ser Gly Pro Asn Thr Ser Ile Asn Thr Gly Arg Ser Ile
        195                 200                 205

Leu Lys Leu Leu Thr Asp Val Ala
    210                 215

<210> SEQ ID NO 5
<211> LENGTH: 648
<212> TYPE: DNA
<213> ORGANISM: Beta vulgaris subsp. vulgaris
<220> FEATURE:
<221> NAME/KEY: source
<222> LOCATION: 1..648
<223> OTHER INFORMATION: /mol_type="unassigned DNA"
      /organism="Beta vulgaris subsp. vulgaris"

<400> SEQUENCE: 5

```
tccgatcctg cacccttca agattttgt attgctgtaa atgatcccaa ttctgcagtg      60
cttgtgaatg gaaagctttg taagaaccca aagaagtga caatagatga tttcttgtac     120
aaagggttta atatacctgc agacacaaac aacactcaag gagcaagtgc cacactagtg    180
gacattactc tattccctgc agttaacaca caaggagtct ccatggctcg tgtggacttt    240
gcgccatttg gactaaacac ccctcattta catcctcgtg gctcagaggt tttcgcagtg    300
atggaaggga ttatgtatgc tggttttgtg accactgatt ataagctcta tgatacaatt    360
ataaaaaagg gtgatattat tgtgttccca caaggtctaa ttcatttcca acttaatctt    420
gggaagacag atgctttagc aattgcctca tttgggagcc aaaatccagg gagaattaat    480
atcgctgaca gtgtgtttgg tactactccg cgtgttctag atgatgtgct taccaaagga    540
tttcaaatcg atgagttgtt ggtcaagcaa cttcgttctc agttttctac tgataatata    600
tcaacaagca ctggaaggtc attttttgaaa ttgctatctg aaacttat               648
```

<210> SEQ ID NO 6
<211> LENGTH: 216
<212> TYPE: PRT
<213> ORGANISM: Beta vulgaris subsp. vulgaris

<400> SEQUENCE: 6

```
Ser Asp Pro Ala Pro Leu Gln Asp Phe Cys Ile Ala Val Asn Asp Pro
 1               5                   10                  15

Asn Ser Ala Val Leu Val Asn Gly Lys Leu Cys Lys Asn Pro Lys Glu
             20                  25                  30

Val Thr Ile Asp Asp Phe Leu Tyr Lys Gly Phe Asn Ile Pro Ala Asp
         35                  40                  45

Thr Asn Asn Thr Gln Gly Ala Ser Ala Thr Leu Val Asp Ile Thr Leu
     50                  55                  60

Phe Pro Ala Val Asn Thr Gln Gly Val Ser Met Ala Arg Val Asp Phe
 65                  70                  75                  80

Ala Pro Tyr Gly Leu Asn Thr Pro His Leu His Pro Arg Gly Ser Glu
                 85                  90                  95

Val Phe Ala Val Met Glu Gly Ile Met Tyr Ala Gly Phe Val Thr Thr
            100                 105                 110

Asp Tyr Lys Leu Tyr Asp Thr Ile Ile Lys Lys Gly Asp Ile Ile Val
        115                 120                 125

Phe Pro Gln Gly Leu Ile His Phe Gln Leu Asn Leu Gly Lys Thr Asp
    130                 135                 140

Ala Leu Ala Ile Ala Ser Phe Gly Ser Gln Asn Pro Gly Arg Ile Asn
145                 150                 155                 160

Ile Ala Asp Ser Val Phe Gly Thr Thr Pro Arg Val Leu Asp Asp Val
                165                 170                 175

Leu Thr Lys Gly Phe Gln Ile Asp Glu Leu Leu Val Lys Gln Leu Arg
            180                 185                 190

Ser Gln Phe Ser Thr Asp Asn Ile Ser Thr Ser Thr Gly Arg Ser Phe
        195                 200                 205

Leu Lys Leu Leu Ser Glu Thr Tyr
    210                 215
```

<210> SEQ ID NO 7
<211> LENGTH: 639
<212> TYPE: DNA
<213> ORGANISM: Musa acuminata
<220> FEATURE:

```
<221> NAME/KEY: source
<222> LOCATION: 1..639
<223> OTHER INFORMATION: /mol_type="unassigned DNA"
      /organism="Musa acuminata"

<400> SEQUENCE: 7
tttgatccga gtcctctcca agacttttgc gttgctgact acgactccaa cgtgtttgtg    60
aacggattcg cctgcaagaa agctaaggat gtcacggcag atgacttcta cttcaccggc   120
ttagacaagc ccgcgagcac cgccaacgag cttggcgcaa acatcactct cgtcaacgtg   180
gaacgactcc caggcctcaa ctcccttggc gtcgccatgt ctcgcatcga ctacgcgccc   240
ttcggtctca accctcctca ctcgcatcca cgatcgtcgg agatactgca cgtggcggaa   300
ggaacgctct acgccggctt cgtcacctcc aacacggaaa acggcaacct tctcttcgct   360
aagaagctga agaagggcga cgcgtttgtg ttccccaggg gcctcataca cttccagttc   420
aacatcgggg acaccgatgc ggtggcgttc gctaccttcg gcagccagag cccgggtctc   480
gtcaccaccg ccaacgcact gttcggatcg aagccgccca tcgctgatta cattcttgcc   540
caggccgtgc agcttagcaa gacgaccgtg ggctggcttc agcagcagca gtggttggac   600
atcgctcaag aatatggaca acgcttagtt caagctaat                          639

<210> SEQ ID NO 8
<211> LENGTH: 213
<212> TYPE: PRT
<213> ORGANISM: Musa acuminata

<400> SEQUENCE: 8

Phe Asp Pro Ser Pro Leu Gln Asp Phe Cys Val Ala Asp Tyr Asp Ser
1               5                   10                  15

Asn Val Phe Val Asn Gly Phe Ala Cys Lys Lys Ala Lys Asp Val Thr
            20                  25                  30

Ala Asp Asp Phe Tyr Phe Thr Gly Leu Asp Lys Pro Ala Ser Thr Ala
        35                  40                  45

Asn Glu Leu Gly Ala Asn Ile Thr Leu Val Asn Val Glu Arg Leu Pro
    50                  55                  60

Gly Leu Asn Ser Leu Gly Val Ala Met Ser Arg Ile Asp Tyr Ala Pro
65                  70                  75                  80

Phe Gly Leu Asn Pro Pro His Ser His Pro Arg Ser Ser Glu Ile Leu
                85                  90                  95

His Val Ala Glu Gly Thr Leu Tyr Ala Gly Phe Val Thr Ser Asn Thr
            100                 105                 110

Glu Asn Gly Asn Leu Leu Phe Ala Lys Lys Leu Lys Lys Gly Asp Ala
        115                 120                 125

Phe Val Phe Pro Arg Gly Leu Ile His Phe Gln Phe Asn Ile Gly Asp
    130                 135                 140

Thr Asp Ala Val Ala Phe Ala Thr Phe Gly Ser Gln Ser Pro Gly Leu
145                 150                 155                 160

Val Thr Thr Ala Asn Ala Leu Phe Gly Ser Lys Pro Pro Ile Ala Asp
                165                 170                 175

Tyr Ile Leu Ala Gln Ala Val Gln Leu Ser Lys Thr Thr Val Gly Trp
            180                 185                 190

Leu Gln Gln Gln Gln Trp Leu Asp Ile Ala Gln Glu Tyr Gly Gln Arg
        195                 200                 205

Leu Val Gln Ala Asn
    210
```

<210> SEQ ID NO 9
<211> LENGTH: 639
<212> TYPE: DNA
<213> ORGANISM: Beta vulgaris subsp. vulgaris
<220> FEATURE:
<221> NAME/KEY: source
<222> LOCATION: 1..639
<223> OTHER INFORMATION: /mol_type="unassigned DNA"
       /organism="Beta vulgaris subsp. vulgaris"

<400> SEQUENCE: 9

```
atggctcccc tactctacct tgtagtattc ttgcttgctc cttttctctc ccatgctgcg     60
gatcccgatc ctttgctaga ttttgtgta gcggacctta atgcctctcc ctcatttgct    120
aatttcccttt gcaaacaaac ctcaaatgtg acctctgaag atttcttctt tgatgggttt    180
atgaatgagg gaaacacatc aaactcgttt ggatcaaggg tcacacccgg aaacgtcctc    240
acatttcctg cccttaatat gctcgggatt tcaatgaatc gggttgatct tgctgtggat    300
gggatgaacc cgccccattc ccacccacga gcaagtgaga gcggtgtggt gatgaagggg    360
agagttctag tagggttcgt aaccacgggg aatgtgtact attcaaaggt gttggttcca    420
ggacagatgt ttgtaatccc aaggggggttg gttcattttc aaaagaatgt tggacaaaat    480
aaggcactca tcattacagc tttcaatagt cagaatccag gagtagtgtt attatcctca    540
accctgtttg gtacaaaccc ttcaattcca gatgatgttt taagccaaac tttcctagtg    600
gaccagagca ttgtcgaagg aataaaatcc aacttttga                           639
```

<210> SEQ ID NO 10
<211> LENGTH: 212
<212> TYPE: PRT
<213> ORGANISM: Beta vulgaris subsp. vulgaris

<400> SEQUENCE: 10

```
Met Ala Pro Leu Leu Tyr Leu Val Val Phe Leu Leu Ala Pro Phe Leu
1               5                   10                  15

Ser His Ala Ala Asp Pro Asp Pro Leu Leu Asp Phe Cys Val Ala Asp
            20                  25                  30

Leu Asn Ala Ser Pro Ser Phe Ala Asn Phe Pro Cys Lys Gln Thr Ser
        35                  40                  45

Asn Val Thr Ser Glu Asp Phe Phe Asp Gly Phe Met Asn Glu Gly
    50                  55                  60

Asn Thr Ser Asn Ser Phe Gly Ser Arg Val Thr Pro Gly Asn Val Leu
65                  70                  75                  80

Thr Phe Pro Ala Leu Asn Met Leu Gly Ile Ser Met Asn Arg Val Asp
                85                  90                  95

Leu Ala Val Asp Gly Met Asn Pro Pro His Ser His Pro Arg Ala Ser
            100                 105                 110

Glu Ser Gly Val Val Met Lys Gly Arg Val Leu Val Gly Phe Val Thr
        115                 120                 125

Thr Gly Asn Val Tyr Tyr Ser Lys Val Leu Val Pro Gly Gln Met Phe
    130                 135                 140

Val Ile Pro Arg Gly Leu Val His Phe Gln Lys Asn Val Gly Gln Asn
145                 150                 155                 160

Lys Ala Leu Ile Ile Thr Ala Phe Asn Ser Gln Asn Pro Gly Val Val
                165                 170                 175

Leu Leu Ser Ser Thr Leu Phe Gly Thr Asn Pro Ser Ile Pro Asp Asp
            180                 185                 190
```

Val Leu Ser Gln Thr Phe Leu Val Asp Gln Ser Ile Val Glu Gly Ile
            195                 200                 205

Lys Ser Asn Phe
    210

<210> SEQ ID NO 11
<211> LENGTH: 660
<212> TYPE: DNA
<213> ORGANISM: Beta vulgaris subsp. vulgaris
<220> FEATURE:
<221> NAME/KEY: source
<222> LOCATION: 1..660
<223> OTHER INFORMATION: /mol_type="unassigned DNA"
      /organism="Beta vulgaris subsp. vulgaris"

<400> SEQUENCE: 11
atggaagtcg tcgcagctgt atcttttctg gccgtgttat tggctctggt ttcccctgcc      60
ctcgccaatg atcctgatat gctccaagat gtttgtgtcg ctgattccac tctggagtg     120 aaattgaatg gatttgcatg caaggatgca gcaagcatta ccccagaaga cttcttcttt     180
gctggaatat ccaaacccgg aatgacaaac aatacaatga atccctagt aaccggagct     240 aacgtcgaaa agataccggg tttaaacaca ctcggagtgt ccatgggtcg tatcgacttc     300
ggcccaggtg gtcttaaccc acctcacact cacccacgag ccacagaaat ggtctttgtg     360
ttatatggag aattggacgt tggtttccta actacttcta ataagctcat ttctaagcat     420
attaaaactg gtgaaacttt tgttttcct agagggttag tccactttca gaaaaataat     480
ggggataaac ctgctgcttt agtcactgct tttaatagtc agttgcctgg cacccaatca     540
atagctgcca cgttgtttac gtcgacccca cctgttccag ataatgtttt aactatgact     600
ttccaagtcg gtactaaaca agtccagaag atcaaggcta ggctcgctcc taagaagtaa     660

<210> SEQ ID NO 12
<211> LENGTH: 219
<212> TYPE: PRT
<213> ORGANISM: Beta vulgaris subsp. vulgaris

<400> SEQUENCE: 12

Met Glu Val Val Ala Ala Val Ser Phe Leu Ala Val Leu Leu Ala Leu
1               5                   10                  15

Val Ser Pro Ala Leu Ala Asn Asp Pro Asp Met Leu Gln Asp Val Cys
            20                  25                  30

Val Ala Asp Ser Thr Ser Gly Val Lys Leu Asn Gly Phe Ala Cys Lys
        35                  40                  45

Asp Ala Ala Ser Ile Thr Pro Glu Asp Phe Phe Ala Gly Ile Ser
    50                  55                  60

Lys Pro Gly Met Thr Asn Asn Thr Met Lys Ser Leu Val Thr Gly Ala
65                  70                  75                  80

Asn Val Glu Lys Ile Pro Gly Leu Asn Thr Leu Gly Val Ser Met Gly
                85                  90                  95

Arg Ile Asp Phe Gly Pro Gly Gly Leu Asn Pro His Thr His Pro
            100                 105                 110

Arg Ala Thr Glu Met Val Phe Val Leu Tyr Gly Glu Leu Asp Val Gly
        115                 120                 125

Phe Leu Thr Thr Ser Asn Lys Leu Ile Ser Lys His Ile Lys Thr Gly
    130                 135                 140

Glu Thr Phe Val Phe Pro Arg Gly Leu Val His Phe Gln Lys Asn Asn
145                 150                 155                 160

Gly Asp Lys Pro Ala Ala Leu Val Thr Ala Phe Asn Ser Gln Leu Pro
            165                 170                 175

Gly Thr Gln Ser Ile Ala Ala Thr Leu Phe Thr Ser Thr Pro Pro Val
        180                 185                 190

Pro Asp Asn Val Leu Thr Met Thr Phe Gln Val Gly Thr Lys Gln Val
    195                 200                 205

Gln Lys Ile Lys Ala Arg Leu Ala Pro Lys Lys
210                 215

<210> SEQ ID NO 13
<211> LENGTH: 669
<212> TYPE: DNA
<213> ORGANISM: Beta vulgaris subsp. vulgaris
<220> FEATURE:
<221> NAME/KEY: source
<222> LOCATION: 1..669
<223> OTHER INFORMATION: /mol_type="unassigned DNA"
      /organism="Beta vulgaris subsp. vulgaris"

<400> SEQUENCE: 13
atggcggctg tttgggtagt cttggtggtg ctagcggcgg cttttgctgt tggggtcttt      60
gccagcgatc ctgatatgct tcaagatgtt tgtgttgctg atcgtacatc tggaatatta     120
gtgaatggat tcacatgtaa aaatatgacc atgataaccc ctgaagactt cttcttcacc     180
ggaatttcac aaccaggcca aatcacaaat aaaatccttg gttctcgagt caccggagcg     240
aatgtgcagg acatccctgg tctcaacacc ttgggagtct cgatggctcg tgtcgacttt     300 actcccctacg gtctaaaccc acctcacatt caccctagaa tcgtccaccc tcgtgccact     360
gaaatgatct atgttcttaa gggtgaattg tacgttggtt ttataacgac cgacaataag     420
ctcatttcca aggttgttaa agctggagaa gtatttgttt tccctagagg tttggctcac     480
tttcagaaaa acatgttgaa atatccagct gctgcattag ctgccttcaa cagccaactt     540
ccaggcactc aacaatttgc agctgctctc tttacttcca atcctcctgt gtctaatgat     600
gtgttggctc aggcttttaa cattgacgaa cacaatgtca aaagattag ggctggcctt     660 actccatag                                                              669

<210> SEQ ID NO 14
<211> LENGTH: 217
<212> TYPE: PRT
<213> ORGANISM: Beta vulgaris subsp. vulgaris

<400> SEQUENCE: 14

Met Ala Ala Val Trp Val Val Leu Val Val Leu Ala Ala Ala Phe Ala
1               5                   10                  15

Val Gly Val Phe Ala Ser Asp Pro Asp Met Leu Gln Asp Val Cys Val
            20                  25                  30

Ala Asp Arg Thr Ser Gly Ile Leu Val Asn Gly Phe Thr Cys Lys Asn
        35                  40                  45

Met Thr Met Ile Thr Pro Glu Asp Phe Phe Thr Gly Ile Ser Gln
    50                  55                  60

Pro Gly Gln Ile Thr Asn Lys Ile Leu Gly Ser Arg Val Thr Gly Ala
65                  70                  75                  80

Asn Val Gln Asp Ile Pro Gly Leu Asn Thr Leu Gly Val Ser Met Ala
                85                  90                  95

Arg Val Asp Phe Thr Pro Tyr Gly Leu Asn Pro Pro His Ile His Pro
            100                 105                 110

Arg Ala Thr Glu Met Ile Tyr Val Leu Lys Gly Glu Leu Tyr Val Gly

```
                    115                 120                 125
Phe Ile Thr Thr Asp Asn Lys Leu Ile Ser Lys Val Val Lys Ala Gly
    130                 135                 140

Glu Val Phe Val Phe Pro Arg Gly Leu Ala His Phe Gln Lys Asn Met
145                 150                 155                 160

Leu Lys Tyr Pro Ala Ala Leu Ala Ala Phe Asn Ser Gln Leu Pro
                165                 170                 175

Gly Thr Gln Gln Phe Ala Ala Leu Phe Thr Ser Asn Pro Pro Val
            180                 185                 190

Ser Asn Asp Val Leu Ala Gln Ala Phe Asn Ile Asp Glu His Asn Val
                195                 200                 205

Lys Lys Ile Arg Ala Gly Leu Thr Pro
    210                 215

<210> SEQ ID NO 15
<211> LENGTH: 660
<212> TYPE: DNA
<213> ORGANISM: Musa acuminata
<220> FEATURE:
<221> NAME/KEY: source
<222> LOCATION: 1..660
<223> OTHER INFORMATION: /mol_type="unassigned DNA"
      /organism="Musa acuminata"

<400> SEQUENCE: 15
atggagtcgc actacacgaa gagaccattc ctcctctttc tctccttcac cgtcctcctc    60
gtgttgatcc gcgctgaccc tgatcctctc caggacttct gcgtcgccga cctcggagct   120
actgtggtcg tcaatgggtt cccgtgcaag cccgcgtccg gagtcacgtc cgacgacttc   180
ttcttcgccg gactgtccag ggagggcaac accagcaata tcttcgggtc caacgtgacc   240
aacgccaaca tgctcagctt cccgggggctc aacaccctcg gcgtctccat gaaccgcgtc   300
gacgtcgccc ccggcggcac caacccgccc cacagccacc cgagggctac cgagctcatc   360
atcctcctca agggccggct gctggtgggg ttcatcagca ccagtaacca gttcttctcc   420
aaggtcttga cccccggcga gatgttcgtg gtgcccaagg ggctcatcca cttccagtac   480
aacgtcggca aggagaaggc gctcgccatc accaccttcg acagccagct ccccggagta   540
gtgatcgcct ccaccaccct gttcgcatcg aatccggcga ttcccgacga tgtgctggcc   600
aaagcttttc agtggacgc gaaggtcgtc gctctcatca gtccaagtt tgagagataa    660

<210> SEQ ID NO 16
<211> LENGTH: 219
<212> TYPE: PRT
<213> ORGANISM: Musa acuminata

<400> SEQUENCE: 16

Met Glu Ser His Tyr Thr Lys Arg Pro Phe Leu Leu Phe Leu Ser Phe
1               5                   10                  15

Thr Val Leu Leu Val Leu Ile Arg Ala Asp Pro Asp Pro Leu Gln Asp
                20                  25                  30

Phe Cys Val Ala Asp Leu Gly Ala Thr Val Val Val Asn Gly Phe Pro
            35                  40                  45

Cys Lys Pro Ala Ser Gly Val Thr Ser Asp Asp Phe Phe Phe Ala Gly
        50                  55                  60

Leu Ser Arg Glu Gly Asn Thr Ser Asn Ile Phe Gly Ser Asn Val Thr
65                  70                  75                  80

Asn Ala Asn Met Leu Ser Phe Pro Gly Leu Asn Thr Leu Gly Val Ser
```

```
                85                  90                  95
Met Asn Arg Val Asp Val Ala Pro Gly Gly Thr Asn Pro His Ser
            100                 105                 110

His Pro Arg Ala Thr Glu Leu Ile Ile Leu Lys Gly Arg Leu Leu
            115                 120                 125

Val Gly Phe Ile Ser Thr Ser Asn Gln Phe Phe Ser Lys Val Leu Asn
            130                 135                 140

Pro Gly Glu Met Phe Val Val Pro Lys Gly Leu Ile His Phe Gln Tyr
145                 150                 155                 160

Asn Val Gly Lys Glu Lys Ala Leu Ala Ile Thr Thr Phe Asp Ser Gln
                165                 170                 175

Leu Pro Gly Val Val Ile Ala Ser Thr Thr Leu Phe Ala Ser Asn Pro
            180                 185                 190

Ala Ile Pro Asp Asp Val Leu Ala Lys Ala Phe Gln Val Asp Ala Lys
            195                 200                 205

Val Val Ala Leu Ile Lys Ser Lys Phe Glu Arg
            210                 215
```

<210> SEQ ID NO 17
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Primer 510F"
      /organism="Artificial Sequence"

<400> SEQUENCE: 17
ccgctcgaga aaagatctga tcctggtctc ctacag                36

<210> SEQ ID NO 18
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /mol_type="unassigned DNA"
      /note="Primer 510R"
      /organism="Artificial Sequence"

<400> SEQUENCE: 18
aaatatgcgg ccgctcaagc aacatcagtt aagagtt                37

<210> SEQ ID NO 19
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer 560F"
      /organism="Artificial Sequence"

<400> SEQUENCE: 19
ccgctcgaga aaagatccga tcctgcaccc ctt                33

<210> SEQ ID NO 20
<211> LENGTH: 39
<212> TYPE: DNA
<213> ORGANISM: Artificial Sequence

```
<220> FEATURE:
<221> NAME/KEY: source
<222> LOCATION: 1..39
<223> OTHER INFORMATION: /mol_type="unassigned DNA"
      /note="Primer 5601R"
      /organism="Artificial Sequence"

<400> SEQUENCE: 20
aaatatgcgg ccgctcaata agtttcagat agcaatttc                               39

<210> SEQ ID NO 21
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Primer 30640F"
      /organism="Artificial Sequence"

<400> SEQUENCE: 21
ccgctcgaga aaagatttga tccgagtcct ctcca                                   35

<210> SEQ ID NO 22
<211> LENGTH: 38
<212> TYPE: DNA
<213> ORGANISM: Artificial Sequence
<220> FEATURE:
<221> NAME/KEY: source
<222> LOCATION: 1..38
<223> OTHER INFORMATION: /mol_type="unassigned DNA"
      /note="Primer 30640R"
      /organism="Artificial Sequence"

<400> SEQUENCE: 22
aaatatgcgg ccgctcaatt agcttgaact aagcgttg                                38

<210> SEQ ID NO 23
<211> LENGTH: 5900
<212> TYPE: DNA
<213> ORGANISM: Artificial Sequence
<220> FEATURE:
<221> NAME/KEY: source
<222> LOCATION: 1..5900
<223> OTHER INFORMATION: /mol_type="unassigned DNA"
      /note="pET-32a(+) plasmid sequence"
      /organism="Artificial Sequence"

<400> SEQUENCE: 23
tggcgaatgg gacgcgccct gtagcggcgc attaagcgcg gcgggtgtgg tggttacgcg        60
cagcgtgacc gctacacttg ccagcgccct agcgcccgct cctttcgctt tcttcccttc       120
ctttctcgcc acgttcgccg gctttccccg tcaagctcta aatcggggGC tcccttTagg       180
gttccgattt agtgctttac ggcacctcga ccccaaaaaa cttgattagg gtgatggttc       240
acgtagtggg ccatcgccct gatagacggt ttttcgccct ttgacgttgg agtccacgtt       300
ctttaatagt ggactcttgt tccaaactgg aacaacactc aaccctatct cggtctattc       360
ttttgattta agggattt tgccgatttc ggcctattgg ttaaaaaatg agctgatttta       420 acaaaattt aacgcgaatt ttaacaaaat attaacgttt acaatttcag gtggcacttt       480
tcggggaaat gtgcgcggaa cccctatttg tttatttttc taaatacatt caaatatgta       540
tccgctcatg agacaataac cctgataaat gcttcaataa tattgaaaaa ggaagagtat       600
gagtattcaa catttccgtg tcgcccttat tccctttttt gcggcatttt gccttcctgt       660
```

```
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccgagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct aacgtgagt tttcgttcca ctgagcgtca gaccccgtag aaaagatcaa   1620
aggatcttct tgagatcctt ttttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaagggg atttctgttc atgggggtaa   2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
```

```
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt tggtggcgg    3360 gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgt ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840 cccagcagg gaaaatcctg tttgatggtg gttaacggcg ggatataaca tgagctgtct    3900
tcggtatcgt cgtatcccac taccgagatg tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat attttatgcca gccagccaga    4140 cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg cgctatcat gccataccgc gaaaggtttt cgccattcg    4800 atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatacc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacatat gagcgataaa    5220
attattcacc tgactgacga cagttttgac acggatgtac tcaaagcgga cggggcgatc    5280
ctcgtcgatt tctgggcaga gtggtgcggt ccgtgcaaaa tgatcgcccc gattctggat    5340
gaaatcgctg acgaatatca gggcaaactg accgttgcaa aactgaacat cgatcaaaac    5400
```

| | |
|---|---|
| cctggcactg cgccgaaata tggcatccgt ggtatcccga ctctgctgct gttcaaaaac | 5460 |
| ggtgaagtgg cggcaaccaa agtgggtgca ctgtctaaag gtcagttgaa agagttcctc | 5520 |
| gacgctaacc tggccggttc tggttctggc catatgcacc atcatcatca tcattcttct | 5580 |
| ggtctggtgc cacgcggttc tggtatgaaa gaaaccgctg ctgctaaatt cgaacgccag | 5640 |
| cacatggaca gcccagatct gggtaccgac gacgacgaca aggccatggc tgatatcgga | 5700 |
| tccgaattcg agctccgtcg acaagcttgc ggccgcactc gagcaccacc accaccacca | 5760 |
| ctgagatccg gctgctaaca aagcccgaaa ggaagctgag ttggctgctg ccaccgctga | 5820 |
| gcaataacta gcataacccc ttggggcctc taaacgggtc ttgaggggtt ttttgctgaa | 5880 |
| aggaggaact atatccggat | 5900 |

<210> SEQ ID NO 24
<211> LENGTH: 5423
<212> TYPE: DNA
<213> ORGANISM: Artificial Sequence
<220> FEATURE:
<221> NAME/KEY: source
<222> LOCATION: 1..5423
<223> OTHER INFORMATION: /mol_type="unassigned DNA"
    /note="pAT plasmid"
    /organism="Artificial Sequence"

<400> SEQUENCE: 24

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta agggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttatttttc taaatacatt caaatatgta | 540 |
| tccgctcatg agacaataac cctgataaat gcttcaataa tattgaaaaa ggaagagtat | 600 |
| gagtattcaa catttccgtg tcgcccttat tccctttttt gcggcatttt gccttcctgt | 660 |
| ttttgctcac ccagaaacgc tggtgaaagt aaaagatgct gaagatcagt tgggtgcacg | 720 |
| agtgggttac atcgaactgg atctcaacag cggtaagatc cttgagagtt ttcgccccga | 780 |
| agaacgtttt ccaatgatga gcacttttaa agttctgcta tgtggcgcgg tattatcccg | 840 |
| tattgacgcc gggcaagagc aactcggtcg ccgcatacac tattctcaga atgacttggt | 900 |
| tgagtactca ccagtcacag aaaagcatct tacggatggc atgacagtaa gagaattatg | 960 |
| cagtgctgcc ataaccatga gtgataacac tgcggccaac ttacttctga caacgatcgg | 1020 |
| aggaccgaag gagctaaccg cttttttgca acatgggg gatcatgtaa ctcgccttga | 1080 |
| tcgttgggaa ccggagctga atgaagccat accaaacgac gagcgtgaca ccacgatgcc | 1140 |
| tgcagcaatg gcaacaacgt tgcgcaaact attaactggc gaactactta ctctagcttc | 1200 |
| ccggcaacaa ttaatagact ggatggaggc ggataaagtt gcaggaccac ttctgcgctc | 1260 |
| ggcccttccg gctggctggt ttattgctga taaatctgga gccggtgagc gtgggtctcg | 1320 |
| cggtatcatt gcagcactgg ggccagatgg taagccctcc cgtatcgtag ttatctacac | 1380 |
| gacggggagt caggcaacta tggatgaacg aaatagacag atcgctgaga taggtgcctc | 1440 |

| | |
|---|---|
| actgattaag cattggtaac tgtcagacca agtttactca tatatacttt agattgattt | 1500 |
| aaaacttcat ttttaattta aaaggatcta ggtgaagatc cttttttgata atctcatgac | 1560 |
| caaaatccct taacgtgagt tttcgttcca ctgagcgtca gaccccgtag aaaagatcaa | 1620 |
| aggatcttct tgagatcctt tttttctgcg cgtaatctgc tgcttgcaaa caaaaaaacc | 1680 |
| accgctacca gcggtggttt gtttgccgga tcaagagcta ccaactcttt ttccgaaggt | 1740 |
| aactggcttc agcagagcgc agataccaaa tactgtcctt ctagtgtagc cgtagttagg | 1800 |
| ccaccacttc aagaactctg tagcaccgcc tacatacctc gctctgctaa tcctgttacc | 1860 |
| agtggctgct gccagtggcg ataagtcgtg tcttaccggg ttggactcaa gacgatagtt | 1920 |
| accggataag gcgcagcggt cgggctgaac ggggggttcg tgcacacagc ccagcttgga | 1980 |
| gcgaacgacc tacaccgaac tgagatacct acagcgtgag ctatgagaaa gcgccacgct | 2040 |
| tcccgaaggg agaaaggcgg acaggtatcc ggtaagcggc agggtcggaa caggagagcg | 2100 |
| cacgagggag cttccagggg gaaacgcctg gtatctttat agtcctgtcg ggtttcgcca | 2160 |
| cctctgactt gagcgtcgat ttttgtgatg ctcgtcaggg gggcggagcc tatggaaaaa | 2220 |
| cgccagcaac gcggcctttt tacggttcct ggccttttgc tggccttttg ctcacatgtt | 2280 |
| ctttcctgcg ttatcccctg attctgtgga taaccgtatt accgcctttg agtgagctga | 2340 |
| taccgctcgc cgcagccgaa cgaccgagcg cagcgagtca gtgagcgagg aagcggaaga | 2400 |
| gcgcctgatg cggtattttc tccttacgca tctgtgcggt atttcacacc gcatatatgg | 2460 |
| tgcactctca gtacaatctg ctctgatgcc gcatagttaa gccagtatac actccgctat | 2520 |
| cgctacgtga ctgggtcatg gctgcgcccc gacacccgcc aacacccgct gacgcgccct | 2580 |
| gacgggcttg tctgctcccg gcatccgctt acagacaagc tgtgaccgtc tccgggagct | 2640 |
| gcatgtgtca gaggttttca ccgtcatcac cgaaacgcgc gaggcagctg cggtaaagct | 2700 |
| catcagcgtg gtcgtgaagc gattcacaga tgtctgcctg ttcatccgcg tccagctcgt | 2760 |
| tgagtttctc cagaagcgtt aatgtctggc ttctgataaa gcgggccatg ttaagggcgg | 2820 |
| ttttttcctg tttggtcact gatgcctccg tgtaagggg atttctgttc atggggtaa | 2880 |
| tgataccgat gaaacgagag aggatgctca cgatacgggg tactgatgat gaacatgccc | 2940 |
| ggttactgga cgttgtgag ggtaaacaac tggcggtatg gatgcggcgg gaccagagaa | 3000 |
| aaatcactca gggtcaatgc cagcgcttcg ttaatacaga tgtaggtgtt ccacagggta | 3060 |
| gccagcagca tcctgcgatg cagatccgga acataatggt gcagggcgct gacttccgcg | 3120 |
| tttccagact ttacgaaaca cggaaaccga agaccattca tgttgttgct caggtcgcag | 3180 |
| acgttttgca gcagcagtcg cttcacgttc gctcgcgtat cggtgattca ttctgctaac | 3240 |
| cagtaaggca accccgccag cctagccggg tcctcaacga caggagcacg atcatgcgca | 3300 |
| cccgtggggc cgccatgccg gcgataatgg cctgcttctc gccgaaacgt ttggtggcgg | 3360 |
| gaccagtgac gaaggcttga gcgagggcgt gcaagattcc gaataccgca agcgacaggc | 3420 |
| cgatcatcgt cgcgctccag cgaaagcggt cctcgccgaa aatgacccag agcgctgccg | 3480 |
| gcacctgtcc tacgagttgc atgataaaga agacagtcat aagtgcggcg acgatagtca | 3540 |
| tgccccgcgc ccaccggaag gagctgactg ggttgaaggc tctcaagggc atcggtcgag | 3600 |
| atcccggtgc ctaatgagtg agctaactta cattaattgc gttgcgctca ctgcccgctt | 3660 |
| tccagtcggg aaacctgtcg tgccagctgc attaatgaat cggccaacgc gcggggagag | 3720 |
| gcggtttgcg tattgggcgc cagggtggtt tttcttttca ccagtgagac gggcaacagc | 3780 |

```
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagatg tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
cgatctcgat cccgcgaaat taatacgact cactataggg gaattgtgag cggataacaa    5160
ttcccctcta gaaataattt tgtttaactt taagaaggag atatacccat ggctgatatc    5220
ggatccgaat tcgagctccg tcgacaagct tgcggccgca ctcgagcacc accaccacca    5280
ccactgagat ccggctgcta acaaagcccg aaaggaagct gagttggctg ctgccaccgc    5340
tgagcaataa ctagcataac cccttggggc ctctaaacgg gtcttgaggg gttttttgct    5400
gaaaggagga actatatccg gat                                            5423
```

The invention claimed is:

1. A method for treating a subject suffering from a disease associated with excess oxalate, wherein the disease is selected from hyperoxaluria, vulvodynia, oxalosis associated with end stage renal disease, and urolithiasis, comprising parenterally administering to the subject a recombinant oxalate oxidase having the amino acid sequence of SEQ ID NO: 2, SEQ ID NO: 4, SEQ ID NO: 6, or SEQ ID NO: 8.

2. The method according to claim 1, wherein the recombinant oxalate oxidase has the amino acid sequence of SEQ ID NO: 2.

3. The method according to claim 1, wherein the recombinant oxalate oxidase has the amino acid sequence of SEQ ID NO: 4.

4. The method according to claim 1, wherein the recombinant oxalate oxidase has the amino acid sequence of SEQ ID NO: 6.

5. The method according to claim 1, wherein the recombinant oxalate oxidase is pegylated.

6. The method according to claim 1, wherein the recombinant oxalate oxidase has the amino acid sequence of SEQ ID NO: 8.

7. The method according to claim 1, wherein the hyperoxaluria is primary hyperoxaluria, secondary hyperoxaluria, or is associated with Zellweger syndrome.

8. The method according to claim 1, wherein the hyperoxaluria is associated with Crohn's disease, inflammatory bowel disease, or colitis.

9. A method for treating a subject suffering from a disease associated with excess oxalate, wherein the disease is selected from asthma, chronic obstructive, sarcoidosis, pulmonary disease (COPD), and fibromyalgia, comprising parenterally administering to the subject a recombinant oxalate oxidase having the amino acid sequence of SEQ ID NO: 2, SEQ ID NO: 4, SEQ ID NO: 6, or SEQ ID NO: 8.

10. The method according to claim 9, wherein the recombinant oxalate oxidase has the amino acid sequence of SEQ ID NO: 2.

11. The method according to claim 9, wherein the recombinant oxalate oxidase has the amino acid sequence of SEQ ID NO: 4.

12. The method according to claim 9, wherein the recombinant oxalate oxidase has the amino acid sequence of SEQ ID NO: 6.

13. The method according to claim 9, wherein the recombinant oxalate oxidase has the amino acid sequence of SEQ ID NO: 8.

14. The method according to claim 9, wherein the recombinant oxalate oxidase is pegylated.

15. A method for treating a subject suffering from a disease associated with excess oxalate, wherein the disease is a cardiac conductance disorder, comprising parenterally administering to the subject a recombinant oxalate oxidase having the amino acid sequence of SEQ ID NO: 2, SEQ ID NO: 4, SEQ ID NO: 6, or SEQ ID NO: 8.

16. The method according to claim 15, wherein the recombinant oxalate oxidase has the amino acid sequence of SEQ ID NO: 2.

17. The method according to claim 15, wherein the recombinant oxalate oxidase has the amino acid sequence of SEQ ID NO: 4.

18. The method according to claim 15, wherein the recombinant oxalate oxidase has the amino acid sequence of SEQ ID NO: 6.

19. The method according to claim 15, wherein the recombinant oxalate oxidase has the amino acid sequence of SEQ ID NO: 8.

20. The method according to claim 15, wherein the recombinant oxalate oxidase is pegylated.

* * * * *